United States Patent
Frysz et al.

(10) Patent No.: US 12,017,065 B2
(45) Date of Patent: *Jun. 25, 2024

(54) ELECTRICALLY CONDUCTIVE COATING APPLIED TO AN OXIDIZABLE SURFACE OF AN AIMD FERRULE OR HOUSING TO PROVIDE AN OXIDE-RESISTANT CONNECTION TO AN EMI FILTER CAPACITOR, AN EMI FILTER CIRCUIT OR AIMD ELECTRONIC CIRCUITS AND COMPONENTS

(71) Applicant: Greatbatch Ltd., Clarence, NY (US)

(72) Inventors: Christine A. Frysz, Orchard Park, NY (US); Robert A. Stevenson, Canyon County, CA (US); Jason Woods, Carson City, NV (US)

(73) Assignee: Greatbatch Ltd., Clarence, NY (US)

( * ) Notice: Subject to any disclaimer, the term of this patent is extended or adjusted under 35 U.S.C. 154(b) by 205 days.

This patent is subject to a terminal disclaimer.

(21) Appl. No.: 17/315,895

(22) Filed: May 10, 2021

(65) Prior Publication Data

US 2021/0348253 A1    Nov. 11, 2021

Related U.S. Application Data

(63) Continuation-in-part of application No. 17/181,416, filed on Feb. 22, 2021, now Pat. No. 11,541,233.

(Continued)

(51) Int. Cl.
*A61N 1/08* (2006.01)
*A61N 1/37* (2006.01)
(Continued)

(52) U.S. Cl.
CPC ............ *A61N 1/08* (2013.01); *A61N 1/3718* (2013.01); *A61N 1/375* (2013.01); *A61N 1/3754* (2013.01);
(Continued)

(58) Field of Classification Search
CPC ........ A61N 1/08; A61N 1/086; A61N 1/3718; A61N 1/375; A61N 1/3754; A61N 1/3758;
(Continued)

(56) References Cited

U.S. PATENT DOCUMENTS

| 4,424,551 A | 1/1984 | Stevenson et al. |
| 5,333,095 A | 7/1994 | Stevenson et al. |

(Continued)

FOREIGN PATENT DOCUMENTS

| EP | 3081258 A1 | 10/2016 |
| EP | 3569284 A1 | 11/2019 |

OTHER PUBLICATIONS

Camm, "Editor-in-Chief", European Pacing, Arrhythmias and Cardiac Electrophysiology, Sep. 1, 2009, 1238-1239.

(Continued)

*Primary Examiner* — Pamela M. Bays
(74) *Attorney, Agent, or Firm* — Michael F. Scalise

(57) ABSTRACT

A hermetically sealed feedthrough assembly for an active implantable medical device having an oxide-resistant electrical attachment for connection to an EMI filter, an EMI filter circuit board, an AIMD circuit board, or AIMD electronics. The oxide-resistant electrical attachment, including an oxide-resistant coating layer that is disposed on the device side surface of the hermetic seal ferrule over which an optional ECA stripe may be provided. The optional ECA stripe may comprise one of a thermal-setting electrically conductive adhesive, an electrically conductive polymer, an electrically conductive epoxy, an electrically conductive silicone, an electrically conductive polyamide, or an electrically conductive polyimide, such as those manufactured by Ablestick Corporation. The oxide-free coating layer may comprise one of gold, platinum, palladium, silver, iridium, (Continued)

rhenium, rhodium, tantalum, tungsten, niobium, zirconium, vanadium, and combinations or alloys thereof. As used herein, the oxide-free coating layer is not limiting and as will be taught, in addition to sputtering, there are many other methods of applying a proud oxide-free surface on either an AIMD ferrule or an AIMD housing.

22 Claims, 50 Drawing Sheets

Related U.S. Application Data

(60) Provisional application No. 63/021,858, filed on May 8, 2020.

(51) Int. Cl.
*A61N 1/375* (2006.01)
*C22C 14/00* (2006.01)
*H05K 5/06* (2006.01)
*C22C 5/02* (2006.01)
*H01G 4/35* (2006.01)
*H05K 9/00* (2006.01)

(52) U.S. Cl.
CPC ............... *C22C 14/00* (2013.01); *H05K 5/06* (2013.01); *A61N 1/086* (2017.08); *A61N 1/37512* (2017.08); *A61N 1/3758* (2013.01); *C22C 5/02* (2013.01); *H01G 4/35* (2013.01); *H05K 9/0064* (2013.01)

(58) Field of Classification Search
CPC ........ A61N 1/3752; C22C 14/00; H05K 5/06; H01G 4/35
See application file for complete search history.

(56) References Cited

U.S. PATENT DOCUMENTS

| | | | |
|---|---|---|---|
| 5,896,267 A | 4/1999 | Hittman et al. | |
| 5,905,627 A | 5/1999 | Brendel et al. | |
| 5,959,829 A | 9/1999 | Stevenson et al. | |
| 5,973,906 A | 10/1999 | Stevenson et al. | |
| 6,275,369 B1 | 8/2001 | Stevenson et al. | |
| 6,529,103 B1 | 3/2003 | Brendel et al. | |
| 6,534,112 B1 * | 3/2003 | Bouchier | A61L 29/16 |
| | | | 427/430.1 |
| 6,765,779 B2 | 7/2004 | Stevenson et al. | |
| 6,888,715 B2 | 5/2005 | Stevenson et al. | |
| 7,038,900 B2 | 5/2006 | Stevenson et al. | |
| 8,352,033 B2 | 1/2013 | Kroll | |
| 8,457,760 B2 | 6/2013 | Dabney et al. | |
| 8,700,156 B2 | 4/2014 | Kroll | |
| 8,812,103 B2 | 8/2014 | Kroll et al. | |
| 8,825,158 B2 | 9/2014 | Swerdlow | |
| 9,272,150 B2 | 3/2016 | Kroll et al. | |
| 9,427,577 B2 | 8/2016 | Kroll et al. | |
| 9,486,624 B2 | 11/2016 | Swerdlow | |
| 9,492,659 B2 | 11/2016 | Brendel et al. | |
| 9,636,500 B2 | 5/2017 | Swerdlow et al. | |
| 9,675,799 B2 | 6/2017 | Kroll et al. | |
| 9,757,558 B2 | 9/2017 | Stevenson et al. | |
| 9,814,876 B2 | 11/2017 | Swerdlow | |
| 9,821,156 B2 | 11/2017 | Kroll et al. | |
| 9,827,416 B2 | 11/2017 | Swerdlow | |
| 11,541,233 B2 * | 1/2023 | Frysz | H01G 4/35 |
| 11,633,612 B2 * | 4/2023 | Frysz | H01G 4/35 |
| | | | 607/5 |
| 2004/0235549 A1 | 11/2004 | Struble et al. | |
| 2006/0282126 A1 * | 12/2006 | Fischbach | A61N 1/3754 |
| | | | 607/37 |
| 2007/0123949 A1 | 5/2007 | Dabney et al. | |
| 2009/0163980 A1 | 6/2009 | Stevenson | |
| 2009/0243756 A1 * | 10/2009 | Stevenson | A61N 1/3754 |
| | | | 333/167 |
| 2009/0322632 A1 | 12/2009 | Milosevic | |
| 2010/0191236 A1 | 7/2010 | Johnson et al. | |
| 2010/0208397 A1 | 8/2010 | Johnson et al. | |
| 2013/0282122 A1 * | 10/2013 | Ullrich, Jr. | A61F 2/4465 |
| | | | 623/17.16 |
| 2014/0155947 A1 | 6/2014 | Kroll et al. | |
| 2014/0168917 A1 | 6/2014 | Marzano et al. | |
| 2014/0194964 A1 * | 7/2014 | Woods | H01R 13/7195 |
| | | | 607/119 |
| 2015/0217111 A1 | 8/2015 | Stevenson et al. | |
| 2015/0343224 A1 * | 12/2015 | Woods | H01G 4/228 |
| | | | 607/116 |
| 2016/0301369 A1 | 10/2016 | Heaney et al. | |
| 2016/0367821 A1 * | 12/2016 | Frysz | A61N 1/3754 |

OTHER PUBLICATIONS

Extendedepsearch, Extended European Search Report, Application No. 19154697.7, dated Jun. 4, 2019.

"Extended European Search Report Dated Dec. 15, 2020, Application No. 20180915.9".

* cited by examiner (POOR PRACTICE)

BODY FLUID SIDE

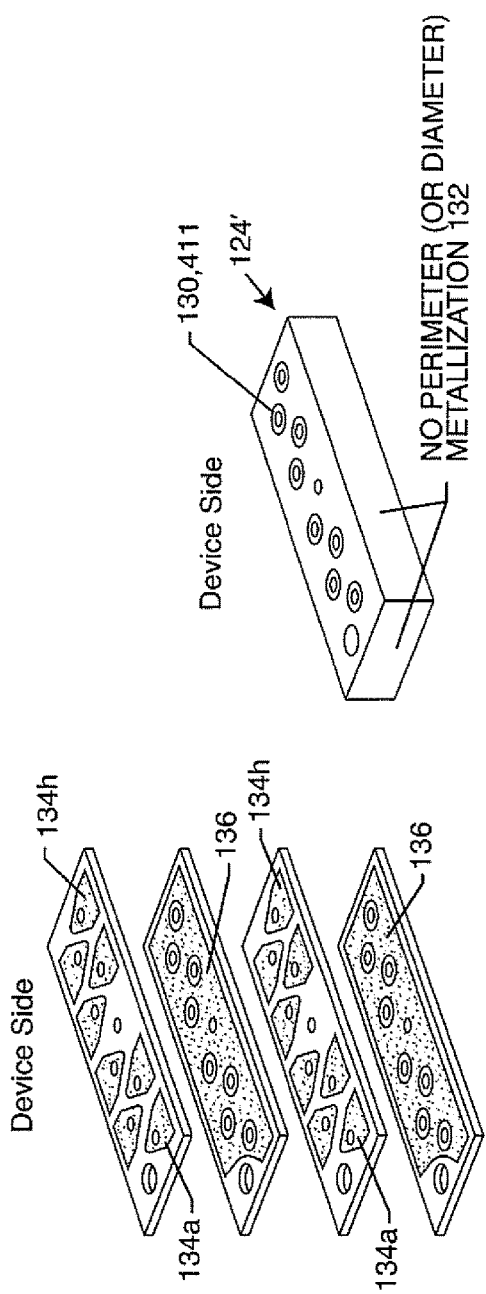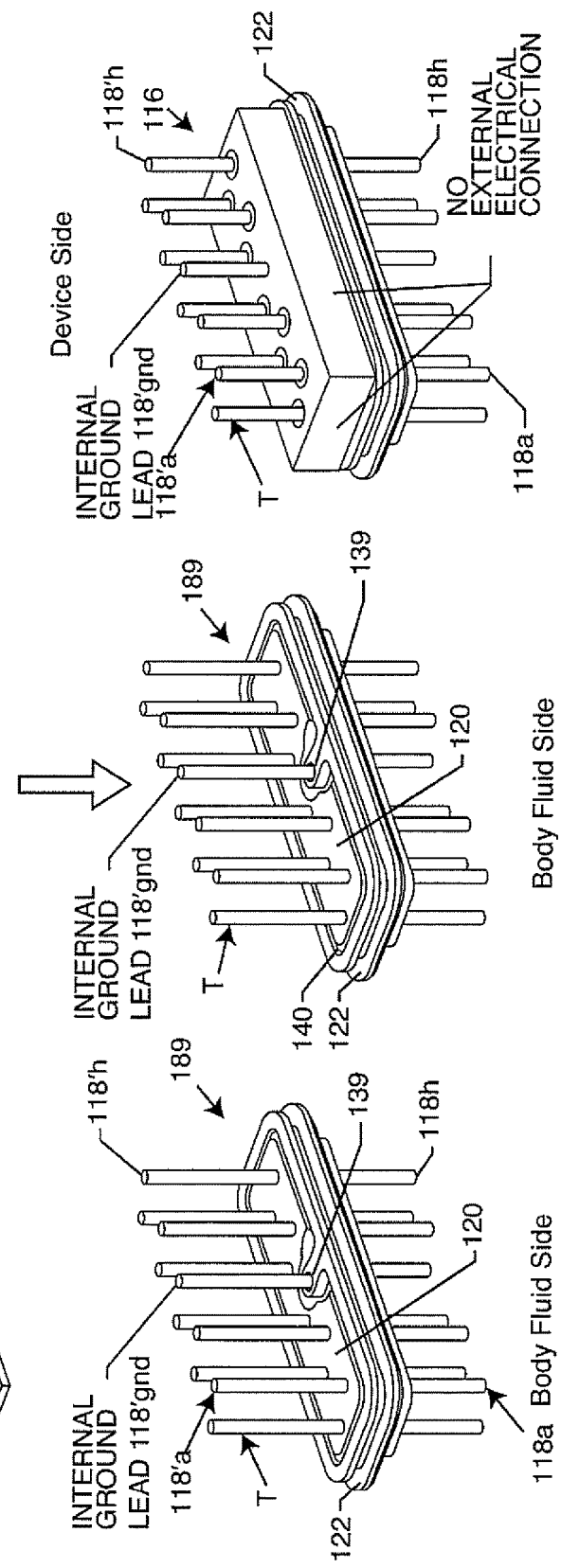
FIG. 13A PRIOR ART
FIG. 13B PRIOR ART
FIG. 13C PRIOR ART

ESR = resistive losses (R) plus dielctric losses (DL)

FLAT-THRU

X2Y

X2Y

X2Y

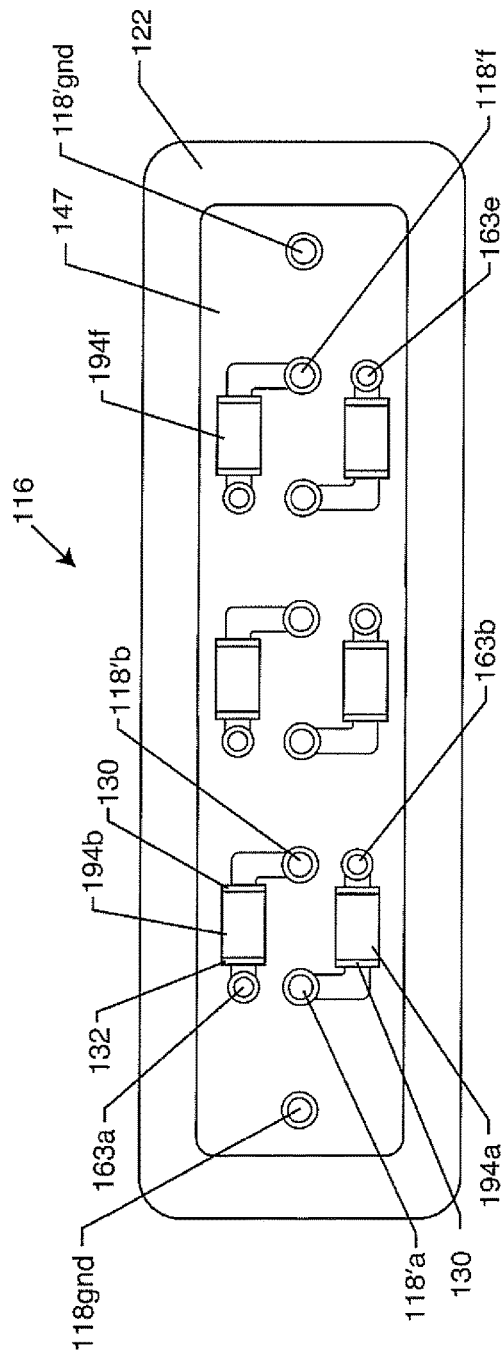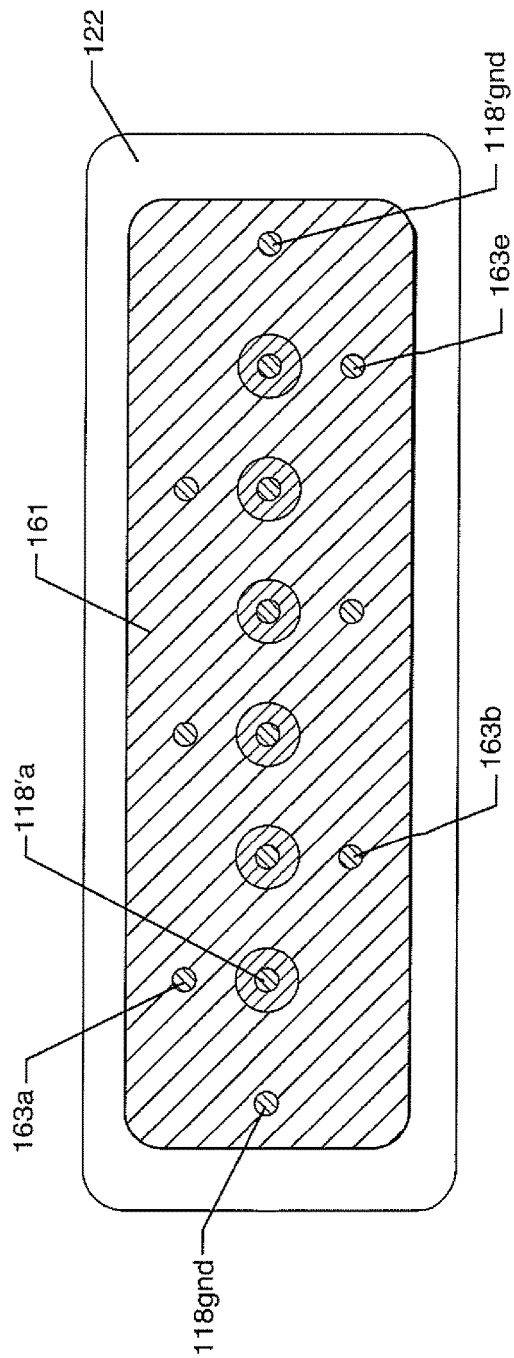

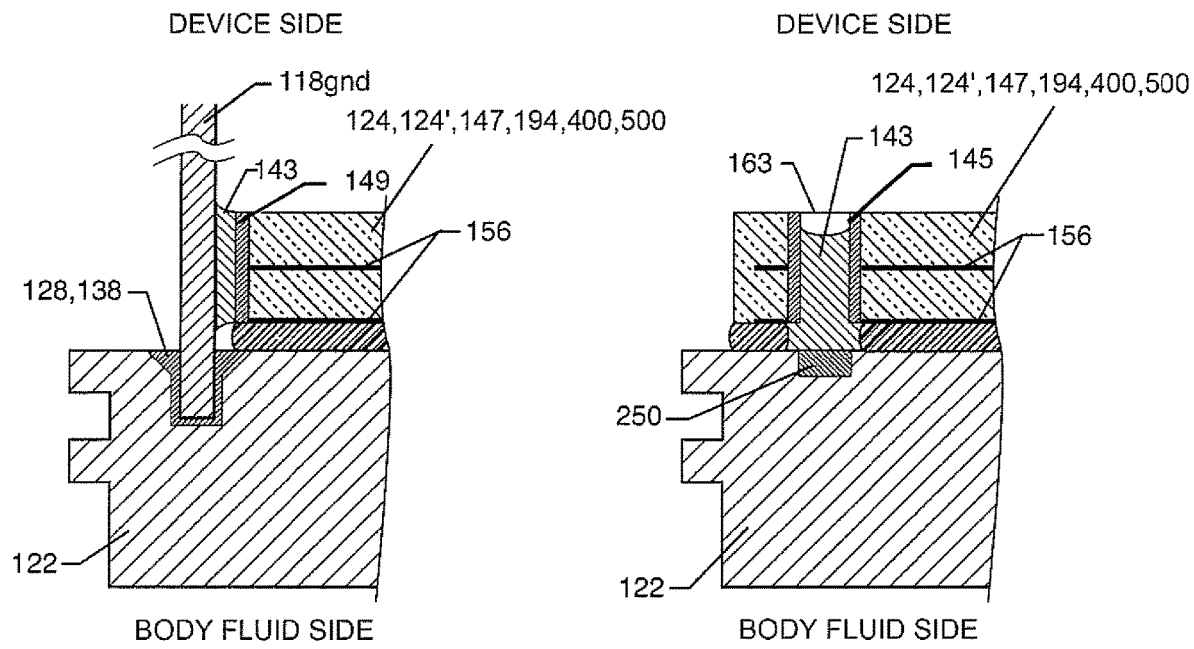
FIG. 23G
PRIOR ART
FIG. 23H
PRIOR ART
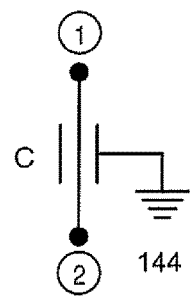
FIG. 23I
PRIOR ART

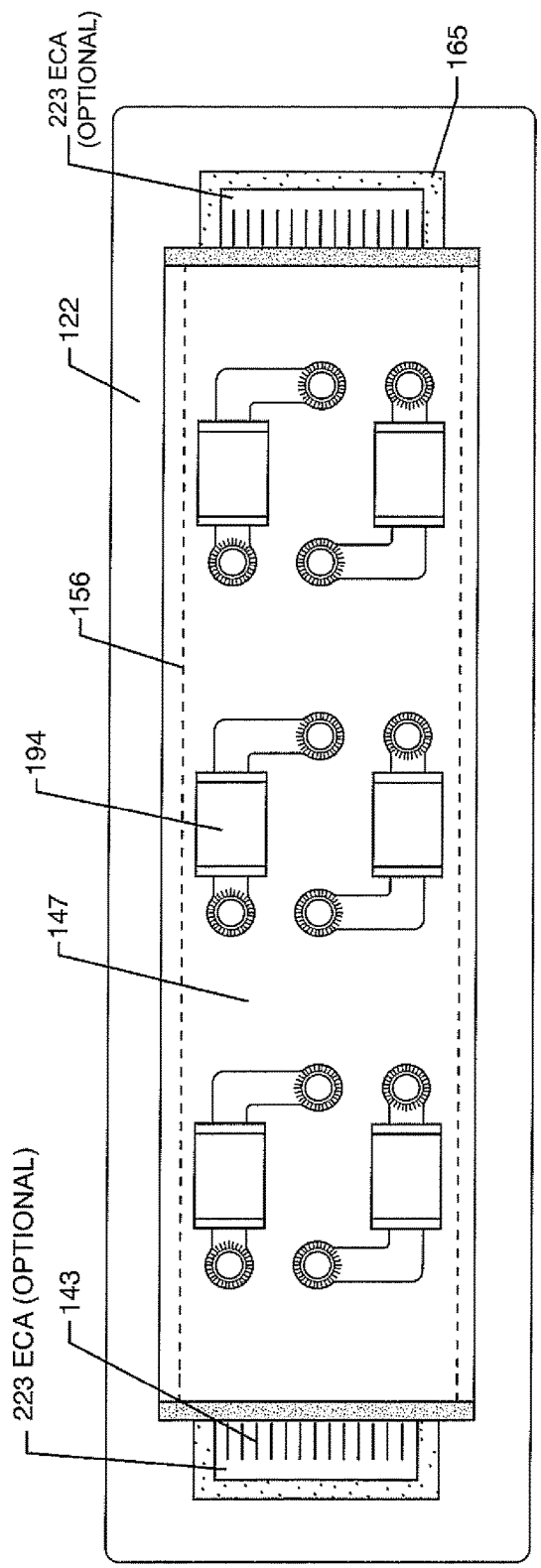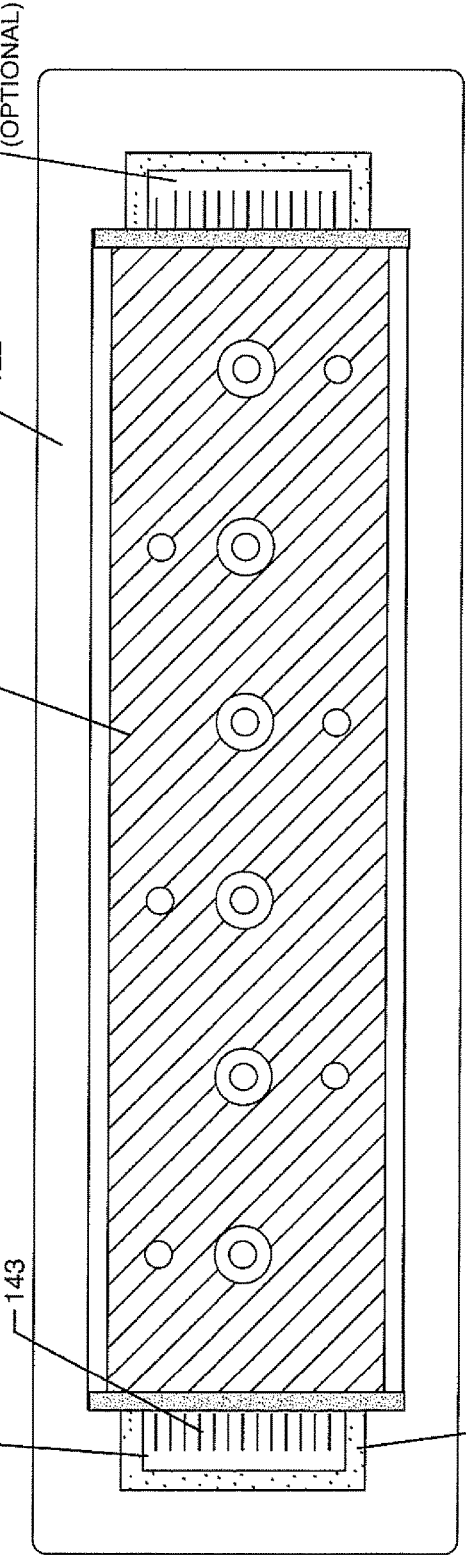

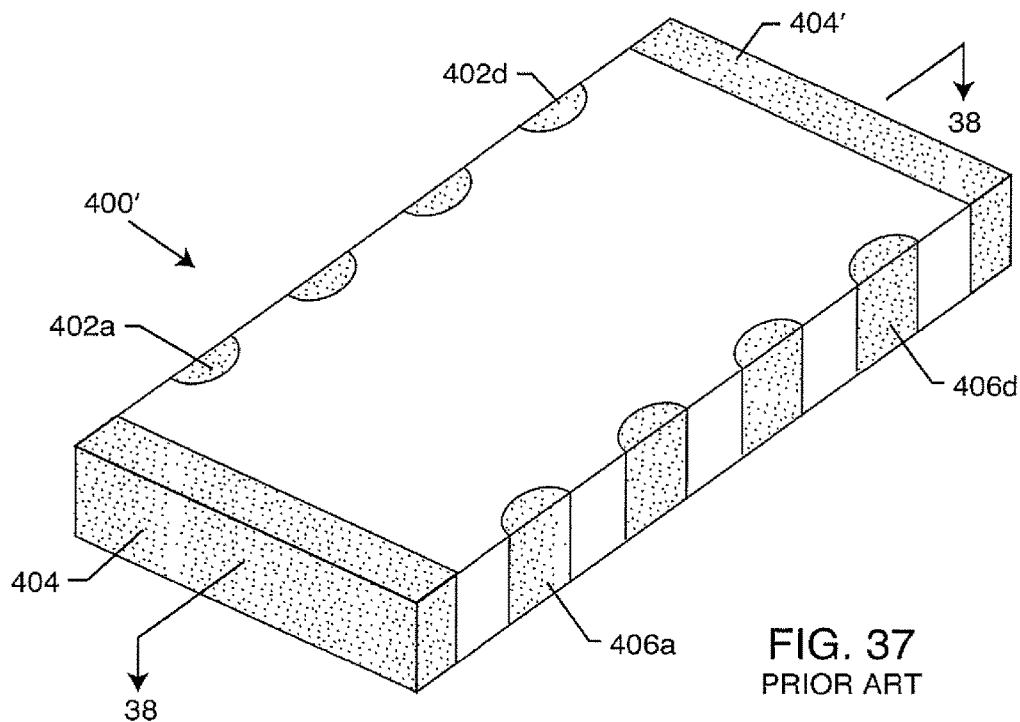
FIG. 37
PRIOR ART
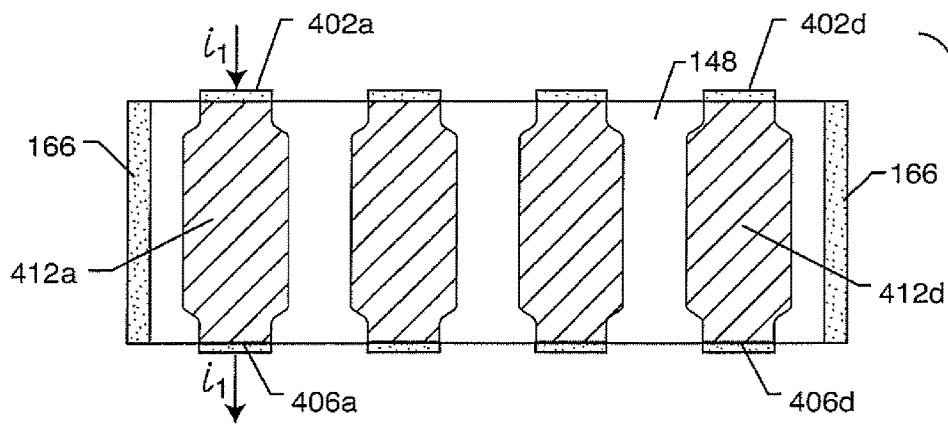
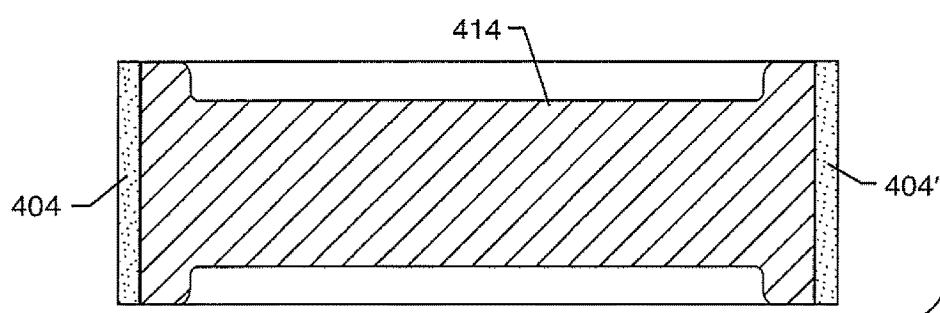
FIG. 38

X2Y
PRIOR ART

| MLCC EMI FILTER CIRCUIT BOARDS AND FEEDTHROUGH FILTER CAPACITORS INCLUDING LOW IMPEDANCE LOW RESISTANCE OXIDE-FREE ELECTRICAL CONNECTIONS TO GROUND AND TO THE FERRULE | | | | CIED FILTER CAPACITORS MADE WITH DIELECTRICS k<1000 & k<200 | HERMETIC SEAL CO-SINTERED PASTE-FILLED VIAS |
|---|---|---|---|---|---|
| 10,912,945 | 9,295,828 | 8,761,895 | 8,301,243 | 7,310,216 | 10,596,369 | 10,561,837 |
| 10,874,866 | 9,251,960 | 8,751,013 | 8,272,466 | 7,199,995 | 10,561,837 | 10,559,409 |
| 10,857,369 | 9,248,283 | 8,712,544 | 8,244,370 | 7,113,387 | 10,559,409 | 10,500,402 |
| 10,828,498 | 9,119,968 | 8,670,841 | 8,195,295 | 7,038,900 | 10,272,253 | 10,420,949 |
| 10,625,084 | 9,071,221 | 8,660,645 | 8,180,448 | 7,035,076 | 10,249,415 | 10,272,253 |
| 10,589,107 | 9,042,999 | 8,659,870 | 8,160,705 | 6,999,818 | 10,092,749 | 10,272,252 |
| 10,449,375 | 9,037,258 | 8,649,857 | 8,145,324 | 6,985,347 | 9,764,129 | 10,249,415 |
| 10,350,421 | 9,031,670 | 8,577,453 | 8,116,862 | 6,888,715 | 9,757,558 | 10,046,166 |
| 10,249,415 | 9,008,799 | 8,509,913 | 8,095,224 | 6,882,248 | 9,014,808 | 9,889,306 |
| 10,124,164 | 9,002,471 | 8,483,840 | 7,966,075 | 6,765,780 | 8,855,768 | 9,511,220 |
| 10,099,051 | 8,996,126 | 8,463,375 | 7,957,806 | 6,765,779 | | 9,492,659 |
| 10,080,889 | 8,977,355 | 8,457,760 | 7,945,322 | 6,567,259 | | 9,463,329 |
| 10,016,596 | 8,918,189 | 8,447,414 | 7,917,219 | 6,566,978 | | 9,352,150 |
| 10,016,595 | 8,903,505 | 8,437,865 | 7,853,324 | 6,529,103 | | 9,233,253 |
| 9,993,650 | 8,897,887 | 8,433,410 | 7,765,005 | 6,456,481 | | 8,938,309 |
| 9,931,514 | 8,868,189 | 8,422,195 | 7,702,387 | RE46,699 | | RE47,624 |
| 9,895,534 | 8,855,785 | 8,364,283 | 7,623,335 | RE48348 | | |
| 9,427,596 | 8,855,768 | 8,321,032 | 7,535,693 | | | |
| 9,312,075 | 8,788,057 | 8,311,628 | 7,489,495 | | | |

FIG. 47

ELECTRICALLY CONDUCTIVE COATING APPLIED TO AN OXIDIZABLE SURFACE OF AN AIMD FERRULE OR HOUSING TO PROVIDE AN OXIDE-RESISTANT CONNECTION TO AN EMI FILTER CAPACITOR, AN EMI FILTER CIRCUIT OR AIMD ELECTRONIC CIRCUITS AND COMPONENTS

CROSS REFERENCE TO RELATED APPLICATIONS

The present application claims priority to U.S. provisional application Ser. No. 63/021,858, filed May 8, 2020. The present application is also a continuation-in-part of U.S. application Ser. No. 17/181,416, filed on Feb. 22, 2021 The contents of all the above applications are fully incorporated herein by these references.

FIELD OF THE INVENTION

The present invention generally relates to oxide-resistant electrical surface coatings, which provide time and temperature stable low resistance electrical ground connections (EGC) for active implantable medical devices (AIMDs). More particularly, the present invention relates to oxide-resistant low resistance low impedance and stable surface coatings and electrical connections to an oxidizable surface, such as a titanium AIMD housing or a titanium ferrule of an AIMD hermetic feedthrough. The stable oxide-resistant and low resistance low impedance electrical connection comprises an oxide-resistant coating of one or more coating layers, which provides resilient and reliable electrical connections for EMI filters, EMI filter circuit boards, AIMD active electronics, AIMD circuit boards, and electrical circuits, components or assemblies.

BACKGROUND

Most present day active implantable medical devices (AIMDs) have one or more electronic circuits enclosed in a hermetically sealed conductive housing (also called a casing). Common prior art AIMDs, including cardiac pacemakers and implantable defibrillators, have a housing that is oxidizable, for example, made of titanium or a titanium alloy. Titanium and titanium alloys are used in medical implants because they are biocompatible and exhibit physical and mechanical properties superior to many other metals. The oxides of titanium are what make titanium biocompatible. For example, titanium exhibits excellent corrosion resistance because, when titanium comes in contact with oxygen or water, instead of corroding (oxidizing), titanium produces an oxide on its surface, which gets stronger over time, constantly enhancing its resilience against corrosive agents (including, human body fluids). Few substances can breach or even damage this protective titanium oxide film, and even if the titanium oxide film is mechanically removed, the oxide film almost immediately regenerates. As such, due to its biocompatibility and biostability, titanium or one of its alloys is largely the material of choice for medical applications, including AIMDs.

It is important to ensure that AIMD's are safe and that they effectively perform without undergoing unacceptable degradation, disruption and/or malfunction caused by inadequate electromagnetic compatibility (EMC). AIMD degradation, disruption and/or malfunction can be caused by unintentional reception and propagation of electromagnetic interference (EMI) or any other electromagnetic energy disturbance, including radio waves, power surges, radio-frequency (RF) disturbances, electrostatic discharge (ESD), among others. A particular concern for patients with AIMDs are EMI induced currents in the electrically conductive metal housing, the therapy leads and/or the lead electrodes of the AIMD during an MRI scan as a result of the pulsed RF field from the scanner's transmit coil and/or the scanner's switched gradient fields; these induced currents can disrupt AIMD electronic circuits and can also heat up the surrounding tissue to dangerous levels. Hence, EMI, or any other electromagnetic energy disturbance, can and does cause undesirable and unwanted effects, including physical damage to not only the AIMD but also to any other operational device or equipment if they are not electromagnetically compatible. For resistance to EMI and EMC, it is typical that devices and equipment, particularly AIMDs, comprise one or more passive EMI filters at or near a leadwire or a hermetic seal conductor point of ingress or egress into the interior of the AIMD housing, which for the exemplary EMI filter is usually disposed inside the AIMD hermetically sealed housing. It is noted that, throughout this application, the AIMD serves as a non-limiting exemplar for the disclosed teachings. AIMD is a general term used for medical devices that rely on electrical energy or any source of power including external sources, energy harvesting by motions, or chemical processes, other than that directly generated by the human body or gravity. Additionally, for particular teachings disclosed herein, a cardiovascular implantable electronic device (CIED) serves as the non-limiting exemplar, the CIED being a specific class of AIMD that addresses cardiac rhythm management (CRM) anomalies.

In general, AIMDs comprise hermetically sealed feedthroughs or feedthrough subassemblies, which are typically part of the AIMD construction. A hermetically sealed feedthrough or feedthrough subassembly is commonly located at the point of ingress into the AIMD housing and typically comprises a metallic ferrule, such as titanium, and an insulator, such as an alumina ceramic, a glass, or a glass-ceramic. One or more electrical conductors, comprising leadwires, terminal pins, co-sintered vias, and the like, pass through the insulator in non-conductive relationship with the ferrule and are hermetically sealed to the insulator. The insulator is also hermetically sealed to the ferrule. It is noted that the metallic ferrule may be a separate component from the housing of the AIMD or may be formed as an integral part of the housing itself. The insulator comprising the hermetically sealed electrical conductors may alternatively be directly sealed to the AIMD housing. The AIMD EMI (and/or MRI) filters divert undesirable EMI signals coupled to an implanted lead to the AIMD housing where the coupled signals are harmlessly dissipated as a few milliwatts of heat energy. Thus, dangerous EMI and/or RF energy is prevented from entering into the housing of the AIMD where it can disrupt the proper operation of biological sensing or therapy delivery circuits. It is important to note that, in addition to AIMDs, the present invention is further applicable to leadless devices such as implantable loop recorders, monitors, leadless pacemakers, sensors, telemetry antennas, RFID antennas and the like.

Regarding AIMD manufacturing, when the ferrule of a hermetically sealed feedthrough is laser welded into the opening of the AIMD housing, the laser welding process generates a great deal of localized heat, which leads to a thickening of titanium surface oxides on the ferrule. Likewise, when the AIMD housing is laser welded to hermetically seal the pulse generator (PG), titanium oxides form about the weld seam, including the weld seam at or near the location of the hermetically sealed feedthrough. Such oxide formation and thickening makes electrical connection of electrical and electronic components, such as a filter, a filter circuit board, an AIMD active filter, or an AIMD active circuit board, to the oxidized surface of the feedthrough ferrule or the AIMD housing very challenging. For an EMI and an MRI filter to work properly, the electrical connection of the filter to a system ground point or surface, especially a titanium surface of an AIMD, must have a very low equivalent series resistance (ESR) so that a maximum amount of EMI energy is dissipated (filtered) by the filter to the AIMD housing; thus, the EMI or RF energy is prevented from entering into the inside of the AIMD housing, where such energy can cause undesirable, even dangerous and life-threatening, device therapy delivery issues [a particular concern for cardiac implantable electronic devices (CIEDs)]. The AIMD housing, which is thermally and electrically conductive (and, as previously disclosed, generally of titanium), provides both an EMI shield and a hermetic seal to the AIMD. High frequency energy, such as that from microwave ovens, is reflected and absorbed by this titanium housing or shield. In addition, EMI filters intercept undesirable signals that are coupled to or radiated onto AIMD implanted leads (which act as antennas) and divert such undesirable signals to the titanium housing, thereby preventing entry into the AIMD electronics.

Referring once again to titanium and EMI diversion, it is the excellent corrosion resistance and biocompatibility of titanium that, as stated earlier, causes concern regarding the efficacy of EMI filter electrical connections. Further to titanium's stability in the presence of human body fluids, it is understood by one skilled in the art that titanium's excellent corrosion resistance is due to the formation of a thermodynamically stable, continuous, highly adherent, and protective surface oxide film. Since titanium metal is highly reactive and has an extremely high affinity for oxygen, this surface oxide film is formed spontaneously and instantly when a fresh titanium metal surface is exposed to air and/or moisture (even at room temperature). In fact, a damaged titanium oxide film can generally re-heal itself instantaneously if even at least traces (that is, a few parts per million) of oxygen or water are present in the environment. Researchers have proven that within a millisecond of exposure of titanium to air, a 10 nm titanium oxide layer will be formed on the exposed titanium metal. This titanium oxide layer will grow to about 100 nm thick within a minute. While a titanium oxide layer on the highly reactive titanium metal surface imparts good corrosion resistance and provides high biocompatibility and biostability as noted, the inventors have personally observed that is it for this very reason that such a titanium oxide layer can and does undesirably impact AIMD EMI filter performance. The inventors further note that, besides affecting EMI filters, the undesirable impact of electrically connecting critical electronic components to an oxidized surface is even more observable at higher frequency applications, such as, but not limited to, switching applications, coupling applications, and bypass applications; hence, the inventors maintain that electrical connection to either an oxidizable surface or an already-oxidized surface is to be completely avoided, particularly in AIMDs intended for patients dependent on the electrical therapy being delivered by that AIMD. As an illustration, EMI inside a pacemaker can lead to improper therapy or even complete inhibition of therapy, which, for a pacemaker dependent patient, is immediately life-threatening, as the patient's heart does not beat unless the pacemaker stimulates that heart to do so; or, EMI that enters a deep brain stimulator that senses brain activity can miss identifying an epileptic event, consequently does not deliver the therapy required to prevent an oncoming seizure. For an epileptic patient licensed to drive a motor vehicle, prevention of therapy can lead to a car accident endangering, even killing, the patient and/or others involved in that accident.

Prior practice addresses oxidation layers on metals by cleaning the surface of a metal component. Prior practice also specifically addresses titanium oxide removal by cleaning a titanium surface using various means. There is even prior practice, for example, regarding disposing a stripe of a thermal-setting electrically conductive adhesive (ECA), that is, an ECA stripe, atop a "cleaned" titanium surface, such as, a titanium feedthrough ferrule or a titanium AIMD housing. The problem with this ECA stripe approach is that (1) the ECA stripe must be cured at an elevated temperature of between 200° C. and 300° C.; and (2) the housing must be laser welded to hermetically seal the AIMD, both of which drive outgassing processes from the ECA itself and/or volatilization of any residues or impurities remaining on the "cleaned" titanium surface.

With respect to curing, it is important to note that, if the ECA stripe is cured in air, the titanium oxide, which is initially cleaned from the titanium surface of the exemplar feedthrough ferrule or AIMD housing, almost immediately reforms due to the presence of oxygen in the air. Even curing an ECA stripe in an inert atmosphere or a vacuum is not effective, as only a few parts per million of oxygen or water vapor in the curing process environment re-oxidizes the titanium metal. In other words, because of titanium's high affinity for oxygen, despite cleaning the oxides from the titanium and/or even making the best attempts to minimize oxygen and water vapor from the curing process, there is still a titanium oxide layer present between the ECA and the titanium surface. Furthermore, while the oxide layer may initially materialize as a thin oxide layer, because of this same affinity of titanium for oxygen, an oxide layer on a titanium surface will insidiously continue to thicken over time. It is the thickening of the titanium oxides over time that is of most concern, as such oxide thickening can and does cause latent, unpredictable, and dangerous AIMD EMI filter performance issues, including failure to filter EMI. What is even worse is that the AIMD industry generally believes that, once the AIMD components are hermetically sealed within the housing of an AIMD, oxide layers will not form on any titanium components enclosed within this AIMD housing simply because the AIMD is typically assembled in an inert atmosphere, such as helium, nitrogen or argon gases and/or the AIMD may also optionally be back-filled with one of these gases. This belief is not only flawed but also alarming, as components enclosed within the AIMD housing comprise other materials in addition to the ECA stripe, such as polymers, plastics, adhesives, elastomers and printed circuit boards (PCBs), all of which generally have some level of oxygen-containing gases, vapors and/or impurities trapped within their structure (for example, undetected organic and/or oxygen-containing residues, moisture, oxygen and other oxygen-containing gases and/or vapors) that eventually outgas or volatilize during the operating life of the AIMD.

Similarly, when the housing of the pulse generator of the AIMD is laser welded, a temperature rise in the surrounding area results. The laser weld, which is typically in close proximity of the prior practice EMI filter ground ECA stripe, can thereby directly cause additional titanium oxide formation between the cured ECA stripe and the initially cleaned but re-oxidized titanium due to further outgassing of the ECA stripe, which is now exposed to yet another temperature rise. Furthermore, at this stage of manufacturing, all of the internal components are housed within the PG, many of which do include oxygen-containing materials, such as, the AMD electronic circuit components, circuit boards, various coatings (metallic, composite, polymeric or elastomeric), conformal coatings, adhesives, sealants, rubbers, epoxies, and combinations thereof. Hence, the elevated temperature due to laser welding drives an additional release, outgassing or volatilization of oxygen from such oxygen-containing constituents, including any remaining residues or impurities introduced on any surface inside the AIMD during one or more steps in the AIMD PG assembly process. Likewise, AIMDs can be subjected to elevated temperatures during other manufacturing processes besides laser welding, or even during shipping, which can cause significant temperature shifts, further driving outgassing or volatilization. More importantly, this additional outgassing and volatilization causes undesirable and dangerous thickening of the titanium oxide layer previously formed during the ECA curing process. Thus, as a result of the AIMD assembly and manufacturing processes, the equivalent series resistance (ESR) of the EMI filter can and does dangerously increase to considerably compromise EMI filtering and can even cause complete EMI filter failure (meaning, undesirable and unwanted EMI enters directly inside of the housing of the AIMD). Such potentially unsafe ESR increases are particularly observable at frequencies above 10 MHz. More importantly, and of most concern, is that the unsafe ESR increases (in other words, EMI capacitor ohmic losses) are often masked (essentially, totally hidden and indistinguishable) at low frequencies by the EMI filter's dielectric losses. Such masking is particularly egregious to present day CIEDs, such as pacemakers and implantable cardioverter-defibrillators, which are often qualified and labelled "MRI Conditionally Approved". EMI filters in an MRI environment are added to AIMD devices specifically to divert substantial and potentially dangerous RF current. The RF current is generated in the implanted AIMD therapy delivery leads during MRI. The EMI filters installed in the AIMD then diverts the RF current to the AIMD housing for dissipation. Hence, reliance solely on ECA stripe attachment to an oxidizable metal surface, such as a titanium surface, is considered by the inventors to be dangerous and of poor practice.

Further regarding the particular observance of ESR increases at frequencies above 10 MHz, it is important to note that, since the formation of oxide layers on electrically conductive surfaces unfavorably increase an RF ground impedance, which in turn can significantly increase the ESR of a filter capacitor, it specifically is the formed oxide layers that dangerously degrade EMI filtering performance [insertion loss (IL) in dB]. Hence, it is recommended that qualification testing of all AIMD EMI filter designs include both ESR and IL measurements so that acceptable EMI filter performance can be established for a capacitor qualification lot. ESR measurements is made above 10 MHz and, in particular, at 64 MHz (MRI RF pulsed frequency of a 1.5T scanner). ESR measurements during initial design qualification can be conducted with swept measurements from 1 MHz to 500 MHz using a materials analyzer. Each measured capacitor ESR can then be overlayed atop (and compared with) a characteristic U-shaped composite reference ESR curve (that of an ideal filter capacitor). An ESR curve represents the summation of a capacitor's ohmic loss. At frequencies above the point where the dielectric loss tangent exponentially goes to zero (about 10 MHz to 20 MHz for a ceramic dielectric with a dielectric constant of about 2000 to 3000), the ESR curve represents the summation of a capacitor's ohmic losses. A capacitor's ohmic losses includes the total resistance of all the capacitor electrodes, the electrical attachment materials, the capacitor metallization, and the electrical connection material. High frequency capacitors, such as MRI filter capacitors, are designed so that the center of their U-shaped curve falls in the range of the MRI RF-pulsed frequencies of the characteristic U-shaped composite reference ESR curve, for example, 64 MHz (1.5T MRI scanner) and/or 128 MHz (3T MRI scanner). A properly designed MRI filter demonstrates a capacitor ESR ohmic loss that is relatively constant from a low frequency to very high frequencies. Thus, an overlay comparison with the reference ESR curve of an ideal capacitor can be made for each qualification part, providing a fingerprint representative of the electrical ground connection (EGC). In addition, during design qualification, IL can also be made on a network analyzer using frequency sweeps (in dB) from 10 MHz to 3000 MHz, including 64 MHz and 128 MHz. For more detail referring to the effects of oxide layer formation on EMI filtering, refer to the paper entitled, "Dissipation Factor Testing is Inadequate for Medical Implant EMI Filters and Other High Frequency MLC Capacitor Applications", ISSN: 0887-7491, presented at CARTS 2003: 23rd Capacitor and Resistor Technology Symposium, Mar. 31-Apr. 3, 2003, incorporated herein by this reference.

In summary, the inventors found that even if an AIMD is manufactured in an inert gas environment, or backfilled with an inert gas, such 'heating' of certain materials of construction can and do release oxygen, oxygen-containing gases or water vapor into an otherwise hermetically sealed environment, causing the formation and/or thickening of existent oxide layers on oxidizable surfaces, such as titanium surfaces. The formation and/or thickening of such oxide layers can dangerously compromise EMI filter performance and/or increase electrical connection resistance to a level, wherein the electrical connection severely limits intended performance of a component, an assembly or the AIMD itself or may even cause complete component, assembly or AIMD device performance failure. Of particular concern is complete failure of a device's system ground, as one skilled in the art understands that the electrical connection of, for example, passive EMI filters to the system ground of the AIMD must be a very low impedance connection to properly function. As such, any substantial titanium oxides on any system electrical ground connection surface that can and will compromise filter performance are not only undesirable but also not allowable.

Further regarding an EMI filter capacitor's system electrical ground connection and thermal exposure, the inventors also found that, during qualification, it is very important to first characterize and carefully measure the ESR of each filter capacitor in a qualification lot and then expose each filter capacitor to thermal shock, including the very substantial thermal shock associated with laser welding of the hermetically sealed filter feedthrough assembly into an AIMD housing. In general, laser weld thermal exposure will be the worse thermal and mechanical insult that a filter capacitor will see, including the filter capacitor's very important system electrical ground connection either to the feedthrough ferrule or to the AIMD housing. Repeating precision ESR insertion loss measurements after thermal shock, particularly after this worse case laser weld "thermal insult", is critically important in order to make sure that no dangerous oxides have been formed during AIMD assembly and manufacturing. In other words, before and after thermal exposure by laser welding, it is important that the filter capacitor ESR and insertion loss plots still overlay like a fingerprint (i.e., are essentially the same pre and post thermal exposure).

The inventors also learned that laser welding the feedthrough ferrule of a hermetically sealed filter feedthrough assembly (comprising a filter capacitor attached to a hermetic feedthrough) into the opening of the AIMD housing, can sometimes require laser weld rework due to hermetic seal leakage or cosmetic defects. This means that, during laser welding, instead of one or two high temperature laser weld passes around the ferrule, additional laser weld passes may be performed until the ferrule hermetic seal laser weld passes leak rate and cosmetic requirements. Accordingly, during design qualification, one must carefully record both ESR and IL before and after laser welding, including all the multiple laser reworks. It is important to emphasize that the ESR and IL curves vs. frequency must not change significantly (for ESR at MRI RF pulsed frequencies, the ESR must not increase by more than 10%; for insertion loss, at MRI frequencies the insertion loss shall not decrease after laser welding by more than 1 dB).

For AIMDs, there are two types of electronic components: passive components and active components. Passive components do not require a source of energy and include capacitors, resistors and inductors. Active components do require an energy source and include microelectronic chips, microprocessors, ASIC electronics and the like. For AIMDs, energy sources are typically either a primary or a secondary battery. However, AIMD energy sources can be coupled energy sources through either inductive or wireless charging, energy harvesting (for example, by motion of the myocardium) or even a captured ultrasonic induced energy.

Accordingly, there is a need for a low resistance low impedance and stable electrical connection having an electrically conductive oxide-resistant layer to electrically connect an electrical component of an active implantable medical device, wherein the electrical component is one of an EMI filter, an EMI filter circuit board, a sensor, AIMD circuitry, an AIMD circuit board, and combinations thereof. There is also a need for a low resistance low impedance and stable electrical connection having an electrically conductive oxide-resistant layer to electrically connect other AIMD electrical connections, separable connectors, switches and relays, metallizations, circuits, sensors, RFID chips and assemblies, and device antennas including AIMD telemetry or RFID antennas. There is also yet a further need for a low resistance low impedance and stable electrical connection having an electrically conductive oxide-resistant layer to electrically connect electrical components, terminals, leads, leadwires, pins, lead frame for electronic and telecommunication applications, all these components, assemblies, devices, systems and applications.

SUMMARY OF THE INVENTION

The present application discloses an oxide-resistant coating or layer residing on an oxidizable electrically conductive surface, which has been either mechanically, chemically, electrochemically, plasma, brush, or grit blast cleaned of all surface oxides. The present application further discloses an oxide-resistant electrical connection to an electrical terminal of an apparatus and to an oxide-resistant layer supported on an oxidizable electrically conductive surface of the apparatus. More specifically, the present invention provides a structure and methods of manufacture of an oxide-resistant layer residing on an oxidizable electrically conductive surface, wherein the oxidizable electrically conductive surface is selected from the group consisting of: a hermetic feedthrough ferrule surface, an AIMD housing surface, a medical device housing surface, a feedthrough terminal pin surface, a feedthrough pin surface, a feedthrough leadwire surface, a feedthrough lead wire surface, a feedthrough two-part pin surface, a feedthrough lead conductor surface, a surface of a metallic insert of a sintered or co-sintered paste-filled feedthrough via, a ferrule terminal pin surface, a ferrule pin surface, a ferrule leadwire surface, a ferrule lead wire surface, a ferrule two-part pin surface, a ferrule lead conductor surface, a surface of a metallic insert of a sintered or co-sintered ferrule paste-filled via, or combinations thereof. The oxide-resistant electrical connection of the present application provides low impedance, low resistance and very stable electrical connection to EMI filters, EMI filter circuit boards, sensors, AIMD circuitry, AIMD circuit boards and combinations thereof. The oxide-resistant electrical connection may further comprise one an active electrical component, a passive electrical component, and both active and passive components. The oxide-resistant electrical connection may include feedthrough capacitors, internally grounded feedthrough capacitors, MLCC filter circuit boards, X2Y attenuators, flat-thru capacitors, internal electronic components, AIMD active circuit boards and circuit board electrical components and circuitry. The low impedance low resistance and stable electrical connection may comprise an electrical system ground connection, an active electrical connection, or both electrical system ground and active electrical connections.

As previously disclosed, titanium and titanium alloys are considered desirable metallic materials for biomedical applications due to their biocompatibility, high strength, low mass and corrosion resistance. For example, present day active implantable medical devices (AIMD) typically comprise a thin hermetically sealed housing made of commercially pure titanium. Alternatively, titanium-based alloys comprising gold, platinum, niobium, palladium, tantalum, aluminum, vanadium, molybdenum, zirconium, iron, hafnium, indium chromium, silicon, tin, and combinations thereof. Table 1 below provides non-limiting exemplary commercially pure titanium and various titanium alloys used in implants.

TABLE 1

| Titanium or Alloy | ASTM Grade | UNS | ASTM | ISO | Type |
|---|---|---|---|---|---|
| Ti CP4 | Gr 1 | R50250 | ASTM F 67 | ISO 5832-2 | commercially pure Ti |
| Ti CP3 | Gr 2 | R50400 | ASTM F 67 | ISO 5832-2 | commercially pure Ti |
| Ti CP2 | Gr 3 | R50550 | ASTM F 67 | ISO 5832-2 | commercially pure Ti |
| Ti CP1 | Gr 4 | R50700 | ASTM F 67 | ISO 5832-2 | commercially pure Ti |
| Ti-3Al-2.5V | Gr 9 | R56320 | ASTM B 265 | | $\alpha + \beta$ alloy |
| Ti-5Al-2.5Fe | | | | ISO 5832-10 | $\alpha + \beta$ alloy |
| Ti-6Al-4V | Gr 5 | R56400 | ASTM F 1472 | ISO 5832-3 | $\alpha + \beta$ alloy |
| Ti-6Al-4V ELI | Gr 23 | R56401 | ASTM F 136 | ISO 5832-3 | $\alpha + \beta$ alloy |

TABLE 1-continued

| Titanium or Alloy | ASTM Grade | UNS | ASTM | ISO | Type |
|---|---|---|---|---|---|
| TI-6Al-7Nb | | R56700 | ASTM F 1295 | ISO 5832-11 | α + β alloy |
| Ti-15Mo | | R58150 | ASTM F 2066 | | β alloy |
| Ti-13Nb-13Zr | | R58130 | ASTM F 1713 | | β alloy |
| Ti-12Mo-6Zr-2Fe | | R58120 | ASTM F 1813 | | β alloy |
| T1-45Nb | Gr 36 | R58450 | AMS 4982 | | β alloy |
| Ti-35Nb-7Zr-5Ta | | R58350 | | | β alloy |
| Ti-55.8Ni | | | ASTM F 2063 | | metallic compound |
| Ti-15Mo-xW | | | | | x ranges 3 to 15 |
| Ti-Mo alloys | | | | | plus Si, Zr, Ta, W, Mn or combinations thereof |

AIMDs generally have hermetically sealed feedthroughs that comprise feedthrough conductive pathways, the feedthrough conductive pathways comprising electrical conductors that pass through the insulator of the hermetically sealed feedthrough to the body fluid side and to the device side of the AIMD. As defined herein, the body fluid side of an AIMD is the exterior or the outside of a hermetically sealed housing of an AIMD. The hermetically sealed housing of the AIMD is also known as an implantable pulse generator, an IPG, a pulse generator, or a PG. Any components residing on the outside of the hermetically sealed housing are on the body fluid side of the AIMD (e.g., a header block, therapy delivery leads, among others), and must comprise stable, biocompatible, and nontoxic materials. The device side of the AIMD is defined herein as the interior or the inside of a hermetically sealed housing of an AIMD. The interior or inside of a hermetically sealed housing is also known as an inboard side of the AIMD. Any components or electronic circuits sealed within the hermetically sealed housing (e.g., an AIMD active electronic circuit board and a power source, such as a battery and/or a capacitor, among others) are on the device side of the AIMD, and thereby are protected from damaging body fluids, therefore, may comprise any materials appropriate for that specific device. The hermetically sealed feedthroughs of an AIMD generally comprise an insulator through which electrical conductors pass. The electrical conductor passing through the hermetically sealed feedthrough is defined herein as a "conductive pathway". A hermetic conductive pathway is formed in the feedthrough during a high temperature sealing process. The hermetically sealed feedthrough conductive pathway may be selected from the group consisting of a terminal pin, a pin, a leadwire, a lead wire, a two-part pin, a lead conductor, a sintered paste-filled via, a co-sintered via, a co-sintered paste-filled via, a co-sintered via with one or more metallic inserts, or combinations thereof. Each hermetically sealed feedthrough conductive pathway may comprise the same embodiment for all feedthrough conductive pathways of the hermetically sealed feedthrough, or, alternatively, may comprise one or more different feedthrough conductive pathway embodiments of the total feedthrough conductive pathways present in the hermetically sealed feedthrough. The hermetically sealed feedthrough of an AIMD may comprise a glass seal, a glass-ceramic seal, or a ceramic seal.

It is important to note that a hermetically sealed implantable device is required to maintain hermeticity in a variety of harsh environments, such as, but not limited to, environments that exhibit high and low (even cryogenic) temperatures, corrosive conditions (including body fluids), high pressures, high vacuums, or combinations thereof. The industry standard leak rate for AIMD hermeticity is typically tested by a helium (He) mass spectrometer leak detection tester and measured in std cc He/sec. The hermetically sealed feedthrough for a typical CIED comprises a leak rate no greater than $1 \times 10^{-7}$ std cc He/sec. For other types of AIMDs, for example, a cochlear implant or a bion, the leak rate is no greater than $1 \times 10^{-10}$ std cc He/sec. For particularly small packages, such as certain bions, the leak rate is no greater than $1 \times 10^{-2}$ std cc He/sec. Standard leak rates for microelectronic devices with internal cavities are defined by MIL-STD-883. This standard is administered by the United States Department of Defense, Defense Logistics Agency, and is approved for use by all Departments and Agencies of the Department of Defense. The Military and Aerospace sectors have used these standards since the introduction of the base standard, MIL-STD-883, May 1, 1968. Over time these standards have also become a normal part of many other microelectronic sectors including telecommunications and medical device manufacturers. The standard has been updated at least 10 times over the years, with the latest notice of change released in 2016, now MIL-STD-883K. This standard provides for 8 methods for verifying device hermeticity given certain conditions. A maximum He leak rate of a hermetically sealed implantable medical device can be determined by the design size and free volume of that implantable medical device in accordance with METHOD 1014.15 of MIL-STD-883K. The maximum He leak rate of the hermetically sealed implantable medical devices of the present application range from at most $10^{-6}$ std cc He/sec to $\leq 10^{-12}$ std cc He/sec. It is understood by one skilled in the art that $1 \times 10^{-12}$ std cc He/sec is a lower leak rate (in other words, a higher hermeticity level) than $1 \times 10^{-6}$ std cc He/sec (which is a higher leak rate, in other words a lower hermeticity level).

Typically, the hermetically sealed feedthrough of an AIMD comprises a ferrule, which is generally formed from a titanium or titanium alloy metal. The ferrule is typically designed to be laser welded into an opening of a housing of the AIMD. It is noted that the present invention equally applies to hermetic seals for AIMDs that do not comprise a ferrule. For example, hermetically sealed feedthroughs may be formed by sealing directly into a housing, a lid, or a protrusion of the housing or the lid of an AIMD. The protrusion of the housing or the lid of an AIMD provides walls that increase the length of bonding to the insulator of the hermetically sealed feedthrough. The protruding walls are contiguous (one-piece) with the AIMD housing. The protruding walls may be configured as a stress-relieving flange. Shaped stress-relieving flanges are taught in U.S. Pat. No. 6,008,980, the content of which is fully incorporated herein by this reference. Although the housing of an AIMD typically comprises titanium or a titanium alloy, other housing materials may alternatively be used. As such, the housing material of the present invention may be selected from the group consisting of titanium, a titanium alloy, a stainless steel, a ceramic, a metal plated or coated ceramic, a nickel-based superalloy, a cobalt-based superalloy, a nickel-chrome superalloy, a cobalt-chrome superalloy, a biocompatible corrosion-resistant alloy, or combinations thereof.

To assemble an AIMD, the AIMD hybrid circuits (consisting of a microprocessor and electrical components such as resistors, inductors, capacitors, among others) and the power supply (at least a battery, and, in the case of an implantable cardioverter-defibrillator or ICD, a high energy storage capacitor) are placed in the titanium housing (typically ASTM Gr 1) in a specially designed cleanroom compliant with ISO standards such as ISO 14708 (AIMD design and manufacture), ISO 14644 (cleanroom classification) and ISO 13485 (quality management). For example, Class II devices (such as coronary catheters) and Class III devices (such as pacemakers and ICDs) are typically manufactured in Class 8 (also known as Class 100,000 by the cancelled U.S. Fed. Std. 209E) cleanrooms and packaged in Class 7 (also known as Class 10,000 by the U.S. cancelled Fed. Std. 209E) cleanrooms. The cleanrooms are electrostatically controlled (essentially no static charge), atmosphere controlled (less than 1% moisture), and have controlled cleanliness levels (extremely low levels of dust, airborne organisms, or vaporized particles; for example, Class 7 and Class 8 cleanrooms are limited to ≤10,000 and ≤100,000 particles/ft$^3$ respectively for particle sizes≥0.5 μm). Once the AIMD electronic circuits and the power source are in the housing, the housing is hermetically sealed, typically by laser welding, which creates an 'airtight' AIMD. The term "airtight" is defined herein as not allowing the AIMD to leak any material, whether the material is a gas, a liquid, or a solid, from the external environment into the device housing or from inside of the device housing to the external environment. Prior to final hermetic sealing, the AIMD housing is vacuum evacuated then backfilled with an inert gas, which may optionally have some helium added to facilitate fine leak detection. In general, after laser welding, the top or header, which is also known as a header block, is attached to the AMD. For CIEDs and some neurostimulator devices, implantable leads plug into ports of the AIMD header block.

An electrically conductive AIMD housing, for example, a titanium housing, allows patients to safely use appliances such as microwave ovens and cell phones as the AIMD electrically conductive housing is an enclosure, i.e., a container within which the internal components of the AIMD are enclosed, thereby forming a Faraday cage, which shields the internal components of the AIMD from external electric fields and electromagnetic interference (EMI). In addition, the electrically conductive AIMD housing also shields its internal components from ground level cosmic radiation. Moreover, an AIMD housing of, for example, a CIED, is many orders of magnitude higher in surface area than the CIED's distal electrodes; hence, a properly designed and grounded capacitive filter or filter circuit board can effectively pull unwanted and potentially dangerous EMI or MRI RF energy away from an AIMD's distal electrodes and divert the RF energy to this Faraday cage (in other words, to the AIMD housing). Such potentially dangerous EMI or MRI RF energy is then dissipated as circulating currents in the AIMD housing (i.e., the Faraday cage), which results in only a few milliwatts or watts of heat energy. An improperly designed EMI filter or filter circuit board (i.e., a filter having a relatively high ESR) can cause considerable temperature rise in an AIMD housing. In fact, experiments conducted by the inventors in an MRI scanner, demonstrated that an AIMD housing can substantially heat up, dangerously increasing temperature to as much as 12° C. (53.6° F.) above the average human body temperature of 37° C. (98.6° F.); i.e., to a potentially unsafe temperature of 49° C. (120.2° F.).

In contrast, a properly designed EMI filter or filter circuit board in combination with an oxide-free electrical ground connection limits AIMD housing temperature rise to less than 4.5° C. (40.1° F.), a temperature rise to 41.5° C. (106.7° F.). Thermal injury occurs when an increase in the temperature of local human body tissue rises above a certain threshold causing irreversible cellular injury. Experiments conducted by Moritz and Henriques as far back as 1947 revealed that burns will not occur if the temperature is below 44° C. (111.2° F.).

The present invention comprises an oxide-resistant ground connection to a ground plate or ground electrode, the oxide-resistant ground connection comprising an electrically conductive metal having an exposed surface area provided with an oxide layer, wherein the electrically conductive metal is characterized as having been treated to provide a treated electrically conductive metal surface where the oxide layer on at least a portion of the exposed surface area has been removed; an oxide-resistant electrically conductive coating contacting the treated metal surface; an electromagnetic interference (EMI) filter capacitor comprising a ground electrode plate interleaved in a capacitive relationship with an active electrode plate, or an EMI filter circuit comprising a ground plate, or an electronic circuit for an active implantable medical device (AIMD), the electronic circuit comprising a ground plate; and an electrically conductive material electrically connecting the ground electrode plate or the ground electrode to the oxide-resistant electrically conductive coating. The oxide-resistant ground connection also comprises a barrier layer that contacts the treated metal surface and the oxide-resistant electrically conductive coating contacts the barrier layer, wherein the barrier layer or the oxide resistant coating is a sputter deposited layer. The barrier layer is further characterized as having been deposited on the treated metal surface and independently the oxide resistant coating is further characterized as having been deposited on the barrier layer by one of the group of physical vapor deposition, chemical vapor deposition, electrostatic spray assisted vapor deposition (ESAVD), electron beam physical vapor deposition (EBPVD), ion plating, ion beam assisted deposition (IBAD), magnetron sputtering, pulsed laser deposition, sputter deposition, vacuum deposition, pulsed electron deposition (PED), plating, electroless plating, electroplating, spraying, painting, plasma spraying, thermal spraying, spin coating, dip coating, metal foil lamination, and as a thin film deposited layer. The electrically conductive metal having the oxide layer is selected from the group of a housing for an AIMD, a ferrule that is configured to be installed into an opening of an AIMD housing, a ground pin mechanically connected to a ferrule. The EMI filter capacitor or the EMI filter circuit board of the oxide-resistant ground connection is provided with a metallization contacting the respective ground electrode plate or the ground electrode, and the electrically conductive material directly electrically connects to the metallization and the oxide-resistant electrically conductive coating contacting the treated electrically conductive material. The EMI filter capacitor of the oxide-resistant ground connection is selected from the group of a feedthrough capacitor, an internally grounded feedthrough capacitor, an MLCC chip capacitor, an X2Y attenuator, and a flat-thru capacitor. The EMI filter circuit of the oxide-resistant ground connection is selected from a filter circuit board, or the electronic circuit is selected from an AIMD electronic circuit board, an AIMD electronic component, a sensor, and an antenna. An electrically conductive adhesive (ECA) stripe may optionally be contacted to at least a portion of the oxide-resistant electrically conductive coating contacting the treated electrically conductive surface, wherein the electrically conductive material directly contacts the ECA stripe. The electrically conductive material of the oxide-resistant ground connection is selected from the group of a solder, an electrically conductive adhesive, an electrically conductive thermal-setting adhesive, an electrically conductive epoxy, an electrically conductive polyimide, and an electrically conductive elastomer. The oxide-resistant electrically conductive coating is selected from the group of gold, a gold alloy, rhodium, a rhodium alloy, platinum, a platinum alloy, a platinum-iridium alloy, palladium, a palladium alloy, nitinol, a cobalt-chromium alloy, and combinations thereof. An optional barrier may be disposed between the oxide-resistant coating and the treated electrically conductive surface. The electrically conductive material has an exposed surface area, wherein the oxide layer oxidizable surface comprises titanium or a titanium alloy.

BRIEF DESCRIPTION OF THE DRAWINGS

FIG. 13A illustrates an exploded perspective view of an internally grounded prior art feedthrough capacitor, FIG. 13B illustrates the assembled monolithic structure of the internally grounded prior art feedthrough capacitor of FIG. 13A;

FIG. 13C illustrates the filter and feedthrough components of FIG. 13B fully assembled into a hermetically sealed filter feedthrough terminal;

FIG. 23A is taken from section 23A-23A of FIG. 23;

FIG. 23B is taken from section 23B-23B of FIG. 23 illustrating a circuit board and internal ground plate;

FIG. 23G illustrates that the circuit board of FIG. 23 may have an edge ground metallization that is conductively coupled to the oxide-resistant ground pin of FIG. 23C;

FIG. 23H is similar to FIG. 23D, except that the ground via hole is spatially aligned over a gold pocket-pad formed in a feedthrough ferrule recess;

FIG. 23I is the schematic diagram for the oxide-resistant filter attachments of FIGS. 23 and 23A through 23H;

FIG. 27 is taken from section 27-27 of FIG. 26 showing the top view of the MLCC filter circuit board;

FIG. 28 is taken from section 28-28 of FIG. 26 showing at least one circuit board ground plate;

FIG. 37 illustrates a prior art quadpolar flat-thru filter capacitor,

FIG. 38 illustrates internal sections taken from section 38-38 from FIG. 37 showing the flat-thru active and ground electrode plates;

FIG. 47 is a table showing a listing of U.S. patents having embodiments that may comprise oxide-resistant electrical attachments of the present invention. The embodiments within these patents can use the oxide-resistant coating of the present invention. As such, all of these U.S. patents are incorporated herein fully by this reference.

DETAILED DESCRIPTION OF THE INVENTION

Figure 1:
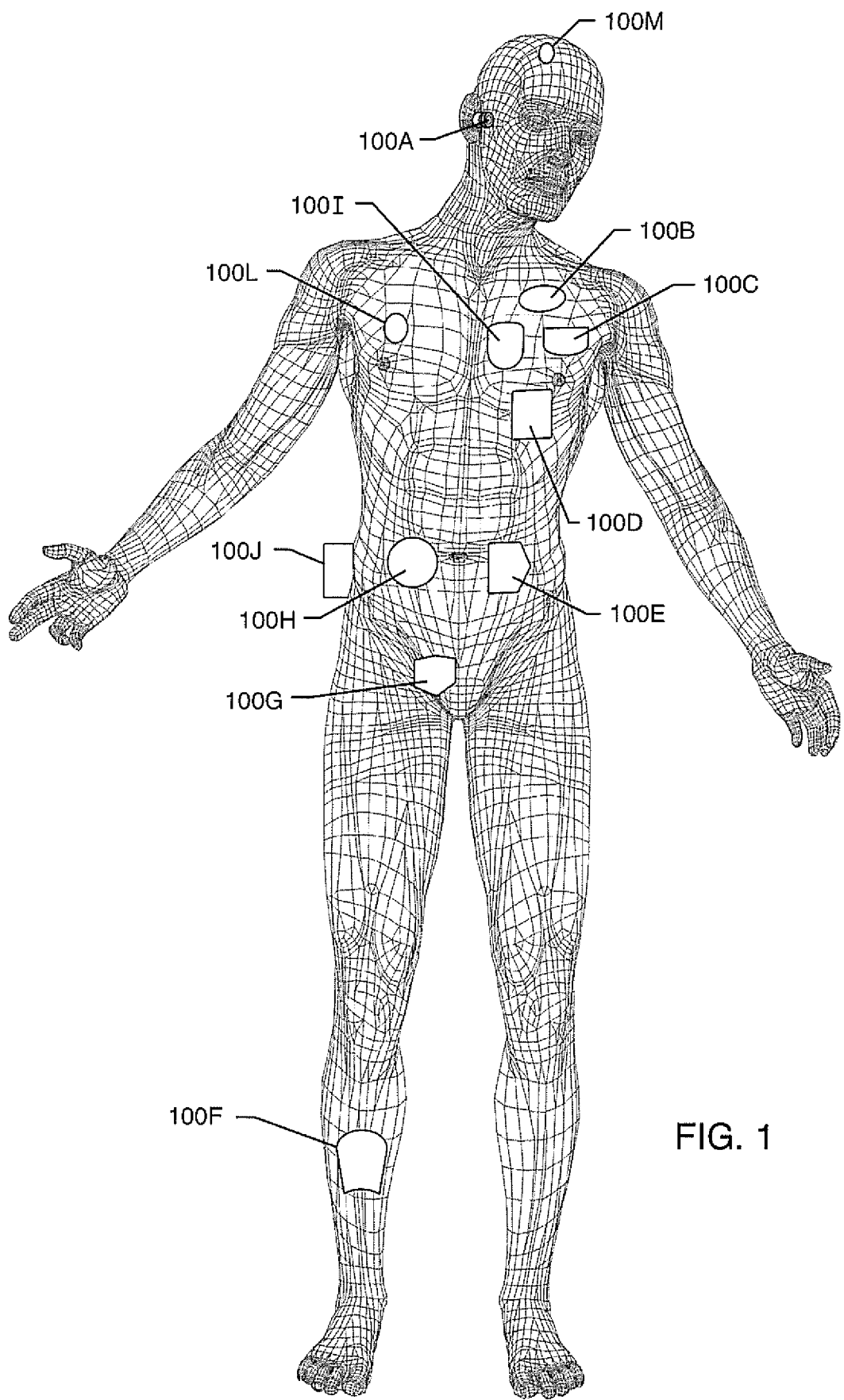
FIG. 1 is a wire-formed diagram of a generic human body showing a number of exemplary implantable medical devices.

FIG. 1 illustrates various types of active implantable and external medical devices 100 that are currently in use. FIG. 1 is a wire formed diagram of a generic human body showing a number of implanted medical devices. 100A is a family of external and implantable hearing devices which can include the group of hearing aids, cochlear implants, piezoelectric sound bridge transducers and the like. 100B includes an entire variety of neurostimulators and brain stimulators. Neurostimulators are used to stimulate the Vagus nerve, for example, to treat epilepsy, obesity and depression. Brain stimulators are similar to a pacemaker-like device and include electrodes implanted deep into the brain for sensing the onset of a seizure and also providing electrical stimulation to brain tissue to prevent the seizure from actually happening. The leadwires that come from a deep brain stimulator are often placed using real time imaging. Most commonly such leadwires are placed during real time MRI. 100C shows a cardiac pacemaker, which is well-known in the art and may have endocardial or epicardial leads. Implantable pacemakers may also be leadless. The family of cardiac pacemakers 100C includes the cardiac resynchronization therapy devices (CRT-P and CRT-D) and leadless pacemakers. CRT-P devices are unique in that they pace both the right and left ventricles of the heart to help them contract at the same time to help the heart pump more efficiently. A CRT-D device is a special device for heart failure patients who are also at high risk for sudden cardiac death. While functioning like a normal pacemaker to treat slow heart rhythms and also delivering small electrical impulses to the left and right ventricles to help them contract at the same time, the CRT-D device is also capable of delivering shock to the heart to treat dangerously fast heart rhythms that can lead to sudden death. The 100C device family also includes all types of implantable loop recorders or biologic monitors, such as cardiac monitors. 100D includes the family of left ventricular assist devices (LVAD's) and artificial hearts. 100E includes an entire family of drug pumps, which can be used for dispensing of insulin, chemotherapy drugs, pain medications and the like. Insulin pumps are evolving from passive devices to ones that have sensors and closed loop systems. That is, real time monitoring of blood sugar levels will occur. These devices tend to be more sensitive to EMI than passive pumps that have no sense circuitry or externally implanted leadwires. 100F includes a variety of external or implantable bone growth stimulators for rapid healing of fractures. 100G includes urinary incontinence devices. 100H includes the family of pain relief spinal cord stimulators and anti-tremor stimulators. 100H also includes an entire family of other types of neurostimulators used to block pain. 100I includes a family of implantable cardioverter defibrillator (ICD) devices and also includes the family of congestive heart failure devices (CHF). This is also known in the art as cardiac resynchronization therapy devices, otherwise known as CRT devices. 100J illustrates an externally worn pack. This pack could be an external insulin pump, an external drug pump, an external neurostimulator, a Holter monitor with skin electrodes or even a ventricular assist device power pack. Referring once again to element 100C, the cardiac pacemaker could also be any type of biologic monitoring and/or data recording device. This would include loop recorders or the like. Referring once again to FIG. 1, 100I is described as an implantable defibrillator. It should be noted that these could be defibrillators with either endocardial or epicardial leads. This also includes a new family of subcutaneous defibrillators.

Figure 2:
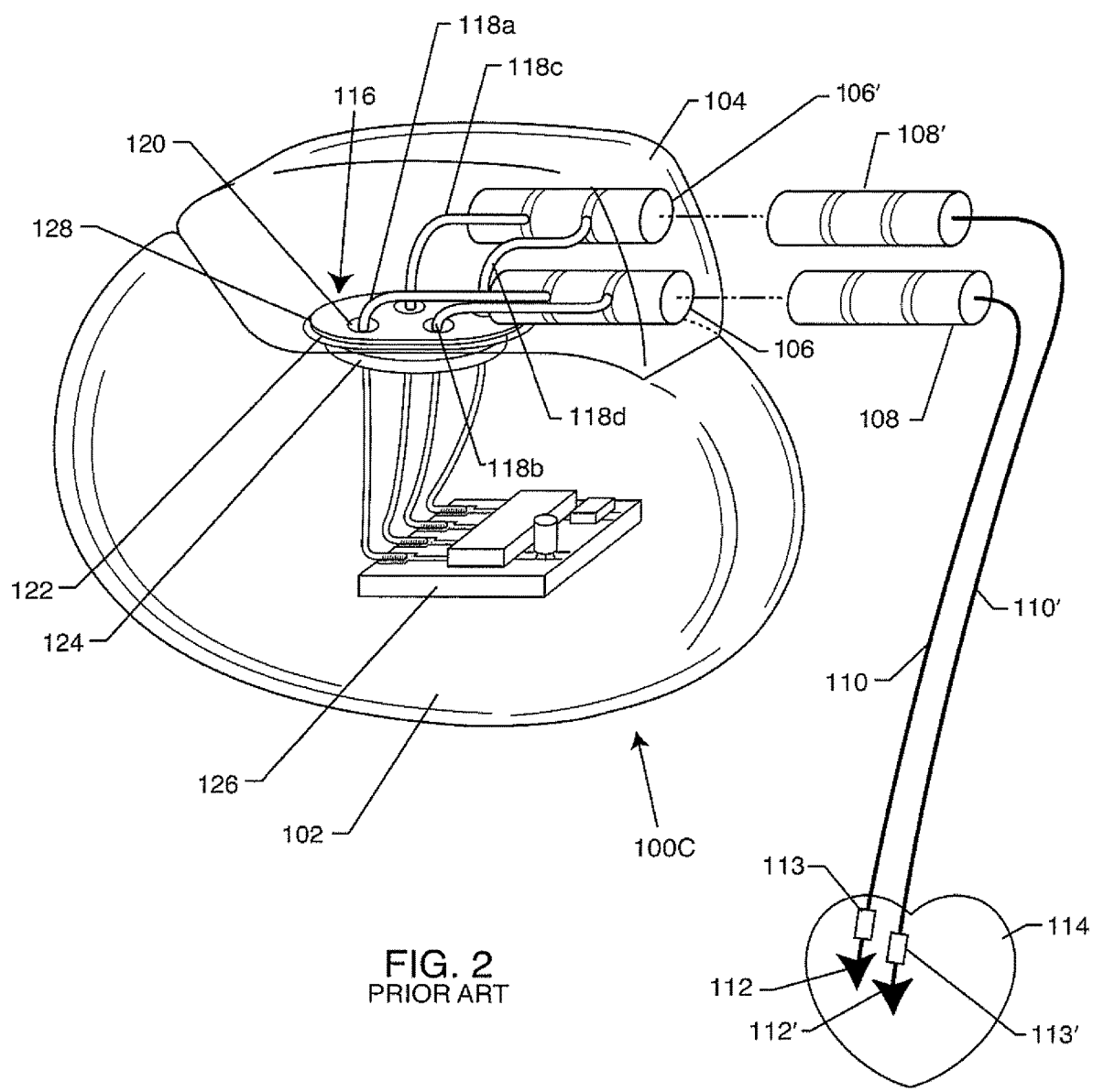
FIG. 2 is a side view of a prior art cardiac pacemaker.

FIG. 2 illustrates a side cutaway view of a prior art cardiac pacemaker 100C. The pacemaker electronic circuits are housed in a hermetically sealed and conductive electromagnetic shield 102 (typically titanium). There is a header block assembly 104 generally made of thermal-setting non-conductive plastic, such as Tecothane™. This header block assembly 104 houses one or more connector assemblies generally in accordance with ISO Standards IS-1, IS-2, or more modern standards, such as IS4 or DF4. The header block connector port assemblies are shown as 106 and 106'. Implantable leadwires 110, 110' have proximal plugs 108, 108' and are designed to insert into and mate with the header block connector cavities 106 and 106', or, alternatively, directly into the pulse generator itself for devices that do not have header block assemblies.

Referring once again to FIG. 2, one can see an active electronics AIMD circuit board 126. Active circuit boards require a source of electrical energy, energy storage, power, and combinations thereof. The electrical energy source comprises a primary battery, a secondary battery, or both; the energy storage source comprises an energy storage capacitor, and the power source comprises an electrical energy system, a power system, or both. Active electronics include at least one microelectronic or microchip component, for example, but not limited to, an application-specific integrated circuit (ASIC) chip or an integrated circuit (IC) chip. As will be further discussed, a passive electronic electromagnetic interference (EMI) filter chip may alternatively be disposed in the location of the feedthrough capacitor 124.

As used herein, the term "lead" refers to an implantable lead containing a lead body and one or more internal lead conductors. A "lead conductor" refers to the conductor that is inside of an implanted lead body and is not to be confused with the term "lead wire". The term "leadwire" or "lead wire" refers to wiring that is either inside of the active implantable medical device (AIMD) housing or inside of the AIMD header block assembly or both. Furthermore, as used herein, in general, the terms lead, leadwire and pin are all used interchangeably. Importantly, they are all electrical conductors. This is why, in the broad sense of the term, lead, leadwire or pin can all be used interchangeably since they are all conductors. The term "conductive pathway" can also be used to be synonymous with lead conductor, lead, leadwire or pin or even a circuit trace.

As described herein, composite conductive sintered paste filled vias passing through an insulator in nonconductive relation with a ferrule electrically acts the same as leadwire, lead wire, or pin. These sintered paste-filled vias may also incorporate co-fired solid leadwires.

As used herein, the term paste generally refers to pastes, inks, gels, paints, cermets, and other such metal and/or metal/ceramic sinterable material combinations that can be flowable, injectable, pressed, pulled, pushed or otherwise movable into an orifice or via. Post-sintering, the solvents and binders are baked out and, after sintering, the paste becomes a densified solid with monolithic structure. Additionally, AIMD, as defined herein, includes electronic circuits disposed within the human body that have a primary or secondary battery, or have an alternative energy source, such as energy induced by motion, thermal or chemical effects or through external induction.

As used herein, the term "header block" refers to the biocompatible material structure that provides a means of electrical connection of the AIMD pulse generator and the therapy delivery lead(s). The term "header block assembly" refers to a header block including the connector ports for the therapy delivery lead(s) and the wiring connecting the therapy delivery lead connector ports to the hermetic terminal subassemblies, which allow electrical connections for current to pass inside the AIMD housing. It is understood by those skilled in the art that the present invention can also be applicable to AIMDs that do not have a header block or header block connector assemblies, such as cochlear or retinal implants.

Figure 2A:
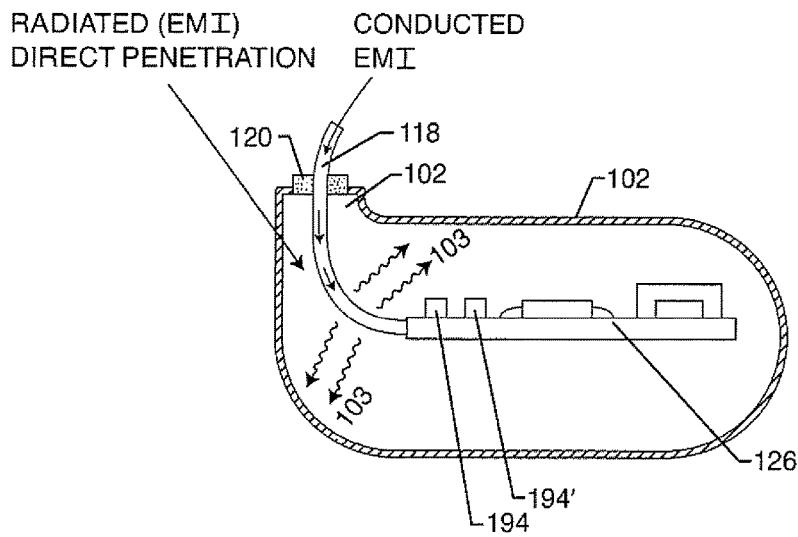
FIG. 2A is a sectional view of the prior art pacemaker of FIG. 2.

FIG. 2A shows an exemplary sectional view of the AMD previously disclosed in FIG. 2. In this case, MLCC chip capacitor 194, 194' filter components are undesirably located on the AIMD circuit board 126, which is disposed at a distance from the hermetic seal insulator 120 inside the hermetically sealed AIMD housing 102. In this case, radiated EMI directly penetrates through the feedthrough insulator 120 into the interior of the AIMD housing 102. In addition, conducted EMI, which is coupled to implanted leads by induction or antenna action, can enter the AIMD housing by way of its leadwires. FIG. 2A is thus a representation of poor practice as the EMI is allowed to enter inside of the AIMD housing 102 before the EMI is filtered by the MLCC chip capacitor 194, 194' or other filter components on the AIMD circuit board 126. Entry of EMI to the AIMD device side can cause the EMI to reradiate on the inside of the AIMD housing, as shown by arrows 103. At high frequencies, this unfiltered EMI can dangerously couple to AIMD sensitive circuits, such as pacemaker sense circuits. Such unfiltered EMI can thereby cause malfunction of the AIMD. In the case of cardiac implantable electronic devices (CIED), such as an implantable defibrillator or pacemaker, this EMI interaction can be dangerous, even life-threatening to the patient.

Figure 2B:
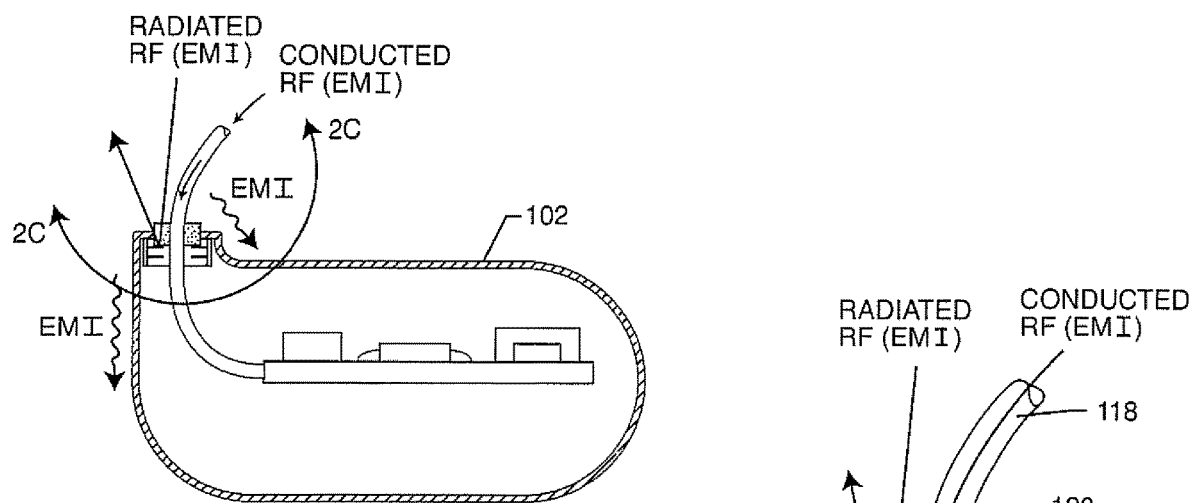
FIG. 2B illustrates how an EMI filter can reflect and divert EMI energy from entering the pacemaker of FIG. 2A.

FIG. 2B is similar to FIG. 2A, except now a feedthrough EMI filter capacitor 124 is disposed adjacent to the hermetic seal insulator 120. The EMI filter capacitor internal electrode plates, particularly the ground electrode plates of the feedthrough EMI filter capacitor 124, reflect and absorb radiated EMI such that it cannot enter inside the AIMD housing 102. At the same time, the filter capacitor diverts conducted EMI and dissipates the EMI harmlessly to the AIMD housing 102.

Figure 2C:
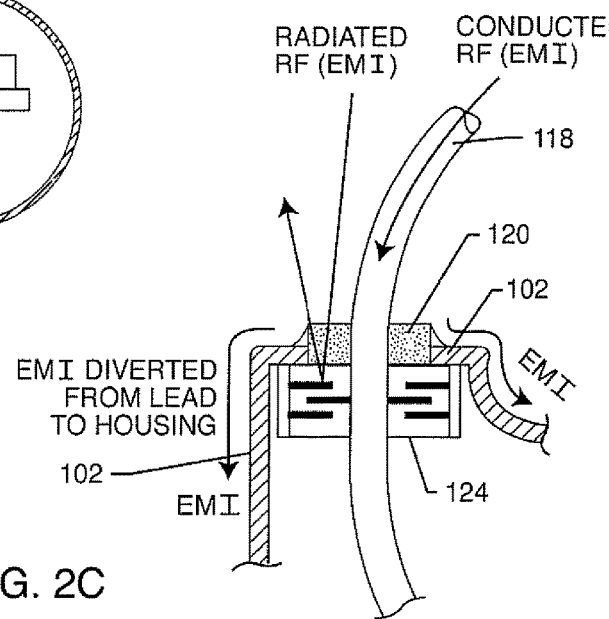
FIG. 2C is a sectional view taken from FIG. 2B, illustrating how a feedthrough capacitor works to reflect and divert EMI.

FIG. 2C is an enlarged view taken from section 2C-2C of FIG. 2B illustrating the internal electrode plates of the feedthrough EMI filter capacitor 124 and its connection to the AIMD housing 102, which is system ground 144. As defined herein, an EMI filter system ground 144 is the AIMD housing 102, which can also optionally include a metallic electrically conductive feedthrough ferrule 122 hermetically sealed to an insulator 120 of the feedthrough. The feedthrough ferrule 1122 is mechanically and electrically attached to an opening in the AIMD housing 102 by processes, such as, but not limited to, laser welding or brazing. Alternatively, the feedthrough ferrule 122 may be formed as a contiguous extension of the AIMD housing 102.

As used herein, the acronym AIMD stands for active implantable medical device. A family of AIMDs is described above in FIG. 1. As defined herein, active components, such as an active implantable medical device circuit board or an active electronic circuit board, require a source of power or energy, such as a primary or a secondary battery. There are other sources of energy involving wireless energy transfer or converting ultrasonic waves, or even energy harvesting derived from biomechanical motions of human organs, such as cardiac motion, blood flow, breathing and the like, which collects and stores electric power or energy for later use. Passive AIMD electronic components or passive AIMD circuit boards do not require a source of power or energy and consist of passive components, including capacitive, inductive, and resistive elements. Also, as defined herein, CRT-P stands for cardiac resynchronization pacemaker and CRT-D stands for cardiac resynchronization defibrillator. CRT-P and CRT-D devices differ from prior art pacemakers and defibrillators, in that they have a third wire system routed outside the left ventricle and are thereby able to completely resynchronize the heart.

Figure 3:
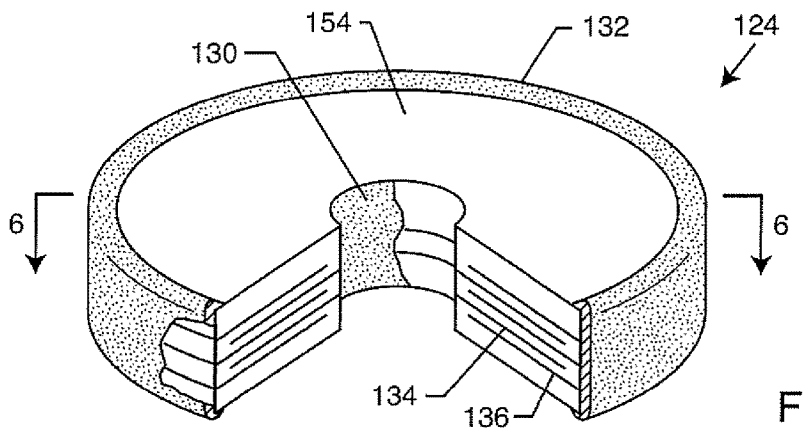
FIG. 3 is a perspective partial cutaway view of a unipolar capacitor.

FIG. 3 illustrates an isometric cut away view of a unipolar feedthrough capacitor 124. Shown are active electrode plates 134 and ground electrode plates 136 both interleaved and disposed within a capacitor dielectric 154. Also shown is the unipolar feedthrough capacitor feedthrough hole (passageway), including metallization 130 and an outside diameter metallization 132.

Figure 4:
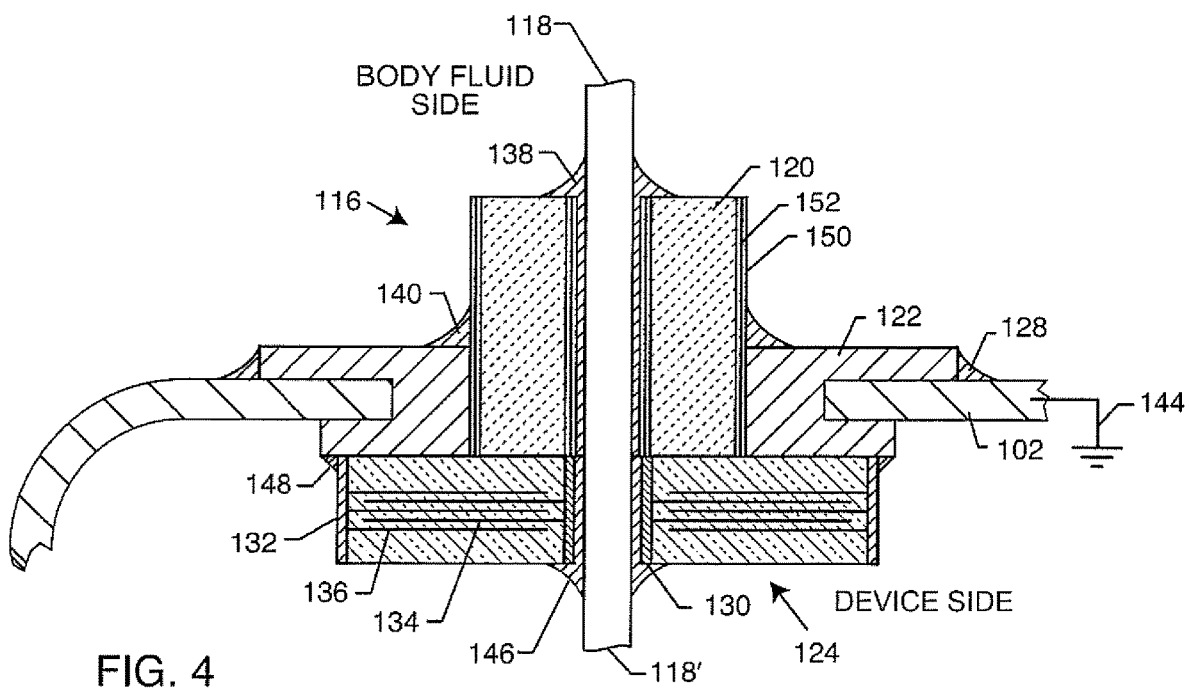
FIG. 4 is a side sectional view of a similar unipolar capacitor of FIG. 3 now mounted to a hermetic feedthrough for an active implantable medical device.

FIG. 4 illustrates a cross-sectional view of the prior art unipolar feedthrough capacitor of FIG. 3. The unipolar feedthrough capacitor 124 is mounted to a ferrule 122 of a hermetically sealed feedthrough 116 for use in an active implantable medical device (AIMD). As shown, the ferrule 122 is configured to be laser welded 128 into an opening of an AIMD housing 102. The AIMD housing 102 generally comprises titanium, however, can comprise other biocompatible electrically conductive materials. Additionally, the AIMD housing 102 forms an overall electromagnetic shield to help shield and protect AIMD electronics from electromagnetic interference (EMI) emitters, such as cell phones and the like. Accordingly, FIG. 4 illustrates a symbol for an EMI filter system ground 144 indicating that EMI signals, which may couple to the body fluid side of the lead 118, are decoupled or diverted through the feedthrough capacitor 124 to the equipotential electromagnetic shield 102, 144 (i.e., the housing of the AIMD). When high frequency EMI signals are diverted from lead 118 to the AIMD housing 102, the EMI signals circulate around the electromagnetic shield (the housing) and are converted into meaningless heat (just a few milli or microwatts). In an MRI environment, such as a 1.5 Tesla (T) or 3 T MRI scanner, there is a powerful pulsed RF field. The RF field consists of short pulses at specified intervals, and its carrier frequency is directly related to the strength of the static field of the MRI. The RF frequency of a 1.5 T MRI scanner is 64 MHz. The RF frequency of a 3 T MRI scanner is 128 MHz. In the specific case of MRI, the feedthrough capacitor 124 must divert a much higher level of RF current. In some cases, this could even be amps of RF current.

Figure 5:
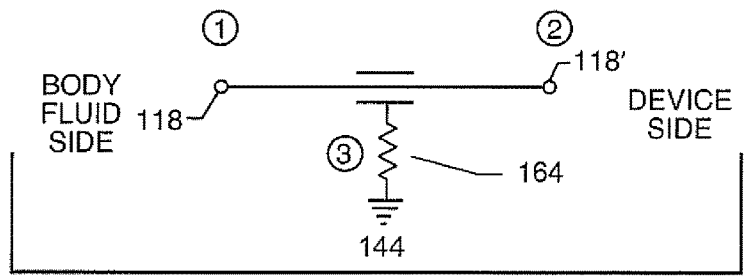
FIG. 5 is an electrical schematic representation of the unipolar filter feedthrough assembly previously illustrated in FIG. 4.

FIG. 5 is the electrical schematic of the feedthrough filter capacitor of FIG. 4. Noticeable is an undesirable resistance $R_{OXIDE}$ 164. When the filter capacitor is diverting high levels of current, such as in an MRI environment, substantial heating of the resistive $R_{OXIDE}$ 164 (in other words, a parasitic resistance imparted to the filter capacitor due to the presence of oxides at the filter attachment surface) can occur, which can undesirably overheat the filter capacitor and its connections. Such overheating is also known as the $I^2R$ loss of the filter capacitor. The $I^2R$ loss is the power dissipated in the capacitor's own equivalent series resistance (ESR). The present invention is directed towards minimizing or eliminating this parasitic resistance $R_{OXIDE}$ 164.

Referring once again to FIG. 4, illustrated is an electrical connection material 148 directly connected to the oxidizable surface of the feedthrough ferrule 122. Typically, the ferrule 122 comprises titanium, which easily forms oxides. In fact, titanium's biocompatibility is directly attributed to the oxides so easily formed on titanium surfaces. However, these same oxides are very resistive and can even be semi-conductive. It was not known at the time the prior art filters of FIG. 4 were built that filter performance would seriously degrade over time due to titanium oxides.

Referring once again to FIG. 4, one can see the traditional circuit system ground symbol 144. As used herein, system ground, represented by the ground symbol illustrated by FIG. 4 as element 144, can be connected either directly to the AIMD housing 102 or to the feedthrough ferrule 122. As defined herein, the schematic ground symbols used throughout the present patent drawings represent EMI filter system ground 144. At both low and high frequencies, housing 102 and ferrule 122 are at the potential of the system ground 144 as a result of the continuous laser weld 128 that mechanically and electrically joins together the housing 102 and the ferrule 122.

Referring again to electrical schematic of FIG. 5, illustrated is that the feedthrough capacitor of FIGS. 3 and 4 is a three-terminal device capable of significant high frequency attenuation along the length of the leadwire 118,118' extending to the body fluid side lead end 118 and to the device side lead end 118'. Accordingly, the body fluid side lead end 118 is a first terminal, the device side lead end 118' is a second terminal, and the system ground 144, which is the AIMD housing 102, is the third terminal, to which undesirable EMI is diverted. It is known to one skilled in the art that three-terminal feedthrough capacitors have very little to no parasitic series inductance and are therefore very broadband low pass filters. This means that low frequency signals, such as therapeutic pacing pulses or biologic signals, pass through the body fluid side of the lead 118 to the device side of the lead 118' without degradation or attenuation. However, at high frequencies, the capacitive reactance drops to a very low number and desirably, high frequency signals are selectively diverted from the lead conductor 118, 118' to the ferrule 122 and, in turn, to the conductive AIMD housing 102. Referring once again to FIG. 5, it is important to emphasize that the resistance $R_{OXIDE}$ 164 between the filter capacitor 124 and the system ground 144 is highly undesirable at frequencies above 10 MHz and, particularly, at MRI frequencies of 64 MHz and 128 MHz. This resistance $R_{OXIDE}$ 164, which is more evident at these higher frequencies, is the direct result of the oxides or the thickening of oxides that develop on the titanium surface of the ferrule 122 or the AIMD housing itself 102 in the electrical connection 148 shown in FIG. 4.

Figure 6:
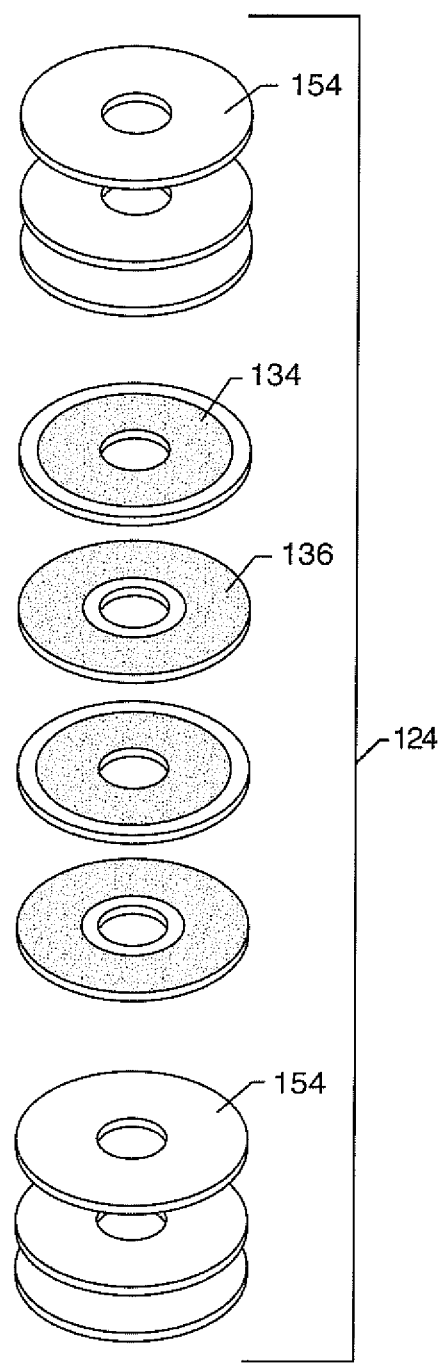
FIG. 6 is generally taken along lines 6-6 from FIG. 3 and is an exploded perspective view of the electrode layer stack up.

FIG. 6 is an exploded view of the unipolar feedthrough filter capacitor of FIG. 3 showing that the feedthrough filter capacitor comprises (from the top down): one or more ceramic cover plates 154; active electrode plates 134 interleaved with ground electrode plates 136; and another set of one or more cover sheets 154. In ceramic engineering, the ceramic dielectrics would typically be of BX or X7R having a dielectric constant of approximately 3000 or higher. It is appreciated that NP0, which is generally a low k dielectric with a dielectric constant below 200, can also be used, which is taught in U.S. Pat. No. 8,855,768, the content of which are incorporated fully herein by this reference. Filter capacitors having a dielectric constant of <1000 can also be used and are taught by U.S. Pat. No. 10,561,837, the contents of which are incorporated herein fully by reference. For the emerging MRI filter applications, both filter performance (insertion loss in Decibels or dB) is very important as well as limiting, even substantially eliminating, resistance 164 due to oxides ($R_{OXIDE}$). Use of a low k dielectric, such as a dielectric constant below 1000 or even below 200, has many advantages in MRI environments, which include: 1) the dielectric loss tangent is significantly reduced, which means that resistive losses in the dielectric itself are minimized; 2) the capacitance change versus frequency is much less for these lower k dielectrics. Less capacitance change with frequency means that at 64 MHz and 128 MHz, the filter has more capacitance and hence more filtering at these key frequencies. Teaching that the filtered capacitor ground connection can be done in an oxide-free manner is a particularly important aspect of the present invention and works very well in concert with the use of lower k dielectrics. The present invention also works very well with the more commonly used dielectrics from 1200 k to 5000 k.

Figure 6A:
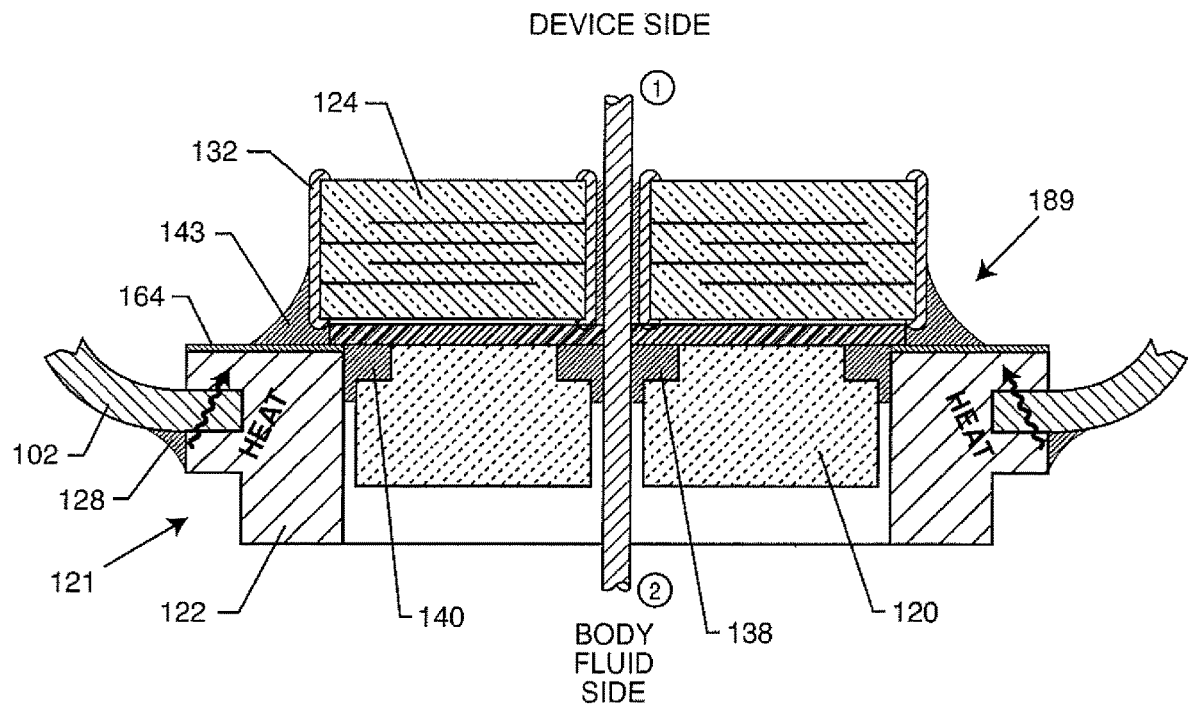
FIG. 6A is a sectional view a hermetically sealed filter feedthrough assembly showing the undesirable formation of a surface oxide layer on the surface of the feedthrough ferrule.
Figure 6B:
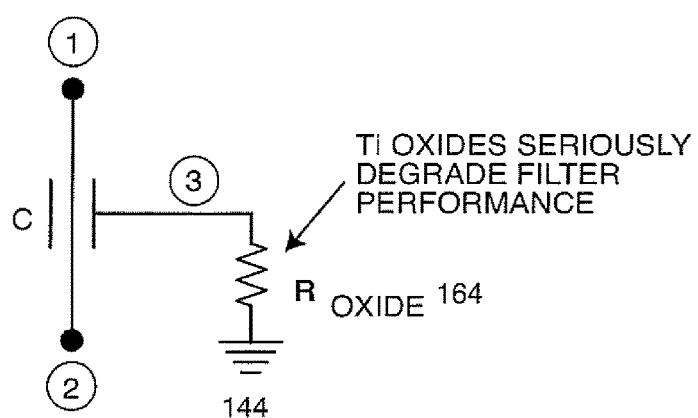
FIG. 6B is the electrical schematic of the hermetically sealed filter feedthrough assembly of FIG. 6A illustrating the resistance due to the EMI filter being directly attached to the feedthrough ferrule oxidized surface.

FIG. 6A shows that the feedthrough capacitor ground termination 132 of FIG. 3 has been electrically connected using an electrical connection material 143 applied directly to ferrule 122. Even if one mechanically or chemically cleans the ferrule of all oxides before the electrical connection is made, a surface oxide 164 can reform between the electrical connection material 143 and the ferrule 122. The electrical connection material 143 typically used in this case is a thermal-setting conductive adhesive, such as a conductive polyimide, a conductive polymer, a conductive elastomer or a conductive epoxy. As defined throughout this specification, the use of a thermal-setting electrically conductive adhesive is also known as an electrically conductive adhesive or ECA. The ferrule 122 is typically laser welded 128 in an opening of the AIMD housing 102. As previously indicated, laser welding creates a substantial amount of localized heat, which can further accelerate oxide formation. Even if the inside environment of the AIMD housing is evacuated and backfilled with an inert gas, oxygen can be released from, for example, the thermal-setting conductive adhesive (electrical connection material 143) as the adhesive is heated during the laser welding process. The formation of this surface oxide 164 is detrimental to filter performance, shown as $R_{OXIDE}$ in FIG. 6B.

Figure 6C:
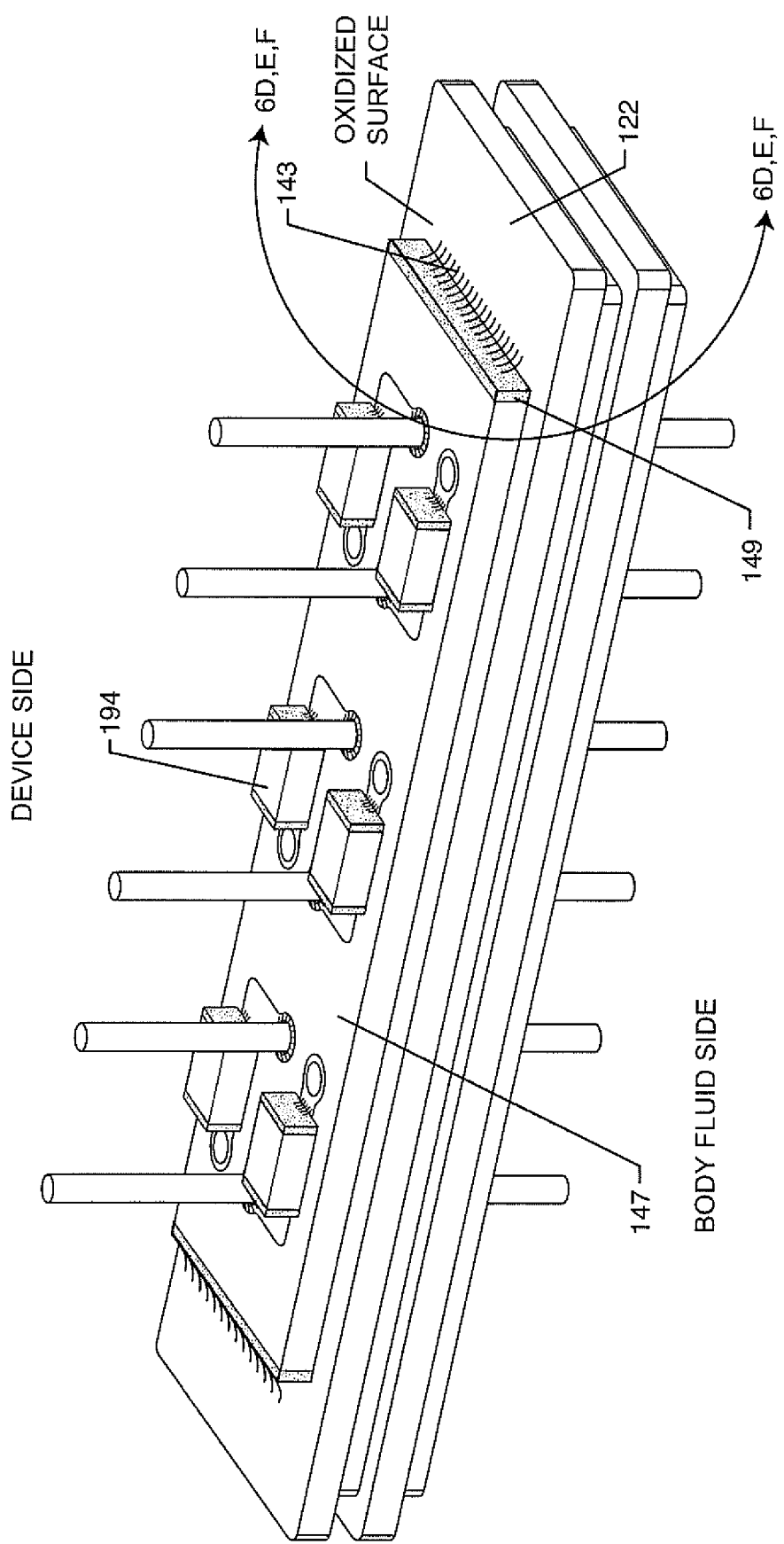
FIG. 6C illustrates a prior art MLCC filter circuit board improperly grounded to an oxidized ferrule surface.

FIG. 6C illustrates an exemplary EMI filter circuit board 14'7 on which six MLCC chip capacitors 194 are disposed. The EMI filter circuit board 147 has at least one internal ground plate 156 (not shown). The ground plate is attached to THE circuit board metallizations 149. An electrically conductive adhesive or ECA 143 is directly connected between the circuit board ground metallization 149 and the oxidizable surface of the ferrule 122. Typically, a ferrule made of titanium comprises an oxidized surface, which, as previously disclosed, imparts biocompatibility to the titanium. There are some manufacturers that, in ignorance, believe that titanium oxides can be removed mechanically or chemically to thereby produce a stable and reliable electrical connection 143 to the surface of the titanium ferrule 122. However, this is a myth. Oxides will readily form again underneath the electrical connection 143, particularly when the ferrule is heated, such as by laser welding into an opening of the AIMD housing 102.

Figure 6D:
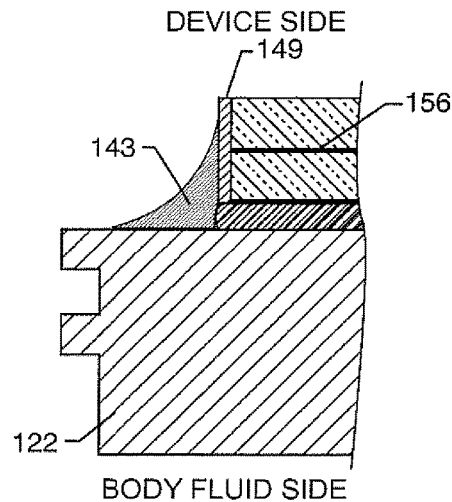
FIG. 6D is taken from section 6D-6D from FIG. 6, showing the circuit board electrical ground connection directly electrically connected to the oxidizable ferrule surface.

FIG. 6D is taken from section 6D-6D from FIG. 6C and illustrates that the electrical ground connection material 143 is disposed on the circuit board ground edge metallization 149 and directly on the surface of the ferrule 122, which, as previously disclosed, is not good practice. For simplicity, FIG. 6D does not show an oxide layer 164; however, the inventors of the present application have reproducibly demonstrated that even curing a thermal setting conductive adhesive 143 in a vacuum (a hard vacuum, which is a very difficult process) in an attempt to prevent the titanium ferrule 122 from reforming any oxides proved futile. A reproducible, stable and oxide-free connection was just not achievable. It is further noted that the electrical connection 143, as illustrated in FIG. 6D, cannot even be made using a solder, since a titanium ferrule 122 is not solderable because solders do not wet to titanium.

Figure 6E:
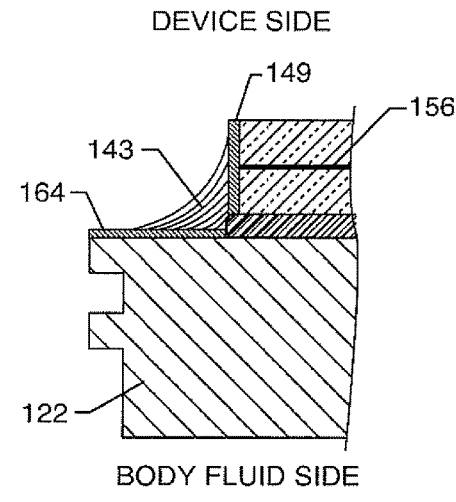
FIG. 6E is taken from section 6E-6E from FIG. 6, showing the formation of an oxide layer between the circuit board electrical ground connection and the ferrule surface.

FIG. 6E is taken from section 6E-6E from FIG. 6C and illustrates the undesirable formation of an oxide layer 164 ($R_{OXIDE}$) on the surface of a ferrule 122. It is appreciated, that the surface oxide layer 164 would generally occur over all surfaces of the ferrule but is only shown on the top for simplicity. As previously discussed, the surface oxide layer 164 greatly increases the resistance ($R_{OXIDE}$) or equivalent series resistance (ESR) to the circuit board ground plates 156 and then, in turn, to the MLCC chip capacitors 194 (not shown). Referring once again to FIG. 6E, the surface oxide layer 164 ($R_{OXIDE}$) is formed and/or re-formed underneath the electrical connection 143, that is, between the electrical connection material 143 and the previously cleaned ferrule 122. As previously disclosed, the electrical connection material 143 is a thermal-setting electrically conductive adhesive, including electrically conductive polyimides, electrically conductive polymers, electrically conductive elastomers and electrically conductive epoxies. The surface oxide layer 164 is characteristically present on the titanium surface at the time electrical connection material 143 is applied, or the surface oxide layer can form over time (later) between the ferrule 122 and the electrical connection material 143, in particular, during laser welding 128 of the ferrule 122 to the AIMD casing 102. When conducting a laser weld 128, substantial localized heat may be generated, which can accelerate surface oxide layer 164 formation.

It is incorrectly believed by some that surface oxide layer 164 will not form on titanium components internal to the AIMD housing 32 once the housing is hermetically sealed, because the free area inside of the AIMD housing is generally evacuated with a vacuum of its interior gaseous environment and then backfilled with inert gas, such as helium, nitrogen or argon, with the intention of eliminating moisture. The belief that vacuum evacuation and back-filling with inert gas will inhibit oxidation of sensitive materials like titanium is erroneous. Materials of construction used in the manufacture of AIMDs, such as polymers, plastics, adhesives, elastomers and the like, and even the printed circuit boards (PCBs) themselves, generally have some level of gases trapped within their structure; for example, moisture, oxygen, other oxygen-containing gases, or even undetected residues comprising the same, which eventually outgas during the operating life of the device. Furthermore, processes that do involve increased temperature, like welding, curing or other temperature shifts, actually accelerate such outgassing. Hence, even if an AIMD is manufactured in an inert gas environment, or backfilled with an inert gas, such 'heating' of certain materials of construction can release the oxygen, oxygen-containing gases or water vapor into an otherwise hermetically sealed environment, causing the formation of insulative surface oxide layers 164 on otherwise electrically conductive titanium surfaces 102, 122. It is extremely important that no undesirable surface oxides form in the system ground 144 connection of an EMI filter. It is also important during a qualification and during production, that filter performance metrics be measured. These filter performance metrics must include: Equivalent Series Resistance (ESR) at above 10 MHz and, in particular, at 64 MHz (MRI RF-pulsed frequency of a 1.5T scanner), and insertion loss (IL) sweeps in dB on a network analyzer from 10 MHz to 3000 MHz, including 64 MHz (1.5T MRI scanner) and 128 MHz (3T MRI scanner). For more detail referring the effects of oxide layer formation on EMI filtering, refer to the paper entitled, "Dissipation Factor Testing is Inadequate for Medical Implant EMI Filters and Other High Frequency MLCC Capacitor Applications", ISSN: 0887-7491, presented at CARTS 2003: 23rd Capacitor and Resistor Technology Symposium, Mar. 31-Apr. 3, 2003, incorporated herein by this reference.

In summary, the presence of a surface oxide layer 164 can seriously degrade EMI filter performance (in dB), particularly at high frequencies or at MRI RF-pulsed frequencies, where the diverter filters must bypass a substantial amount of high frequency current. Importantly, the inventors found that an oxidizable EMI filter electrical ground connection, such as illustrated in FIGS. 6D, 6E and 6F, is a highly dangerous and undesirable approach, which can lead to highly degraded filter performance, even filter failure, and is, accordingly, a very poor and unsafe practice.

Figure 6F:
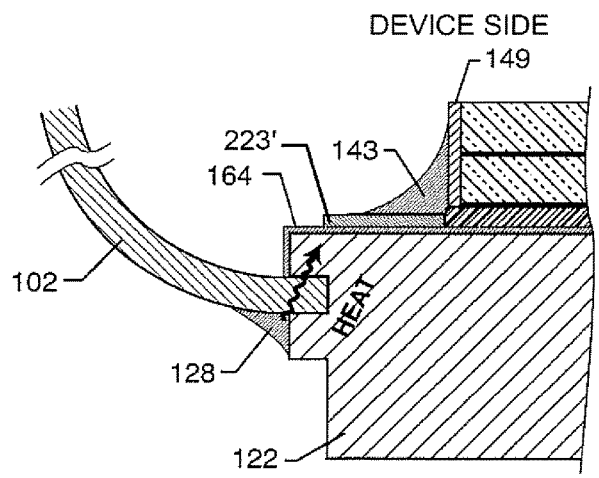
FIG. 6F is taken from section 6F-6F from FIG. 6, showing that laser welding heat substantially and dangerously thickened the oxide layer between the circuit board ground and the ferrule surface, unsafely compromising the circuit board electrical ground connection.

FIG. 6F is taken from section 6F-6F from FIG. 6C and illustrates the heat that is formed during laser welding 128 of the ferrule 122 into an opening of the AIMD housing 102. This heat undesirably does two things: 1) it heats up the electrical connection material 143, which is typically a thermal-setting conductive adhesive. This heating of the polymer releases free oxygen which then becomes available to form a thicker surface oxide layer 164. As shown, a surface oxide layer forms all over the inside of the housing. As previously discussed, titanium oxide formations are accelerated by elevated temperature. Referring once again to FIGS. 6E and 6F, the surface oxide layer 164 may comprise several layers, with any one or more layers further comprising one or more titanium oxide compositions. As mentioned, these surface oxide layers 164 are undesirably insulative and can also cause potentially undesirable semi-conductor behavior. One approach that the inventors have tried in the past is to clean the oxide layers 164 from the ferrule 122 device side surface using abrasive mechanical and chemical removal processes, including grit-blasting, mechanical grinding, sanding, and hydrofluoric acid cleaning. It should be noted that titanium oxides, once formed, are very stable and very hard to remove. In fact, titanium oxides are so stable that they are commonly used as paint pigments.

Referring once again to FIG. 6F, the inventors first cleaned the oxide layers 164 from the surface of the device side ferrule 122 and then formed an optional stripe or a coating of an electrically conductive adhesive (an optional ECA stripe 223'). The optional ECA stripe 223' comprised a thermal-setting conductive polyimide. During this experiment, there was no oxide-resistant coating layer 165 in accordance with the present invention. In other words, the optional ECA stripe 223' was directly applied to the titanium surface 122. The inventors then connected the ground metallization 132 of feedthrough filter capacitors 124 directly to the optional ECA stripe 223' with electrical connection material 148,143. This oxidizable connection seemed to work very well in high frequency electrical measurements, including insertion loss (IL), impedance, ESR and inductance, all initially measuring within acceptable specification limits. However, out of a prototype qualification lot of a thousand pieces evaluated, five (post laser welding) filters re-oxidized and exhibited much higher resistances (ESR), thus failing qualification testing. Graphs of ESR vs. frequency sweeps of three of these five failures are shown in FIGS. 6I, 6J and 6K, which alarmingly show dangerously out of specification (highly elevated) high frequency resistance (ESR) due to oxide formation $R_{OXIDE}$ 164, particularly at the critical MRI frequencies of 64 MHz and 128 MHz. As MRI scanners evolve to higher and higher magnetic field strengths, such as 5 Tesla or even higher (currently there are about 100 7T MRI scanners in the field operating at a frequency of 300 MHz), this means that the RF frequencies are also higher and having an oxide-free filter connection becomes even more critical. The magnitude of this failure rate in a 1000-piece lot (0.5%) is very alarming for life sustaining devices like implantable cardiac pacemakers and ICDs. Accordingly, a direct connection to a titanium surface is not only unacceptable but is also extremely dangerous.

Figure 6G:
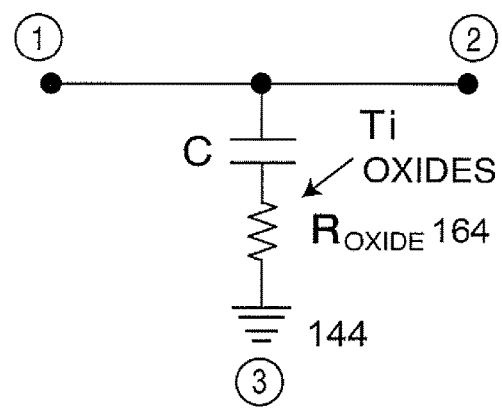
FIG. 6G is a schematic of the EM filter circuit board of FIG. 6 illustrating the resistance due to the EMI filter circuit board being directly attached to the feedthrough ferrule oxidized surface.

FIG. 6G illustrates the schematic diagram of the EMI filter circuit board of FIGS. 6C, 6D, 6E and 6F. Undesirably, $R_{OXIDE}$ 164 forms, which can either be immediate, latent or induced by thermal processes. As previously described, the formation of this $R_{OXIDE}$ seriously degrades EMI filter performance or causes EMI filters to actually fail therein not filtering at all.

Figure 6H:
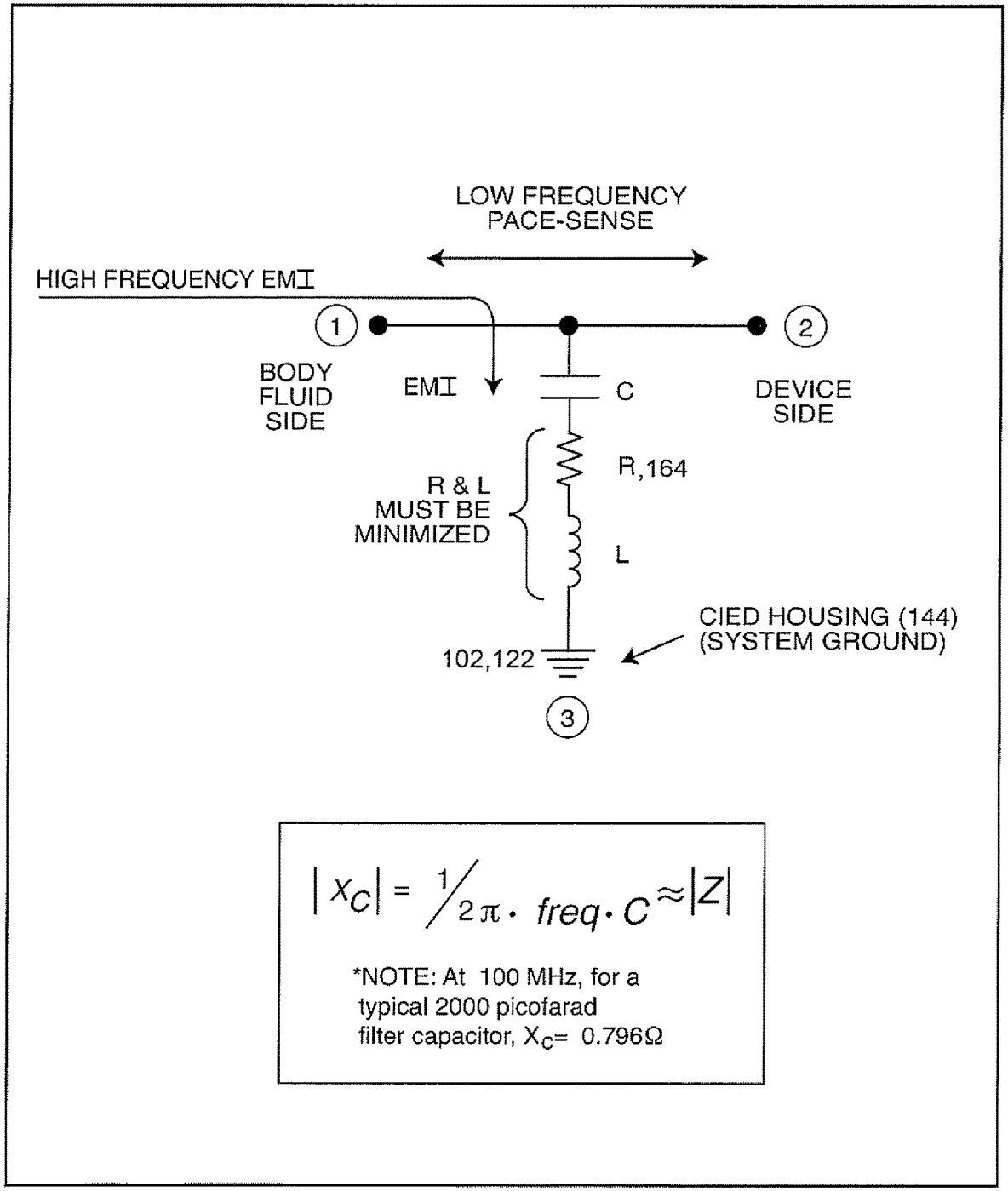
FIG. 6H is an electrical schematic showing incident and diverted EMI through a filter capacitor of an AIMD.
Figure 6I:
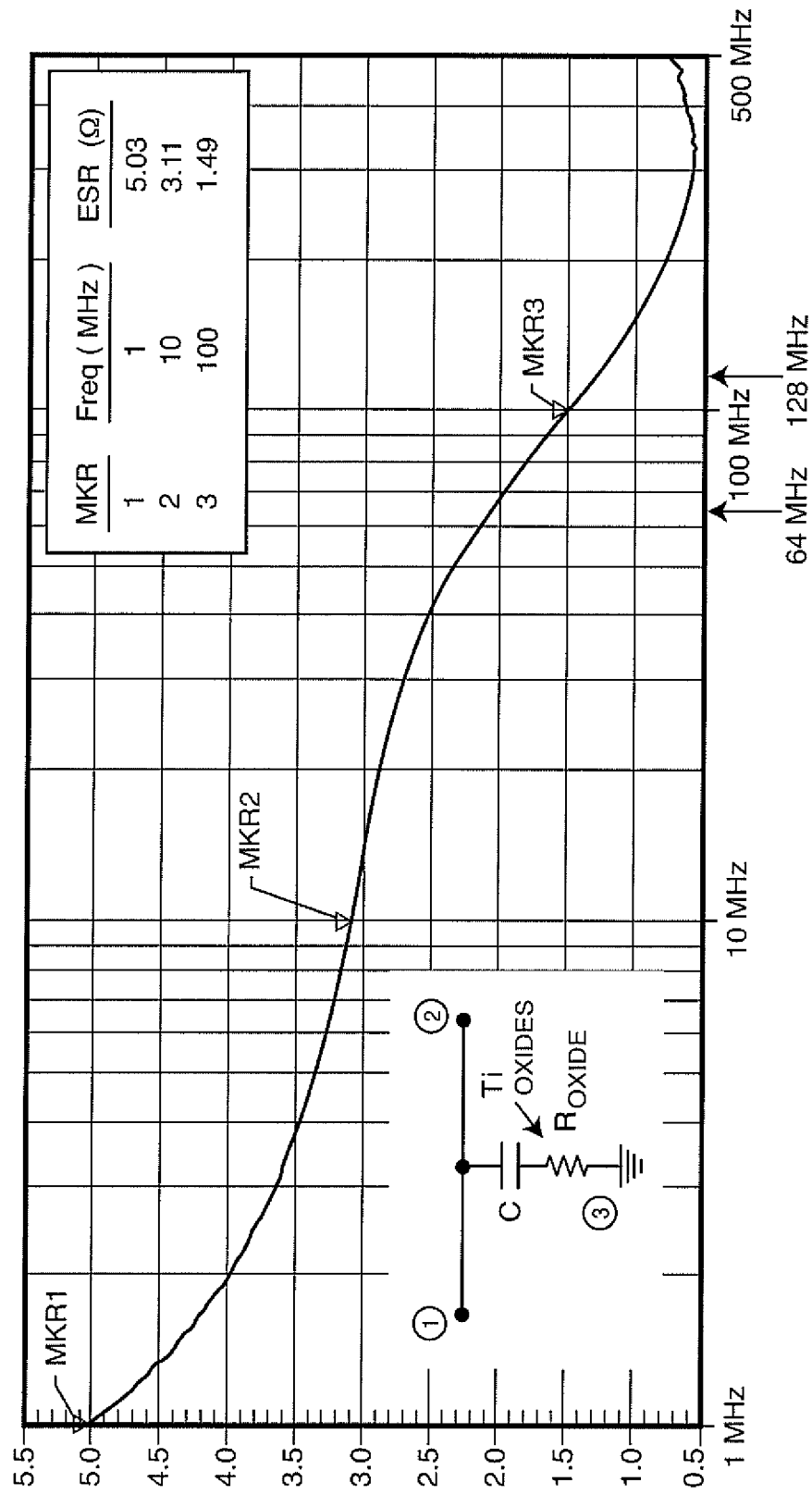
FIGS. 6I and 6J show the ESR curve vs. frequency of a highly oxidized EMI filter electrical connection.
Figure 6J:
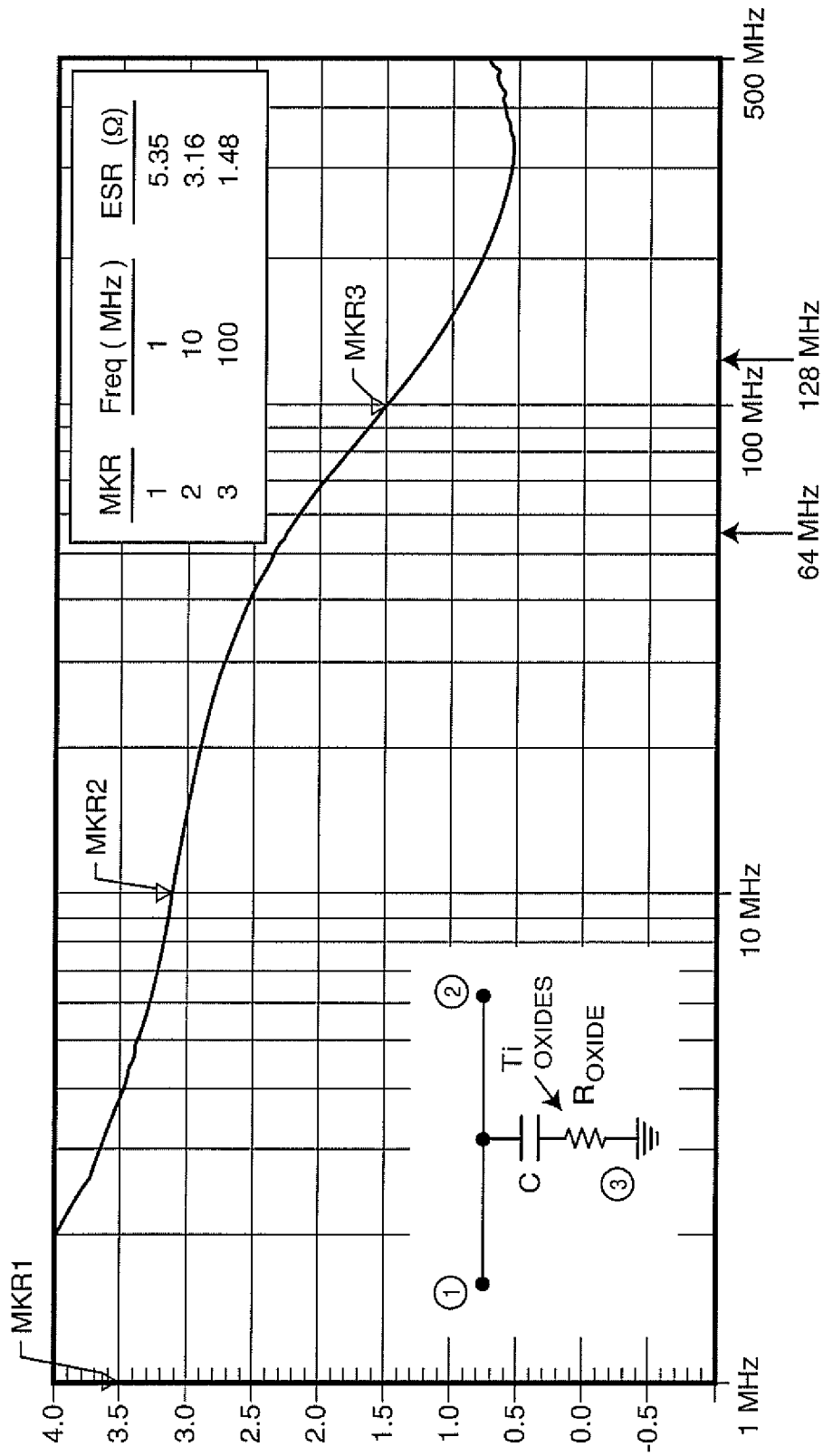
Figure 6K:
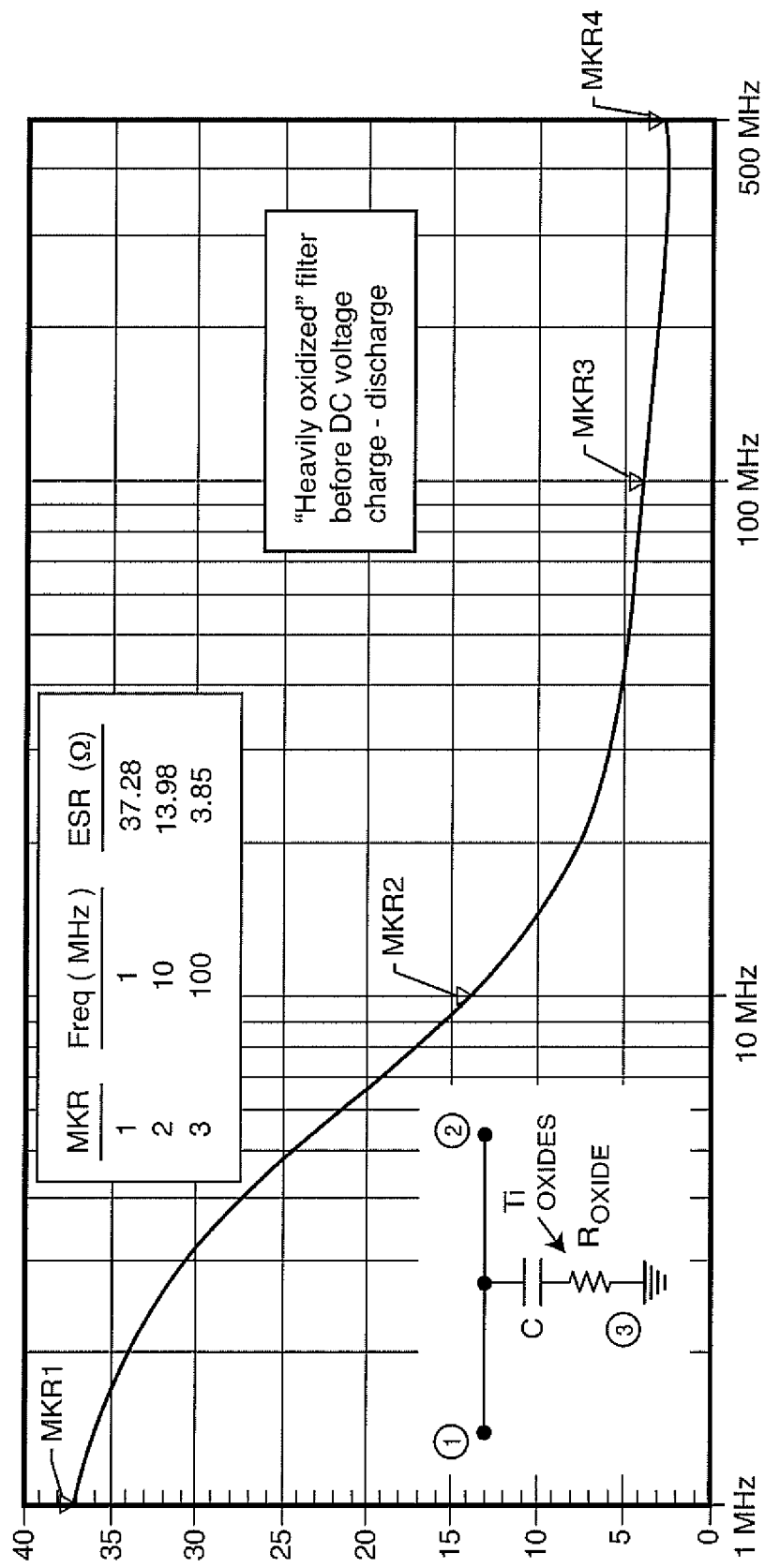
FIG. 6K shows the ESR curve vs. frequency of a very badly oxidized filter connection (filter performance highly degraded).

FIG. 6H is a schematic diagram indicating how high frequency EMI entering from a body fluid side (terminal 1) is diverted through a feedthrough filter capacitor or filter capacitor C. For the filter capacitor to work properly, its parasitic resistance $R_{OXIDE}$ 164 must be eliminated or minimized. If the resistance value $R_{OXIDE}$ 164 becomes too large, then the filter performance is seriously compromised. Ideally, high frequency EMI is diverted to system ground 144 (terminal 3) as indicated. However, if the resistance 164 due to oxides ($R_{OXIDE}$) form, then filter performance is degraded, and a significant amount of high frequency EMI enters into the device at terminal 2. When R and L are minimized, then the capacitive reactance $X_C$ will approximately be equal to the impedance Z, as indicated in the equation of FIG. 6H. Referring once again to FIG. 6H, one will appreciate that the inductance L that is indicated is zero for a coaxial three-terminal feedthrough filter capacitor. This is due to the unique geometry of feedthrough filter capacitors that are best understood as a high frequency transmission line model. So, referring once again to FIG. 6H, if one eliminates resistance $R_{OXIDE}$ 164 due to titanium surface oxides and uses a feedthrough filter capacitor geometry, then one has an ideal filter capacitor C, which diverts a maximum amount of high frequency unwanted and dangerous EMI to the CIED device housing system ground 144. This prevents the dangerous EMI from entering into the AIMD housing 102 at terminal 2.

Figure 11:
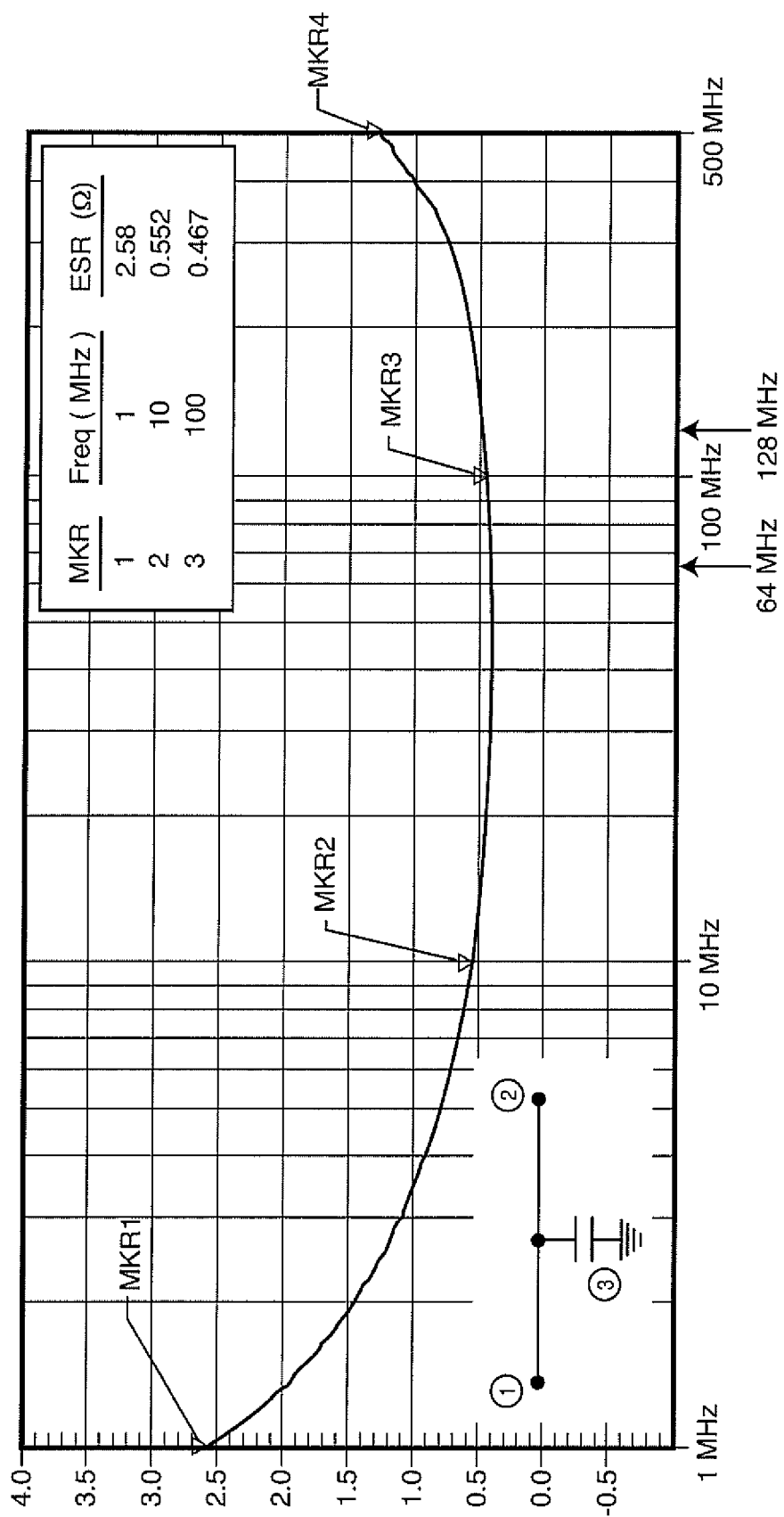
FIG. 11 is the ESR curve vs. frequency of the quadpolar filter of FIG. 9, illustrating greatly reduced ESR due to the elimination of oxides in the filter system ground connection.
Figure 12:
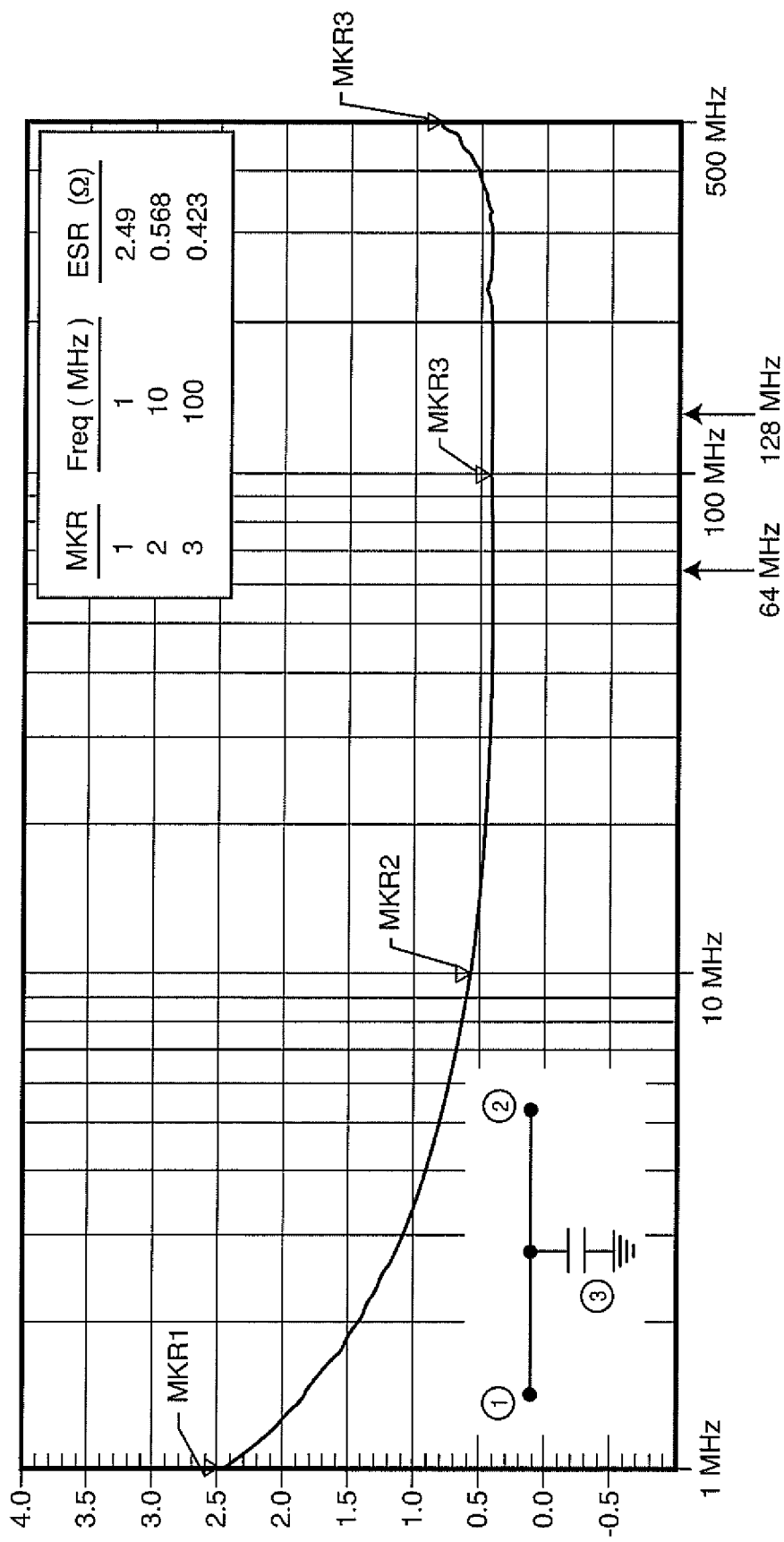
FIG. 12 is similar to FIG. 11 and illustrates how hundreds of filters from multiple manufacturing lots overlay like fingerprints. Importantly, the ESR curve s U-shaped.

FIGS. 6I, 6J and 6K are graphs of the equivalent series resistance (ESR) of feedthrough filter capacitors versus frequency. What is alarming is that the expected U-shaped ESR curve of these particular feedthrough filter capacitors are not present. In contrast, FIGS. 11 and 12 illustrate a proper and expected ESR vs. frequency curve for a feedthrough filter capacitor that is correctly connected to an unoxidized or unoxidizable surface. The U-shaped curve, at low frequency, comes from the dielectric loss tangent of the capacitor ceramic dielectric, which is very high at low frequency (1 kHz) and then drops to near zero at frequencies above 10 MHz. At the bottom of the U-shaped curve, one sees the ESR (ohmic loss) of the feedthrough filter capacitor itself, which when R and L are both eliminated, represents the ESR of the capacitor's internal electrode plates and internal connections to the feedthrough filter capacitor's active and ground metallizations. At high frequency (generally above 500 MHz), the curve has a rising slope again, which is an artifact of a two-terminal measurement apparatus used to measure ESR. At very high frequency, skin effect comes into play, which shows that the ESR is increasing. However, when properly installed as a three-terminal device, this skin effect does not happen. Referring once again to FIGS. 6I, 6J and 6K, what is particularly alarming at the high values is the ESR of these capacitors, for example, at 100 MHz (1.49 ohms and 1.48 ohms). This much oxide-created resistance seriously degrades EMI filter performance and is dangerous, as sensitive AIMD circuits could be disrupted, even fail to work. As mentioned previously, in an MRI environment where the amount of RF current to be diverted is very high, such a high filter ESR also creates a great deal of heat in the filter capacitor ground connection, which then further leads to more and/or thicker oxides. As previously mentioned, titanium oxides form faster at elevated temperatures. Even more alarming are the high values of ESR for these two capacitors at 100 MHz (1.49 ohms and 1.48 ohms). It is emphasized that ESR sweeps identified five discrepant oxidized parts from a lot of 1000 prototype filtered feedthrough parts, and that this lot of filtered feedthrough parts were built with a thermal-setting conductive adhesive (ECA) directly connecting the capacitor ground termination 132 of the EMI filter capacitor 124 and the feedthrough ferrule 122. The three hermetic feedthrough filter assemblies represented by the graphs of FIGS. 6I, 6J and 6K are taken from the group of five filters that exhibited the dangerously high ESR.

FIG. 6K illustrates an ESR versus frequency curve of the most oxidized part of the five parts in the 1000-piece qualification test lot that failed. In this case, the ESR at 100 MHz is 3.85 ohms. Referring back to FIG. 6C, the capacitive reactance at 100 MHz for a typical 2000 picofarad filter capacitor is 0.796 ohms. One can see that when a surface oxide layer 164 causes an increased resistance ($R_{OXIDE}$) in series with a filter capacitor from less than one ohm to 3.85 ohms, then the filter performance of that particular filter capacitor seriously and dangerously degrades, even fails to filter. Referring once again to FIG. 6K, the inventors took this heavily oxidized feedthrough filter capacitor and charged it to 100 volts DC. The inventors then literally shorted the part with a paper clip causing a high current pulse, incredibly, the ESR curve of FIG. 6K became that of a normal filtered capacitor ESR curve, such as illustrated herein by FIGS. 11 and 12. This amazed the inventors at first, however, after having let the filter sit at room temperature for 3 or 4 days and then re-analyzing the filter, the high ESR came right back to the graph of FIG. 6K. It is now understood that titanium oxides are not just resistive, they also exhibit very bizarre semi-conductor behavior (which results in highly unstable ESR and a completely unreliable EMI filter).

Figure 7:
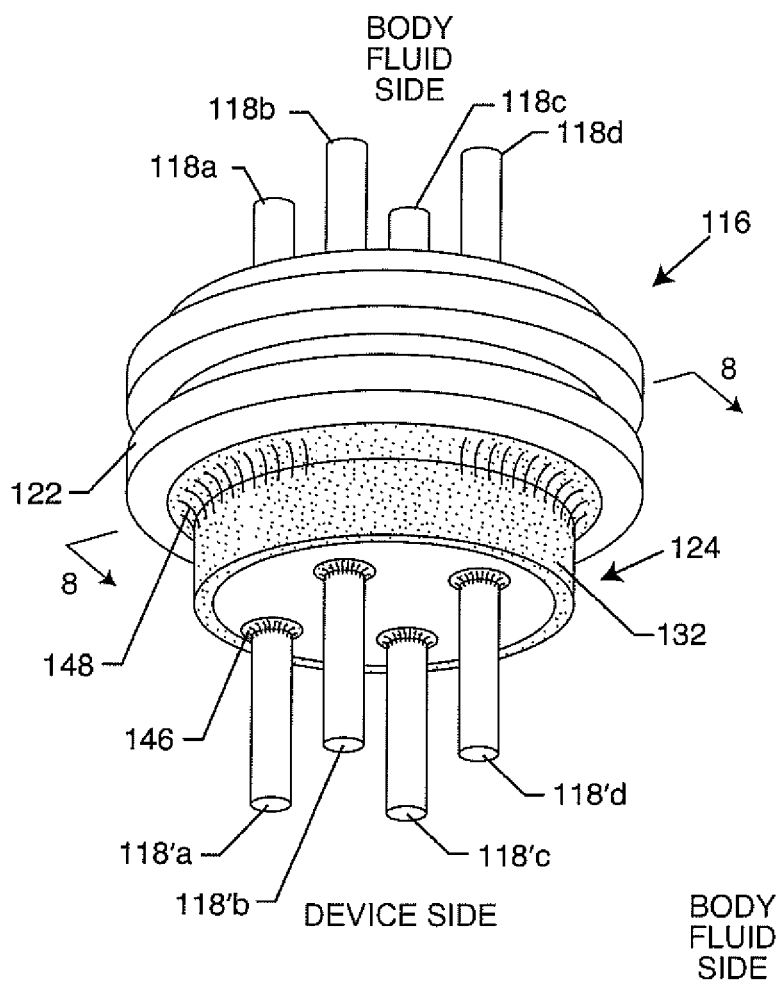
FIG. 7 is a perspective view of a quadpolar filter feedthrough assembly comprising a feedthrough capacitor and a hermetic terminal assembly.

FIG. 7 illustrates a quadpolar feedthrough filter capacitor and hermetic feedthrough terminal subassembly 116 (a filtered feedthrough assembly) comprising four leadwires 118a-118d and four feedthrough holes (quadpolar). The hermetic terminal is a metallic ferrule 122 generally of titanium, which is ready for laser welding 128 into the AIMD housing 102 (not shown).

Figure 8:
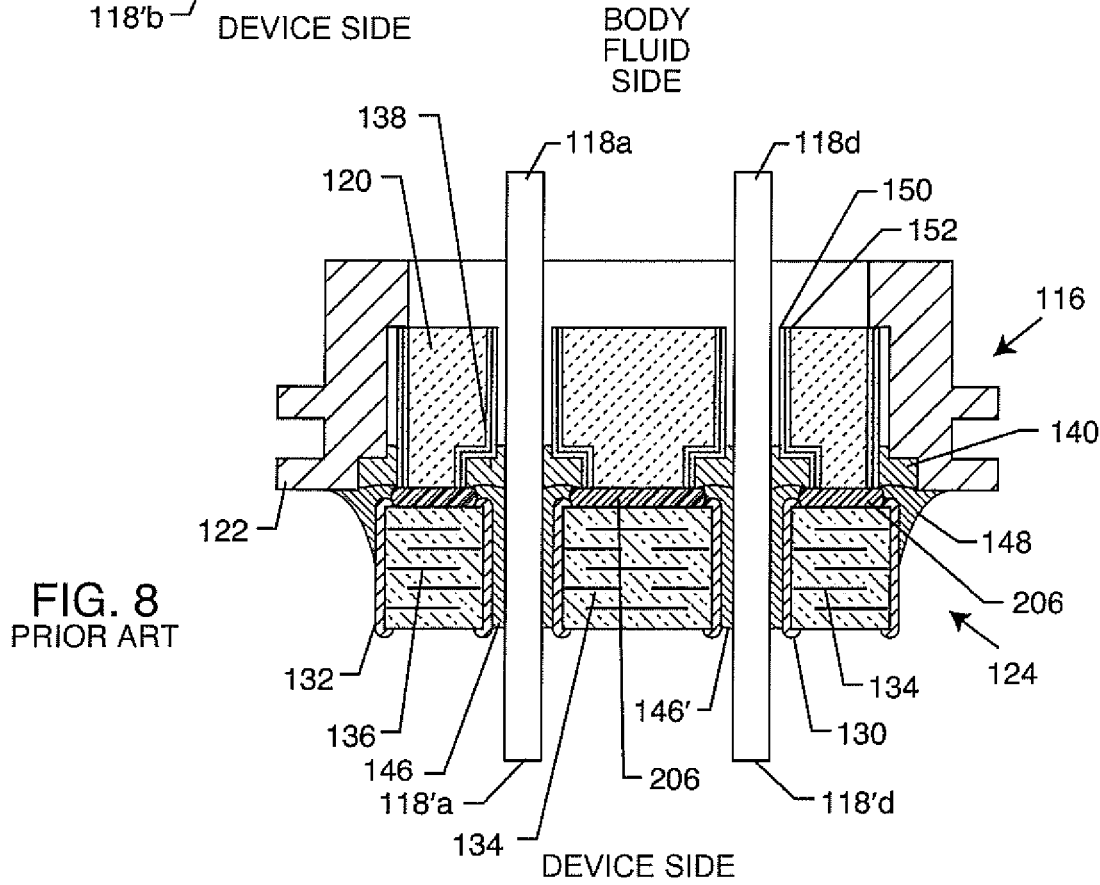
FIG. 8 is a sectional view of the hermetic filter feedthrough terminal assembly of FIG. 7 taken along lines 8-8, illustrating the ground connection of the EMI filter to a ferrule oxide-resistant gold braze hermetic seal.

Referring once again to FIG. 7, illustrated is a prior art embodiment of an oxide-resistant connection to the capacitor ground metallization using an electrical connection material 148. In this case, the electrical connection is not made directly to the feedthrough ferrule 122. This is best understood by looking at FIG. 8, which is a cross-sectional view taken from section 8-8 of FIG. 7. FIG. 8 illustrates that the electrical connection material 148 electrically connecting the capacitor ground termination 132 and the ferrule is at least partially contacting the gold braze 140 that hermetically seals the insulator 120 and the ferrule 122. An electrical connection to an oxide-resistant material, which includes oxide-resistant metals, for example, a gold braze as shown, provides a very low resistance connection that is essentially free of oxides. Connection to the gold braze of the hermetic seal is further described in U.S. Pat. No. 6,765,779, the content of which is herein incorporated fully by this reference.

FIG. 8 is a prior art sectional view taken generally from section 8-8 from FIG. 7. The hermetic terminal subassembly leadwires 118a-d pass through the hermetic terminal subassembly insulator 120 in non-conductive relationship and also pass through the feedthrough capacitor 124, wherein the active electrode plates 134 are electrically connected 146 to the hermetic terminal subassembly leadwire 118 and wherein the feedthrough capacitor ground electrode plates 136 are electrically connected 148 to the hermetic terminal subassembly ferrule 122 and the gold braze 140.

Referring once again to FIGS. 7 and 8, in each case it is seen that the hermetic terminal subassembly leadwires 118a-d pass all the way through the entire structure, namely, the hermetic terminal subassembly 116 and the feedthrough filter capacitor 124. In general, these hermetic terminal subassembly leadwires 118a-d are electrically and mechanically continuous (single material) and pass through from the body fluid side to the inside of the device 100 housing 102. However, electrical and mechanical continuity can also be achieved by a two-part pin (118" of FIG. 30), a combination of a pin and a sintered paste-filled via (118' of FIG. 30), or a metal insert in a co-sintered paste-filled via (not shown). Because the hermetic terminal subassembly leadwires 118a-d pass through from the body fluid side to the inside of the device housing by way of header block connector assembly 104 or the like, it is very important that these hermetic terminal subassembly leadwire 118 materials be biocompatible, biostable and non-toxic. Generally, in the prior art, these hermetic terminal subassembly leadwires are constructed of platinum or platinum-iridium, palladium or palladium-iridium, niobium or the like. Platinum-iridium is an ideal choice because it is biocompatible, non-toxic and is also mechanically very strong. The iridium is added to enhance material ductility and to enable the hermetic terminal subassembly leadwire to sustain bending stresses. The above mentioned leadwire materials are typically not oxidized, or only have a low oxidization level, and are solderable. It is appreciated that most prior art hermetic terminal subassembly leadwires 118 are electrically and mechanically continuous (single material). However, it will also be appreciated that these leadwires 118 can be a 2-part or a multi-part leadwire, as taught by U.S. Pat. No. 10,589,107, the contents of which are incorporated herein fully by reference. While a single continuous leadwire is commonly used, the two-part pin, combination pin and sintered paste and the co-sintered metal insert novel leadwire options provide the option to replace at least a portion of the single material continuous leadwire with a low cost biocompatible terminal pin two-part pin design, or replace the entire leadwire with a low cost biocompatible terminal pin sintered past combination or a co-sintered paste comprising a low cost biocompatible metal insert, wherein the low cost biocompatible material comprises, but is not limited to, tantalum (Ta), niobium (Nb), molybdenum (Mo), titanium (Ti), 52 alloy, stainless steel, among others. The use of Ta, Nb, Mo or Ti terminal pins are generally counterintuitive/contraindicated because these materials readily oxidize, thus forming a direct low resistance connection with a solder or an ECA to the via hole metallization connected to the MLCC active trace can't be accomplished in an oxide-free low resistance manner. However, electrical connection to an oxide-resistant coating of the present invention resolves this issue. For example, an electrical connection may be made using an optional ECA or a solder directly from the circuit trace active via hole of an AIMD circuit board and to an oxide-free gold braze hermetically sealing the feedthrough low cost leadwire, thereby connecting the low cost active terminal pin(s) to the active circuit trace of the AIMD circuit board in an oxide-free manner without even needing to connect to the low cost terminal pin option at all. In the case of the sintered and co-sintered structures, the electrical connection is made to the circuit trace active via hole of an AIMD circuit board either to an oxide-resistant electrically conductive material sintered/co-sintered paste filling the feedthrough via or to an oxide-resistant coating applied to the low cost pin or insert portion of the sintered/co-sintered active via. In addition, for expensive Pt and Pd pins (typically alloyed with a percentage of iridium to increase resistance to bending and fatigue), it is important to note that the iridium of the alloy can migrate to the terminal pin surface where it oxidizes, thereby impeding both solderability of the terminal pin and/or the low ESR connection. In summary, attachment from the circuit board via hole directly to the gold braze of the hermetically sealed feedthrough or to an oxide-resistant paste material filling a sintered/co-sintered via of the hermetically sealed feedthrough or an oxide-resistant coated low-cost pin or metal insert of the hermetic feedthrough sintered/co-sintered via enables the use of low cost Ta, Nb, Mo, Ti or the Pt and Pd terminal pins alloyed with iridium. Such an electrical connection to gold braze and/or an oxide-resistant coating prevents latent oxidation and ESR defects (meaning that the electrical connection is stable and reliable long term). Referring once again to FIGS. 7 and 8, it is also noted that by connecting the capacitor ground termination 132 to gold braze 140, the outside diameter of the feedthrough capacitor is thereby constrained, which can make the feedthrough capacitor volumetrically inefficient.

Figure 9:
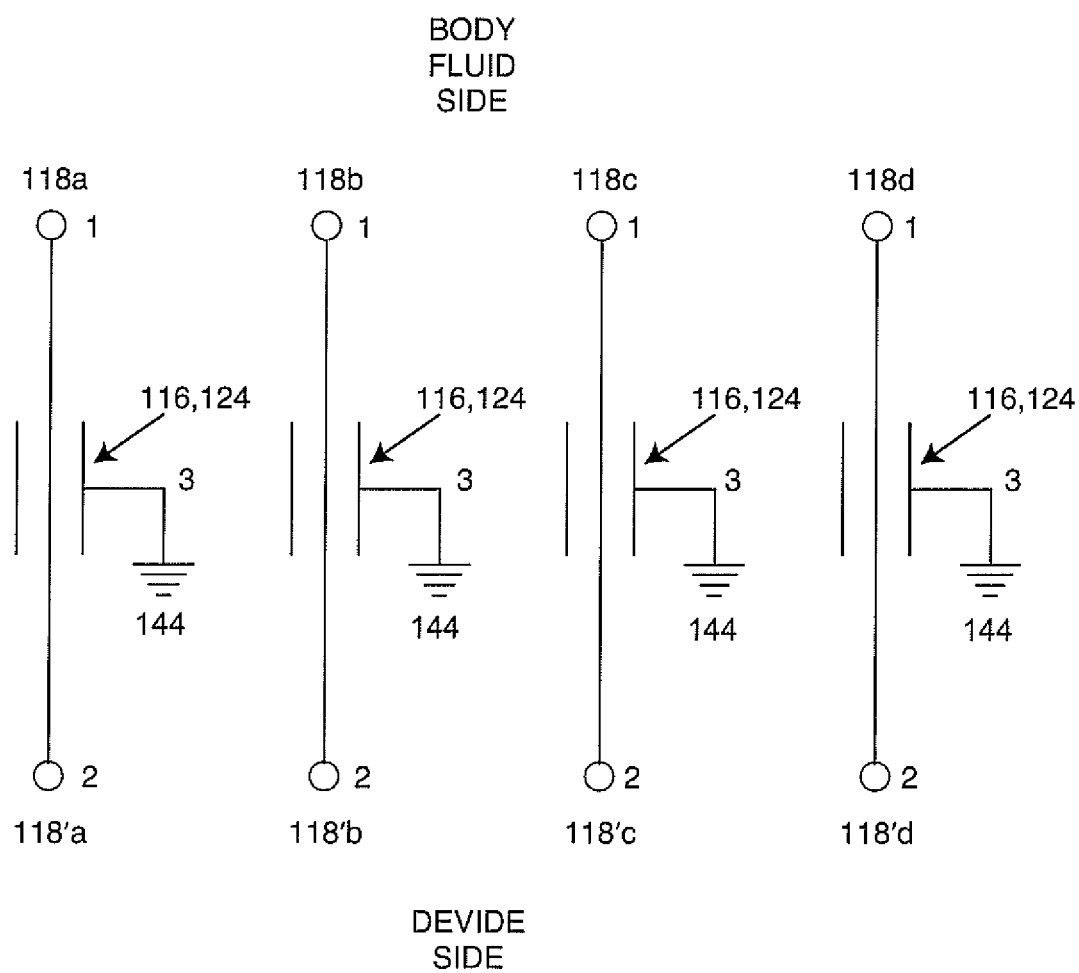
FIG. 9 is an electrical schematic representation of the quadpolar filter feedthrough capacitor of FIGS. 7 and 8 having an oxide-free connection.

FIG. 9 illustrates the schematic of the quadpolar hermetic terminal of FIG. 7. The schematic shows the feedthrough filter capacitors grounded to system ground without series inductance or resistance. The reason inductance is absent is because feedthrough capacitors are unique in that they are three-terminal devices that do not have series inductance. More importantly, the reason that the resistance is absent is because the ESR of the feedthrough capacitor is so low because the capacitor ground is electrically connected to (directly contacts) the hermetic seal insulator to ferrule gold braze, as illustrated in FIG. 8; thus, the resistance 164 is essentially eliminated and can be ignored. In other words, FIG. 9 illustrates that the feedthrough capacitor of FIGS. 7 and 8, exhibits nearly ideal filter performance.

Figure 10:
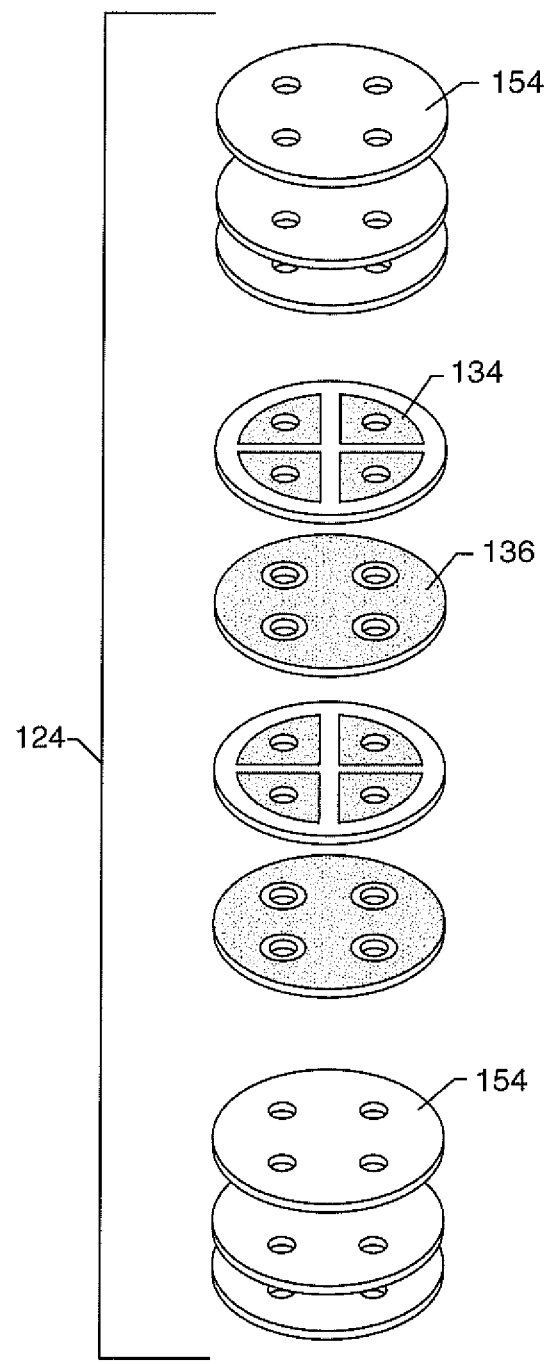
FIG. 10 is an exploded perspective view of the electrode layer stack up of the filter structure of FIGS. 7 and 8.

FIG. 10 is an exploded view of the quadpolar filter capacitor 132 of FIG. 7. In the exploded view, shown are four active electrode plates 134 and one ground plate 136. The overlap of the active electrode 134 with the ground electrode 136 determines the effective capacitance area. The greater this overlap area, the higher the capacitance of the feedthrough filter capacitor. One can also say that this quadpolar filter capacitor 132 is a multilayer structure. In FIG. 10, there are two active and two ground plates shown. Increasing the number of active and ground plates has the effect of increasing the capacitor's effective capacitance area. It is appreciated that as many as 400 or more ground and active layers can be used.

FIGS. 11 and 12 are ESR versus frequency curves for ESR sweeps of the EMI filter capacitor 124 of FIGS. 7 and 8, wherein the electrical connection 148 of the EMI filter capacitor 124 to the ferrule 122 is made directly to the gold braze 140 hermetically sealing the insulator 120 and the ferrule 122 of the hermetic terminal 116. In this case, the ESR at 100 MHz is 0.467 ohms and 0.423 ohms. More importantly, the curves of FIGS. 11 and 12 exhibit the expected classic capacitor U-shaped ESR curve. A U-shaped ESR curve is "the fingerprint" for a filter capacitor and each curve should overlay one another. The reason the ESR increases at low frequency is due to the normal behavior of the capacitor's dielectric loss tangent. At higher frequencies, above 10 MHz, the dielectric loss tangent starts to diminish and the ESR curve is dominated by ohmic loss. The U-shaped curve at high frequencies, such as 500 MHz, is an artifact of a two-terminal measurement for ESR. As previously disclosed, the increase in ESR at 500 MHz is due to skin effect. The most important performance parameter of an EMI filter is the measurement of insertion loss (IL). IL is measured on a spectrum or network analyzer at swept frequencies. It is appreciated that, within a filter IL fixture, RF leakage or reflections are minimized, and the insertion loss and even the impedance can be measured with a Vector Network Analyzer (VNA). For all insertion loss measurements, careful fixture design is critical. A paper given by co-inventor, Robert Stevenson was presented at the 1996 Capacitor and Resistor Technology Symposium (CARTS), Mar. 11, 1996, Monteleone Hotel, New Orleans, LA. This paper was done in cooperation with the IEEE and the Microelectronics Society (IHSN). The paper has an ISSN No: 0887-0491. The title of the paper is "Approved EMI Filter Insertion Loss Test Methods, Equipment and Fixtures." The paper was co-authored by Robert A. Stevenson and Mike Lowder. This paper details the design principles that must be followed for a proper high-frequency insertion loss fixture. The 1996 CARTS paper is incorporated herein fully by this reference. The IL tests indicate that the EMI filters of FIGS. 11 and 12 have ideal IL in decibels (dB) of 28.82 dB (ESR 0.467 ohms) and 29.08 dB (ESR 0.422 ohms). One is reminded that insertion loss is a decibel scale, which is logarithmic. A drop-in insertion loss of 6 dB will degrade filter performance by half. For the heavily oxidized filters of FIGS. 6D, 6E and 6F, insertion loss severely degrades. Even a drop of 3 dB is a still a significant drop in filter performance. With a 100 MHz ESR of 1.48 ohms (due to $R_{OXIDE}$ 164), the insertion loss is 23.95 dB. For an ESR of 1.49 ohms at 100 MHz, the insertion loss is 23.91 dB and for the worst part out of this test population that had an ESR of 3.86 ohms at 100 MHz, insertion loss drops to 17.3 dB. Drops in insertion loss like this means that filter performance is very badly degraded, meaning that filter performance is compromised creating a situation that can be very dangerous or even life-threatening for an CIED patient. A comparison of filter capacitor electrical data is shown below in Table 2 below:

TABLE 2

| | Filter Capacitor Electrical Data @ 100 MHz | | | |
|---|---|---|---|---|
| Filter | Oxidized Titanium Surface* | | Oxide-Resistant Surface** | |
| Attachment | ESR | IL | ESR | IL |
| Sample 1 | 1.48 Ω | 23.95 dB | 0.467 Ω | 28.82 dB |
| Sample 2 | 1.49 Ω | 23.91 dB | 0.422 Ω | 29.08 dB |
| Sample 3 | 3.86 Ω | 17.30 dB | | | where: ESR = Equivalent Series Resistant
IL = Insertion Loss
*see FIGS. 6D and 6E
**see FIGS. 6J and 6K FIGS. 13A, 13B and 13C illustrate an internally grounded prior art feedthrough filter capacitor. In general, internally grounded feedthrough capacitors are known in the prior art with reference to U.S. Pat. Nos. 5,905,627; 6,529,103; 6,765,780 and the like, all of which are fully incorporated herein by these references. Referring once again to FIG. 13A, one can see an internally grounded feedthrough capacitor, 124' which is octapolar (eight active leads). The eight active leads are labeled 118a through 118h on the body fluid side and on the device side (inside) of the AIMD housing the eight active leads are labeled 118'a through 118'h. The ferrule 122 has a peninsula structure 139, which is electrically connected to an internal ground pin 118gnd. Referring now to the octapolar feedthrough capacitor active electrode plates 134, these active electrode plates are designed to overlay the ground electrode plates 136 in a sandwich-like fashion (interleaved). One skilled in the art will realize that one can stack up as many of these interleaved layers as is required in order to achieve the required capacitance value and other design factors. The internal ground lead 118gnd is electrically connected to the ground electrode plate layers 136. The active electrodes 134a through 134h are each electrically connected through their respective leadwires 118'a through 118'h to the active electrode plates. The overlap between the active electrodes 134 and the ground electrodes 136 creates what is known as effective capacitance area. The active and ground electrode layers may be interleaved with additional ceramic layers to build up the dielectric thickness (not shown). In general, the monolithic ceramic feedthrough capacitor 124 as shown in FIG. 6 is a result of laminating the various electrode layers together and then sintering them at a high temperature to form a rigid monolithic ceramic block. This is known as a single feedthrough capacitor that is multipolar (in this case the feedthrough capacitor is octapolar or has eight active filter circuits). Unlike the perimeter metallization 132 on the outside of the round capacitors of FIGS. 3 and 7, the octapolar filter capacitor of FIG. 6 has no perimeter metallization 132 at all.

There are several major advantages to internal grounding without a capacitor perimeter or diameter metallization 132. This is best understood by referring back to FIGS. 3 and 7. In contrast to FIGS. 3 and 7, an internal ground filter capacitor as shown in FIGS. 13A, 13B and 13C no longer requires a diameter or perimeter metallization 132 for an electrical ground connection. In addition, the electrical connection 148 has been entirely eliminated between the capacitor diameter metallization 132 and the gold braze 140 and ferrule 122. The elimination of this electrical connection 148 also makes the capacitor structure 124' much more resistant to mechanical damage caused by subsequent laser welding 128 of the hermetic seal assembly 116 into the AIMD housing 102. A significant amount of heat is produced by laser welding 128 and there is also a mismatch in thermal coefficient of expansion (TCE) between some of the different materials of construction. By elimination of the electrical connection material 148, the capacitor 124' is free to float and is therefore much more resistant to such TCE induced stresses. Referring once again to FIG. 13B, one can see that the internal ground lead 118'gnd makes a low impedance connection from the capacitor's internal ground electrode plates 136 to the ferrule 122. This is what eliminates the need for the electrical connection material 148 of FIGS. 3 and 7. It is appreciated that only one ground pin is shown in FIGS. 13A, 13B and 13C, however, some designs may require a multiplicity of ground pins spaced apart such that, there is a very low impedance connection effectively grounding the capacitor internal ground electrodes 136 at multiple points.

Referring once again to FIG. 13B, one can see that the ceramic capacitor subassembly 124' is ready to be installed onto the hermetic terminal subassembly 189. These are shown joined together in FIG. 13C resulting in a hermetically sealed feedthrough capacitor filter assembly 116.

Referring back to FIG. 13B, it is important to clarify some confusion in terms of art. The feedthrough capacitor 124' can also be described as a three-terminal feedthrough capacitor with multiple via holes or feedthrough holes. In a confusing manner, the hermetic terminal subassembly 189 is often referred to in the art as a hermetic feedthrough. Therefore, we have the term feedthrough applying both to the feedthrough capacitor and to the hermetic terminal assembly. As used herein, these are two separate and distinct subassemblies, which are assembled together in FIG. 13C to become a feedthrough filter hermetic terminal assembly 116, which is ready for installation into an opening of an AIMD housing. Referring once again to FIGS. 13A and 13B, one will appreciate that leadwires or lead conductors 118', 118 are continuous leadwires. In other words, on the body fluid side, the leadwire is of the same material as on the device side. This is typical in the prior art; however, as previously disclosed, the leadwire may alternatively comprise a two-part pin, a combination of a pin and a sintered paste-filled via, or a metal insert in a co-sintered paste-filled via. Referring once again to FIG. 13B, one can see that the internal ground lead 118'gnd does not (but may) extend through to the body fluid side of the hermetic terminal feedthrough subassembly 189. It is appreciated that it can be easily and readily extended to the body fluid side, but in most embodiments, it is not necessary.

An issue with the use of platinum for hermetic terminal subassembly leadwires 118*a*-*d* is that platinum has become extremely expensive and may be subject to premature fracture under rigorous processing such as ultrasonic cleaning or application use/misuse, and possibly unintentional damaging forces resulting from Twiddler's Syndrome. Accordingly, what is needed is a filtered structure like a feedthrough capacitor assembly 116, which eliminates these high-priced platinum, platinum-iridium or equivalent biocompatible metal hermetic terminal subassembly leadwires 118. For additional examples of hermetic terminal subassemblies with feedthrough capacitors that employ leadwires 118, one is referred to U.S. Pat. Nos. 5,333,095, 5,896,267, 5,751,539, 5,905,627, 5,959,829, 5,973,906, 6,008,980, 6,159,560, 6,275,379, 6,456,481, 6,529,103, 6,566,978, 6,567,259, 6,643,903, 6,765,779, 6,765,780, 6,888,715, 6,985,347, 6,987,660, 6,999,818, 7,012,192, 7,035,076, 7,038,900, 7,113,387, 7,136,273, 7,199,995, 7,310,216, 7,327,553, 7,489,495, 7,535,693, 7,551,963, 7,623,335, 7,797,048, 7,957,806, 8,095,224, 8,179,658 the contents of all of which are fully incorporated herein by reference.

Figure 13D:
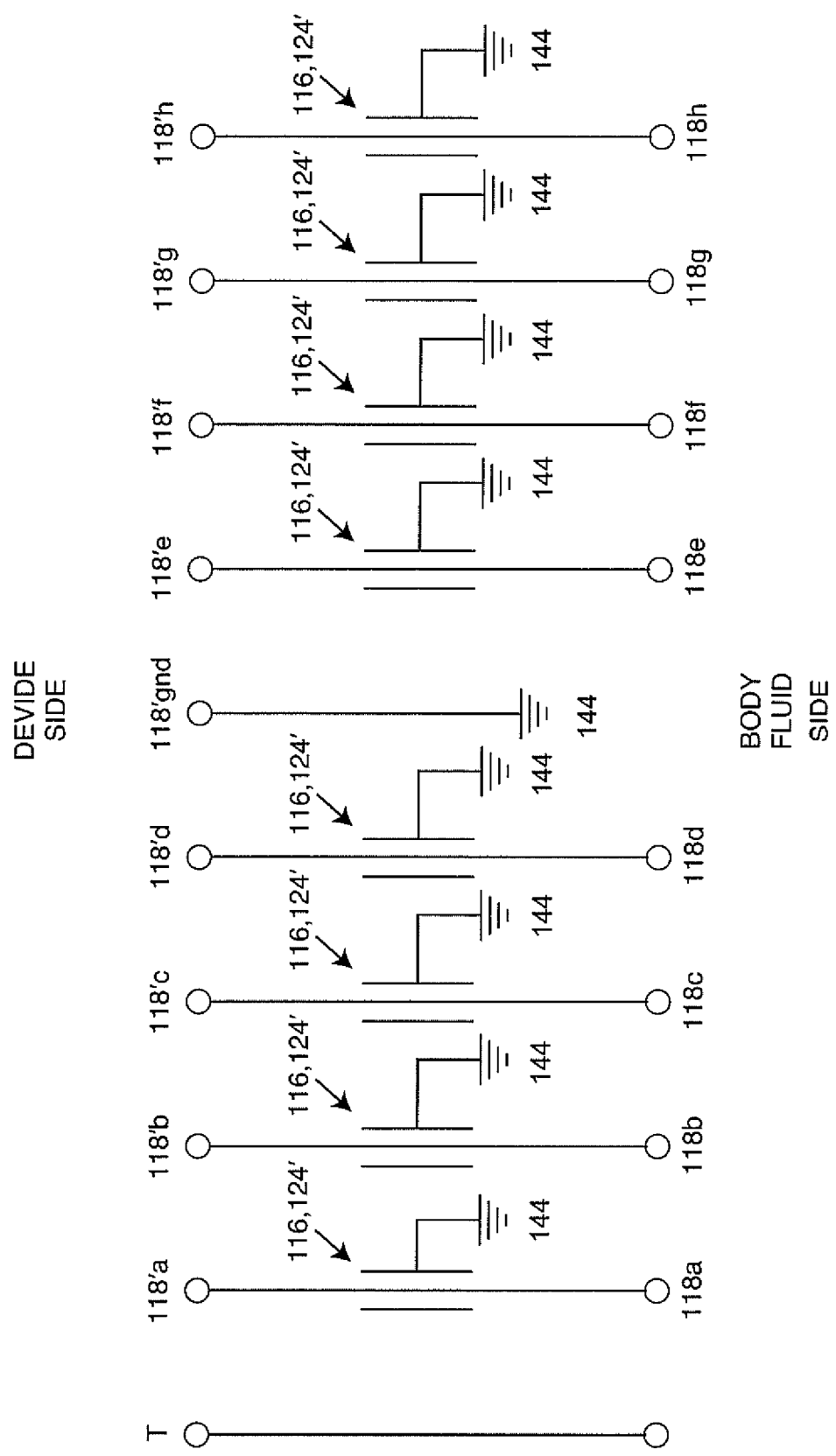
FIG. 13D is the electrical schematic of the hermetically sealed filter feedthrough terminal of FIG. 13C.

FIG. 13D is the electrical schematic for the feedthrough filtered hermetic terminal assembly 116 of FIGS. 13A, 13B and 13C. Referring once again to FIG. 13D, one can see the telemetry pin T, which passes through the filtered hermetic terminal assembly 116, is without any appreciable capacitance to ground. In other words, it would be undesirable to have any high frequency filtering of the telemetry terminal since this would preclude the ability to recover stored information or program the AIMD device remotely. Leadwires 118*a* through 118*h* all have feedthrough capacitor hermetic terminal assemblies 116, 124' as shown. The internal ground pin 118gnd is shown only on the device side of the hermetic terminal subassembly 189. Referring once again to FIGS. 13A, 13B, 13C and 13D, it is noted that the capacitor 124 is on the device side of the AIMD.

Referring once again to the internally grounded feedthrough capacitor illustrated in FIGS. 13A, 13B and 13C, the ground connection is through an internal ground pin 118'gnd. This ground pin is ideally of platinum or similar biocompatible material that is highly resistant to oxidation. Referring to the schematic diagram of FIG. 13D, it is noted that, once again, the EMI filter has no resistance ($R_{OXIDE}$ 164) in the system ground 144 electrical connection 102, 122, and behave essentially as ideal filters. Referring once again to the internally grounded filter of FIGS. 13A, 13B and 13C, it is important to note that the single ground pin 118'gnd central to an elongate feedthrough capacitor as shown can cause undesirable inductance L build-up across the feedthrough capacitor ground electrode plates. In order to overcome this effect, several internal ground pins 118'gnd can be added. Another way to look at this is that pins closest to the internal ground pin 118' would have a higher insertion loss IL, in comparison to the pins most distant from it, such as pin 118'*h*.

Figure 14:
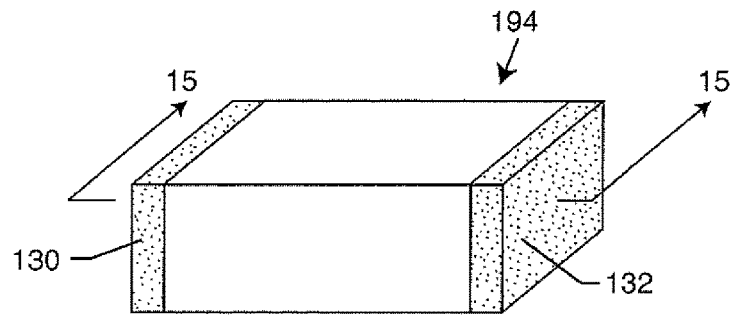
FIG. 14 illustrates a prior art monolithic ceramic capacitor (MLCC), which is also known in the art as a multilayer ceramic capacitor.

FIG. 14 illustrates the prior art monolithic ceramic capacitor 194 previously disclosed herein in FIG. 6L. Monolithic ceramic chip capacitors 194, which are also commonly referred to as multilayer ceramic capacitors or MLCC chip capacitors, are very well known in the prior art and are produced daily in the hundreds of millions. MLCC chip capacitors 194 are common components in most electronic devices, including computers, electronic tablets, modern smart phones and the like. It is noted that not all rectangular two-terminal capacitors, as illustrated in FIG. 14, must be ceramic. As used herein, MLCC ceramic chip capacitors include all kinds of stacked tantalum, stacked film and other dielectric type capacitors that form two-terminal rectangular shapes. It is appreciated that any of the two-terminal capacitors in the art, including ceramic, film and tantalum, can also have other shapes other than rectangular, including round, oval, flat, cylindrical and the like.

Figure 15:
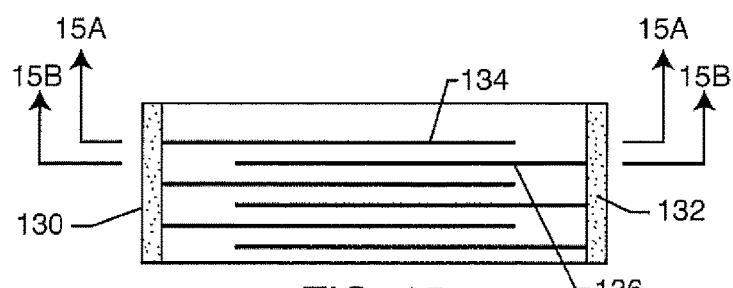
FIG. 15 is a sectional view of the MLCC chip capacitor of FIG. 14 showing its internal electrode plates.
Figure 15A:
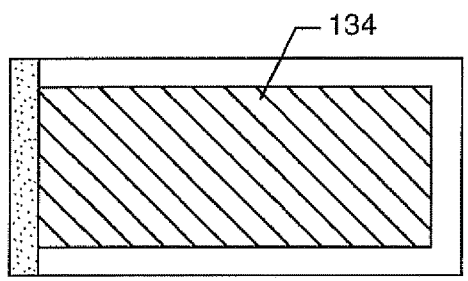
FIG. 15A is a top sectional view of the MLCC chip capacitor showing its left-hand active electrode plates.
Figure 15B:
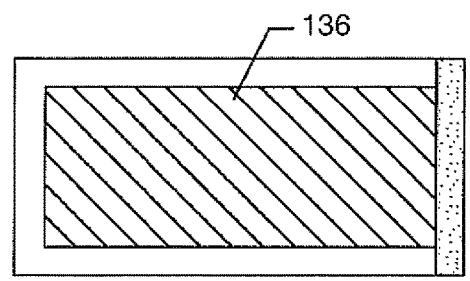
FIG. 15B is a similar sectional view to FIG. 15A, except in this case, showing the right-hand connected active electrode plates.

FIG. 15, taken from section 15-15 of FIG. 14, illustrates a cross-section of an MLCC chip capacitor 194. As can be seen, the prior art MLCC chip capacitor 194 is a two-terminal device having a metallization 130 on the left and a metallization 132 on the right. The MLCC chip capacitor 194 also has overlapping electrodes as illustrated in FIGS. 15A and 15B. An effective capacitance area is thus created by the overlap (interleaving) of the left-hand electrodes 134 with the right-hand electrodes 136.

Figure 16:
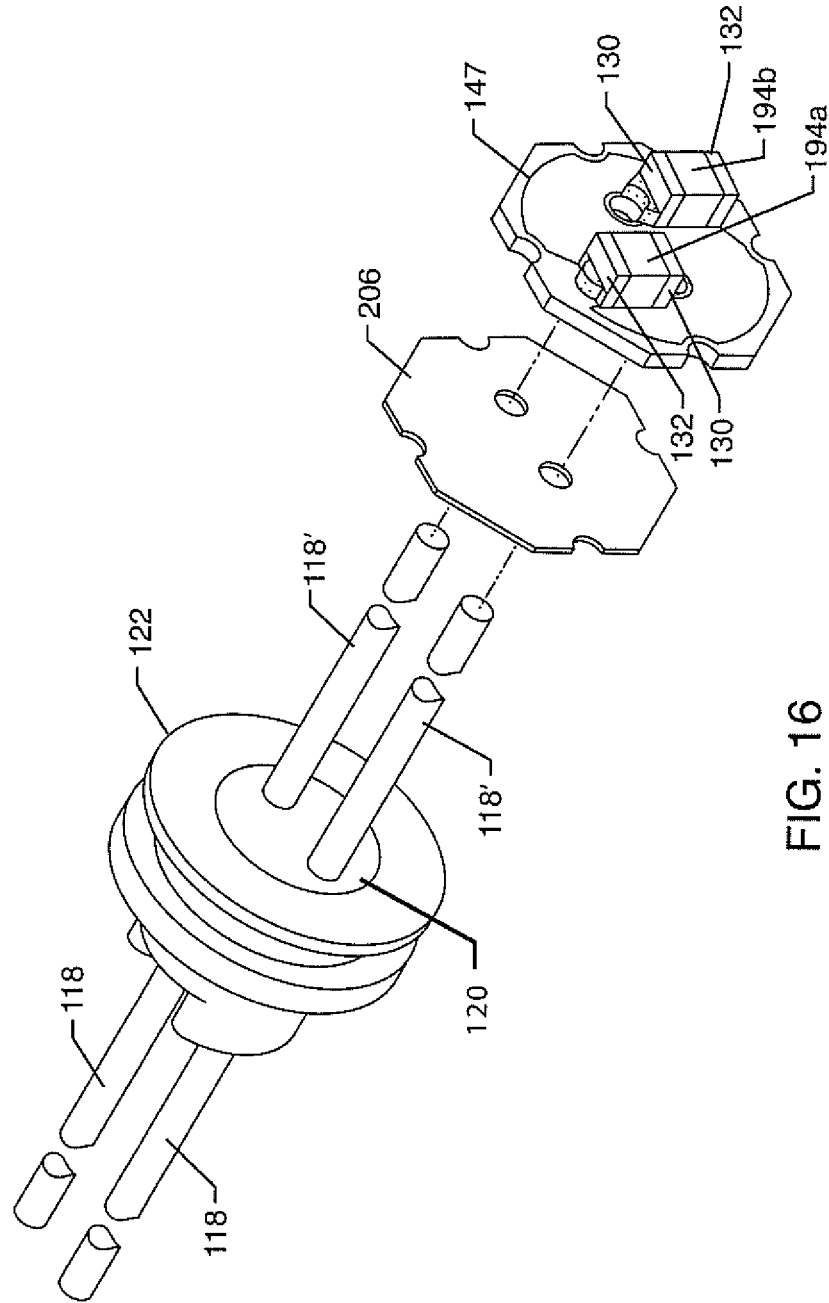
FIG. 16 illustrates a prior art embodiment of MLCC chip capacitors attached to a substrate of an AIMD hermetic seal subassembly.
Figure 17:
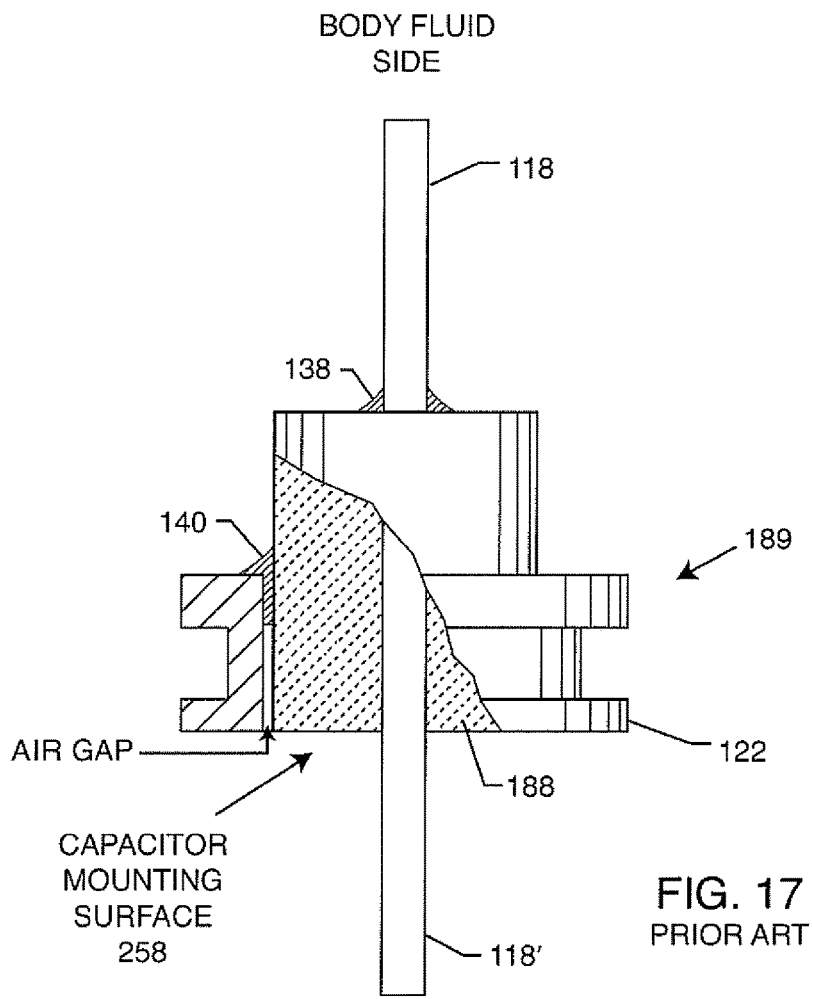
FIG. 17 illustrates a cross-sectional view of a unipolar unfiltered hermetically sealed feedthrough assembly.
Figure 18:
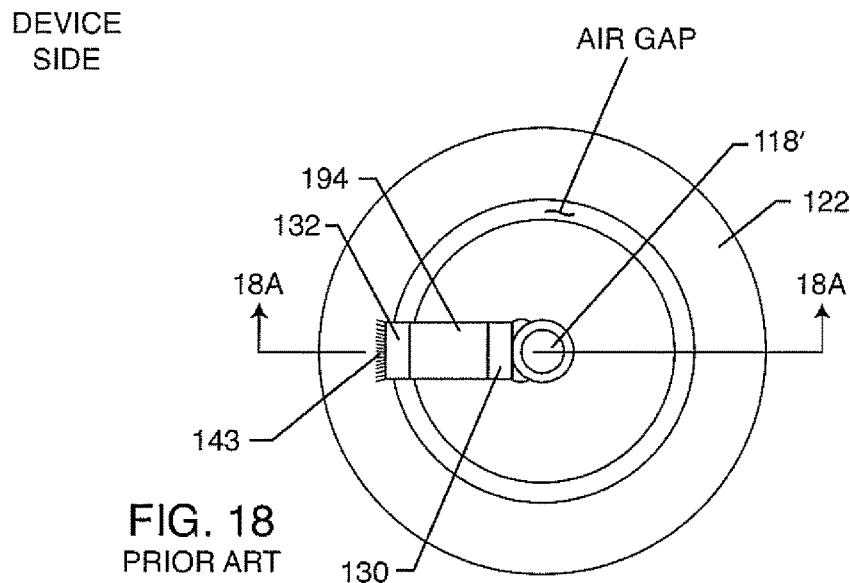
FIG. 18 illustrates a top view of an MLCC chip capacitor attached directly to an oxidized ferrule surface of a hermetically sealed feedthrough.

FIGS. 16, 17 and 18 illustrate prior art applications of MLCC chip capacitors 194 attached to hermetic seal subassemblies of AIMDs. These patents include: U.S. Pat. Nos. 5,650,759; 5,896,267; 5,959,829 and 5,973,906, the contents of which are fully incorporated herein by reference. Referring once again to FIG. 16, the electrical connection between MLCC chip capacitor ground termination 132 and circuit trace 147 is generally oxide-resistant; however, the attachment of the ground circuit trace 147 to the oxidized ferrule 122 in the prior art of FIG. 18 becomes an electrical resistance ($R_{OXIDE}$ 164) problem. Regarding FIG. 18, the left-hand side of the MLCC chip capacitor 194 is shown electrically connected 143 directly to the oxidizable ferrule 122 surface. As previously disclosed for feedthrough capacitors, this is poor practice, as the undesirable resistance ($R_{OXIDE}$ 164) in series with the capacitor filter 194 is unsafe and potentially dangerous to, for example, a pacemaker dependent patient. The undesirable increased resistance due to oxide thickening ($R_{OXIDE}$ 164), also as previously disclosed, can seriously degrade MLCC chip capacitor filter 194 performance and/or dangerously cause filter failure, whereby the MLCC chip capacitor cannot even filter EMI disturbances.

Referring once again to FIG. 17, one can see that there is a hermetic seal insulator 120,188 disposed within a ferrule 122. In FIG. 17, the insulator 120,188 is hermetically sealed by a gold braze 140 between the insulator 120,188 and ferrule 122. There is also a leadwire 118, having a body fluid side lead end 118 and a device side lead end 118'. Leadwire 118 is continuous from the body fluid side to the device side. There is also a hermetic seal gold braze 138, which hermetically seals the leadwire 118 to the insulator 120,188. Throughout this specification, it is understood that the insulator 120,188 is sometimes single-numbered as 120, sometimes single-numbered as 188 or in some cases, is labeled 120,188. It will also be appreciated that the gold braze insulator is typically of a high purity alumina ceramic. It is also appreciated that the insulator can include a glass or a glass-ceramic hermetic seal, in which case the gold brazes 138 and 140 are not necessary (therefore, there are no hermetic seal gold brazes for an oxide-free EMI filter system ground connection).

Figure 18A:
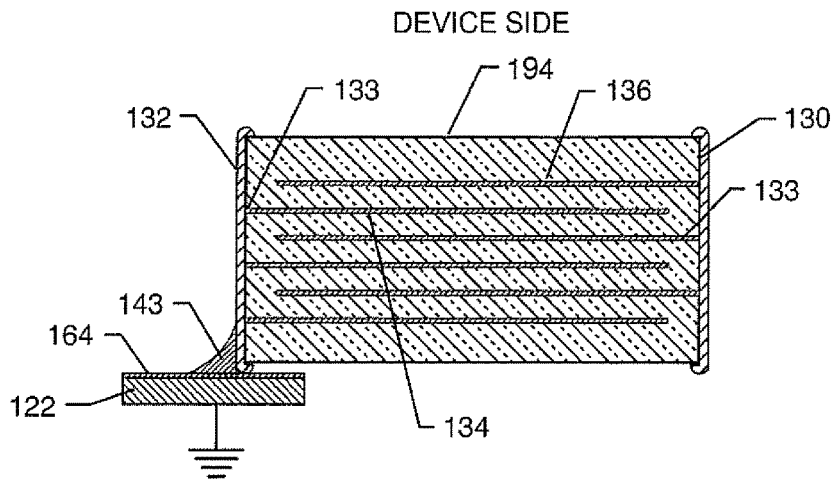
FIG. 18A illustrates a cross-section of the MLCC chip capacitor of FIG. 18, illustrating the elements that give rise to undesirable series resistance.

FIG. 18A is a sectional view taken from section 18A-18A of FIG. 18, which shows the MLCC chip capacitor 194 ground electrode plates 134 and active electrode plates 136. It is appreciated that this symmetrical capacitor can be reversed thereby reversing the ground and active electrode plates. The MLCC chip capacitor has capacitor termination materials 132, as indicated, which are electrically connected using electrical connection material 143 directly to the ferrule 122. Illustrated is the undesirable surface oxide 164 that can form during laser welding of the ferrule 122 and the device housing 102 as previously disclosed. The schematic diagram of FIG. 18A shows undesirable resistance R ($R_{OXIDE}$ 164), which is a result of this undesirable surface oxide 164. As previously described, the dielectric loss is also a series resistance, but at high frequency, the dielectric resistance (loss tangent) will essentially go away.

Figure 18B:
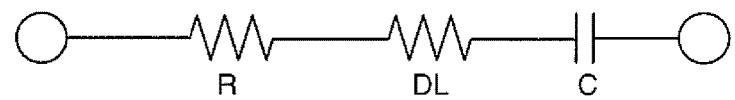
FIG. 18B gives the equations for capacitive reactance and the capacitor's impedance of FIG. 18.

FIG. 18B gives the equations for capacitive reactance and also for impedance. ESR can undesirably increase the filter capacitor's impedance, which is preferably as low as possible.

Figure 18C:
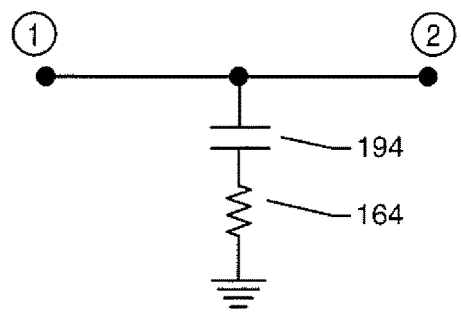
FIG. 18C is the electrical schematic of the filter capacitor of FIG. 18 showing an undesirable series resistance due to titanium oxides.

FIG. 18C further illustrates that the ohmic loss resistance due to surface oxides 164 appears in series with the filter capacitor and system ground 144. This resistance ($R_{OXIDE}$ 164) is highly undesirable and dangerous because it degrades EMI filter performance and/or cause filter failure.

Figure 19:
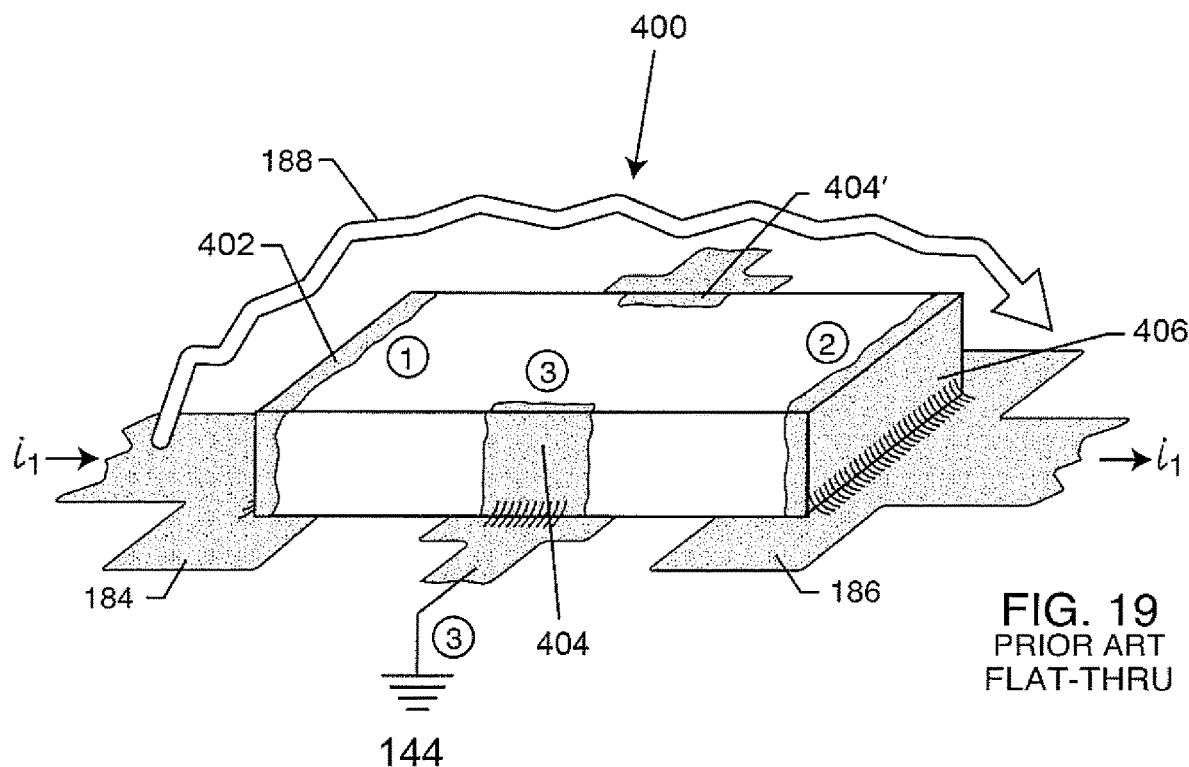
FIG. 19 illustrates a prior art flat-thru capacitor.
Figure 20:
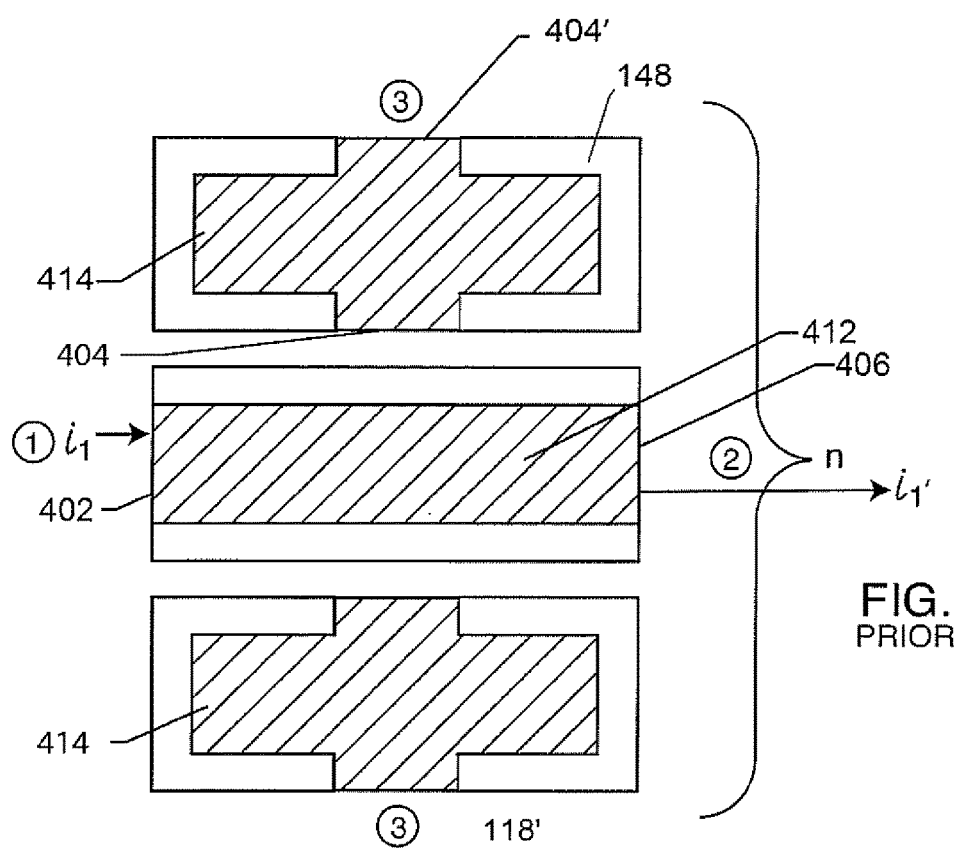
FIG. 20 is a multiple sectional view of the electrode plate stack-up of the flat-thru capacitor of FIG. 19.

FIG. 19 illustrates a prior art flat-thru capacitor 400. This is better understood by referring to its internal electrode plates as illustrated in FIG. 20. The flat-thru capacitor of FIG. 19 is also known as a three-terminal capacitor because there is a circuit current $i_1$ that passes through its active electrode plate 412 from the first terminal 184 to the second terminal 186. If there is a high frequency EMI signal being conducted along this active electrode plate 412, then this EMI is diverted through filter capacitance action to system ground 144 at terminal 3. Referring back to FIG. 19, it is noted that there is a general disadvantage to such capacitors in that, at very high frequency, EMI 188 can cross-couple from the left side of the MLCC chip capacitor to the right side of the MLCC chip capacitor.

Referring once again to FIG. 19, one can see a connection to system ground 144 (ground symbol), which is essential for proper filter performance. As previously described, it is important that this system ground connection be essentially free of undesirable surface oxides ($R_{OXIDE}$ 164).

FIG. 20 illustrates the ground and active electrode plates of the flat-thru capacitor 400 of FIG. 19. The ground electrode plates are 414 and the active electrode plate is 412. These electrode plates are stacked in interleaved relationship forming the flat-thru capacitor. As shown, the circuit current $i_1$ passes through the active electrode plate 412. There is an advantage to this in that any inductance L along the length of the plate appears in series with any EMI thereby improving filter efficiency. A downside of having the current pass through the active electrode plate 412 is the limited current handling capability of the flat-thru capacitor active electrode plates. Flat-thru capacitors, as illustrated in FIGS. 19 and 20, are acceptable for most active implantable medical device applications; however, this configuration is highly unlikely for an implantable defibrillator, wherein a very high current high voltage shock must be delivered. The cross-sectional area of an electrode plate 412 of a monolithic ceramic capacitor is generally limited in cross-sectional area.

Figure 21:
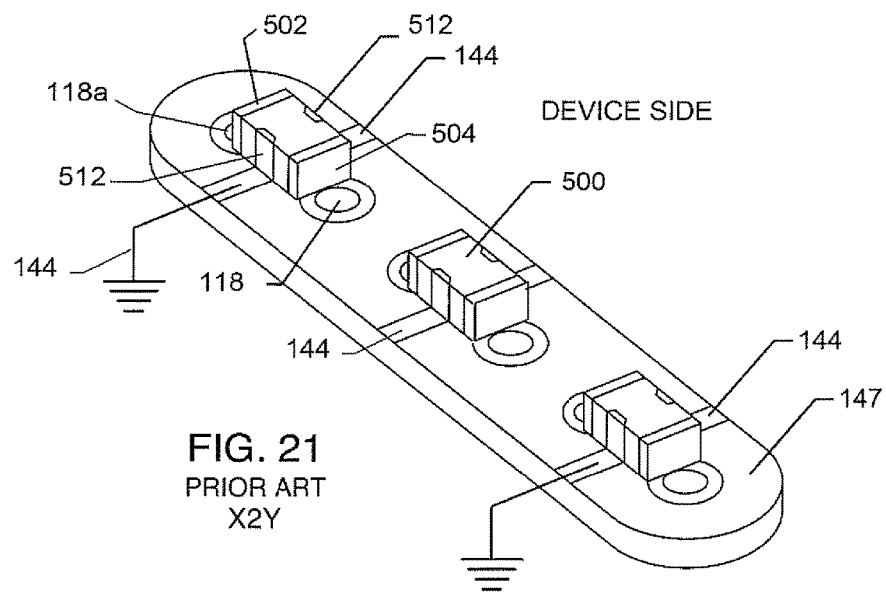
FIG. 21 illustrates a filter assembly comprising three-terminal capacitors, which are also known in the industry as X2Y attenuators.

FIG. 21 illustrates three X2Y attenuators 500 mounted on an EMI filter circuit board 147 that is designed to be placed adjacent to the device side of an insulator 120 and/or a ferrule 122 of an AIMD hermetic seal subassembly. These X2Y attenuators 500 are bipolar, meaning that each pair of X2Y attenuators filters two active leadwires 118,118', as shown. The X2Y attenuators 500 have two active terminations 502 and 504 as shown. The X2Y attenuators 500 also have ground terminations 512 that must be electrically connected to system ground 144.

Figure 22:
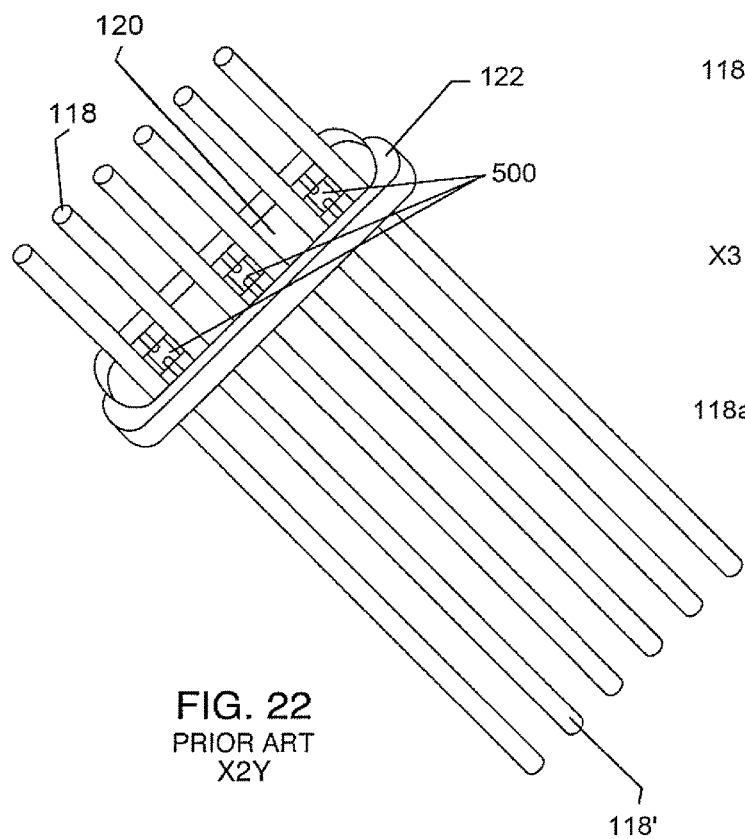
FIG. 22 illustrates a hermetically sealed filter feedthrough assembly comprising the filter assembly of FIG. 21.

FIG. 22 illustrates the three X2Y attenuators 500 of FIG. 21 mounted on the device side of insulator 120 and in a pocket of the ferrule 122.

Figure 22A:
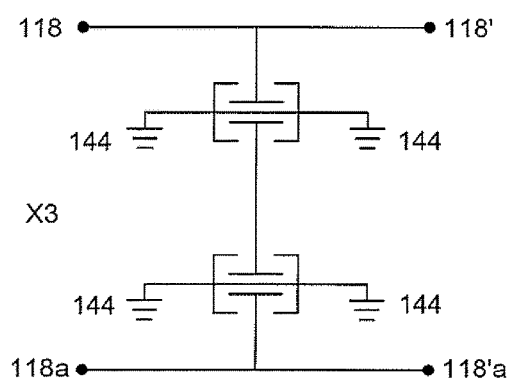
FIG. 22A illustrates THE electrical schematic of the filter assembly of FIGS. 21 and 22.

FIG. 22A is a schematic diagram that illustrates each one of the X2Y attenuators. The X3 next to the schematic indicates that there are three of these bipolar X2Y attenuators. Referring once again to FIG. 22A, one can see that this X2Y attenuator 500 is disposed between adjacent active leadwires 118,118',118a,118'a. One can see that there is line-to-ground capacitance between adjacent active leadwires 118,188a and also from each active leadwire to system ground 144. The X2Y attenuator 500 forms line-to-line capacitance through the series capacitances between adjacent active leadwires 118,118',118a,118'a. From an EMI perspective, the line-to-ground capacitance is useful for diverting differential-mode EMI, and the line-to-line capacitance is useful for attenuating differential-mode EMI. An example of differential-mode EMI is an EMI signal that produces a voltage when measured adjacent leadwire to leadwire. This differential voltage is best measured without the X2Y filter 500 present. By careful design of the X2Y attenuator internal electrode plates, one can control the amount of capacitance to ground and also the amount of line-to-line capacitance. The electrical schematic of FIG. 22A assumes that the electrical ground connections are to a unoxidized ferrule 122 surface, such as the gold braze 138 that is formed between the ferrule 122 and the hermetic seal insulator 120. This is why there is no resistance ($R_{OXIDE}$ 164) shown in the system ground 144 connections of FIG. 22A.

Figure 23:
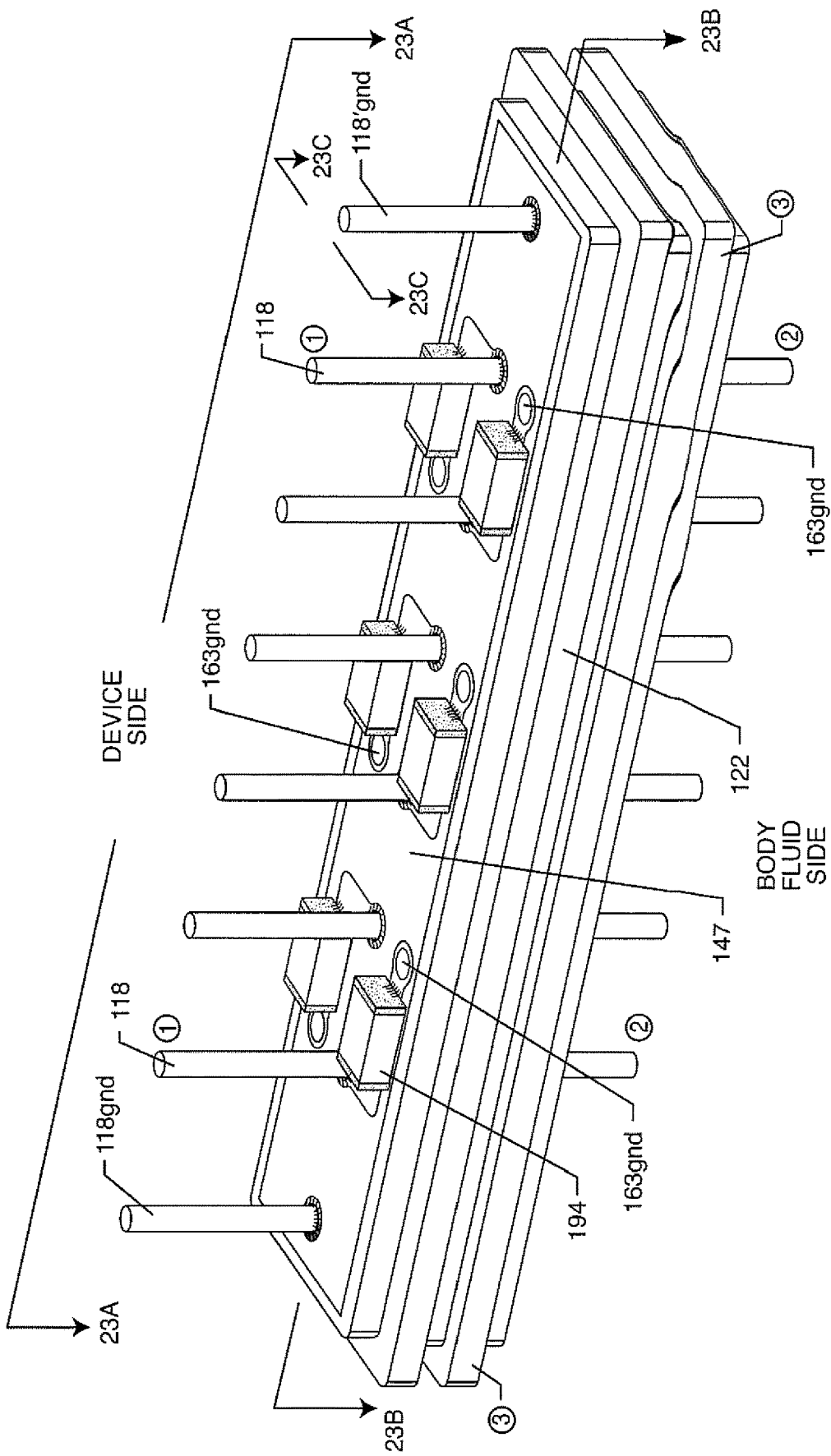
FIG. 23 is a perspective view of a prior art MLCC filter circuit board electrically connected to an AIMD feedthrough ferrule.

FIG. 23 illustrates a prior art filtered feedthrough assembly. In this case, there is an MLCC filter circuit board 147. Disposed on the circuit board are six MLCC chip capacitors 194. Accordingly, the MLCC filter circuit board is disposed on an AIMD hermetically sealed feedthrough that has six active poles or leadwires. The ground leadwires on the left end and the right end are labeled 118gnd. These ground terminal pins are electrically and mechanically connected to the ferrule 122, each terminal pin providing a ground connection to internal MLCC filter circuit board ground plates (not shown). As will be disclosed, these circuit board ground plates are extremely important so that EMI is reflected similarly to prior art feedthrough filter capacitors.

FIG. 23A is taken from section 23A-23A of FIG. 23 showing a top view of the of the MLCC filter circuit board of FIG. 23. Also shown are the MLCC chip capacitors 194a through 194f.

FIG. 23B is taken from section 23B-23B of FIG. 23 illustrating at least one internal circuit board ground plate 161 embedded within the MLCC filter circuit board. The at least one internal circuit board ground plate 161 is electrically connected to system ground 144 through the two ground pins 118'gnd that are electrically connected to the ferrule 122. The at least one internal circuit board ground plate 161 comprises ground via holes 163a through 163e that provide an electrical ground connection to each of the six MLCC chip capacitors 194. Referring once again to FIG. 23A, one can see that there are circuit board via holes 163 electrically connected to the ground metallization 130 of each of the MLCC chip capacitors 194. An optional circuit trace is shown between the ground via holes 163 and the MLCC chip capacitor ground termination 130. It is appreciated that the ground connection to the MLCC chip capacitor ground termination 130 can be a direct electrical connection to the circuit board via hole or through a circuit board circuit trace, which may be configured in various ways including the embodiment as shown. For optimal filter performance, the circuit trace length is as short as possible to minimize series inductance. Referring once again to FIG. 23B, one can see that the hermetic seal active leadwires 118' passes through the circuit board ground plate 161 in non-conductive relation. The embedded or exterior circuit board ground plate 161 can consist of a multiplicity of ground plates and including a ground plate preferentially disposed between the circuit board and the insulator 120 of the hermetically sealed feedthrough. This relatively wide set of one or more circuit board ground plates 161 provides a very low inductance path to divert EMI from the active leads 118 to the system ground 144. In addition, the one or more circuit board ground plates 161 effectively reflect or absorb radiated electromagnetic fields thereby preventing direct entry of EMI into the interior (device side) of the AIMD housing. This reflection and absorption of incident fields is very important at high frequencies, for example, MRI frequencies and the frequency range of cellular telephones and other wireless communicators, from approximately 300 MHz to 3000 MHz.

Figure 23C:
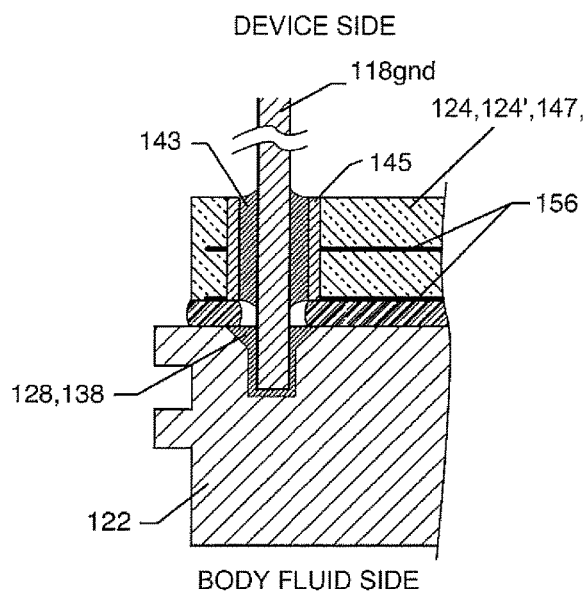
FIG. 23C is taken from section 23C-23C of FIG. 23 illustrating an oxide-resistant circuit board ground pin.

FIG. 23C is a cross-sectional view taken from 23C-23C of FIG. 23 illustrating an embodiment of the ferrule ground pin 118gnd. The ground pin 118gnd is shown electrically and mechanically connected to the ferrule 122 by either a laser weld 128 or a gold braze 138. Ideally, ground pin 118gnd is of an oxide-resistant material, such as, but not limited to, platinum, palladium, gold, rhodium, and their alloys. This makes for an essentially oxide-free electrical connection 143 to the circuit board internal ground plates 156. In this case, there are two circuit board ground plates: an internal circuit board ground plate, which is embedded in the circuit board, and an external circuit board ground plate, which is disposed on the bottom of the circuit board. It is understood that, while two circuit board ground plates are illustrated in FIG. 23C, the circuit board may have one circuit board ground plate, which can be disposed either internal or external of the circuit board. It is also anticipated that there may be a multiplicity of embedded internal ground plates either in combination with at least one external circuit board ground plate or without any external circuit board ground plates. Additionally, any circuit ground plate may alternatively be a circuit trace. Referring once again to FIC. 23C, one will see that there is a circuit board via hole, which has a via hole metallization 145 that is spatially aligned over the ground pin 118gnd. Throughout the present application, via holes are provided with some sort of an electrically conductive or metallization layer on the inside diameter. It is understood by one skilled in the art that the inside diameter of circuit board via holes can be metal eyelets, plated, metallized, or the like. In each case, the electrically conductive layer or the metallization of the via hole is electrically connected to one or more internal or external circuit board ground plates or circuit traces. In the case of FIG. 23C, the circuit board metallization 145 makes electrical contact to the one internal and the one external circuit board ground plates 156 as illustrated. Orientation and filter system electrical ground connection to a ferrule ground pin is taught by U.S. Pat. No. 8,195,295, the contents of which are incorporated herein fully by reference. U.S. Pat. No. 8,195,295 also applies to the structure shown in FIG. 23D.

Figure 23D:
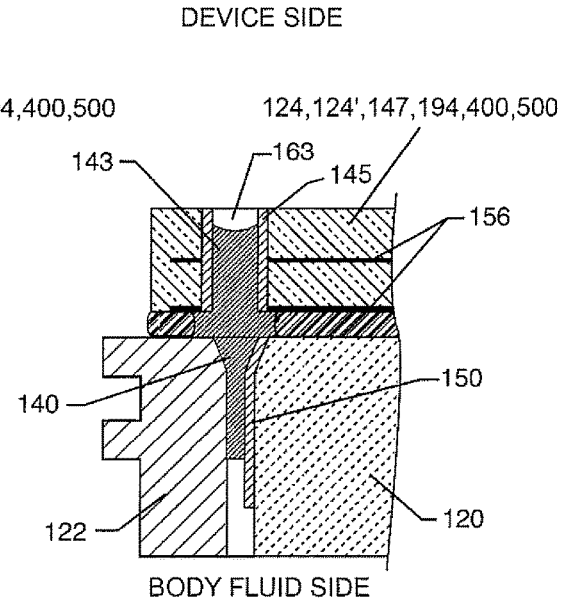
FIG. 23D illustrates that the ground pin of FIG. 23C can be replaced by a spatially aligned ground via over the gold braze hermetically sealing the feedthrough insulator and the ferrule.

FIG. 23D illustrates an alternative embodiment of electrically grounding circuit board ground plates 156. In this case, a circuit board ground via hole 163 is spatially aligned over the gold braze 140 that forms a hermetic seal between the insulator 120 and the ferrule 122 of the hermetically sealed feedthrough. By spatially aligning the ground via hole over the gold braze 140, one can then make an essentially oxide-free electrical connection directly to the hermetic seal gold braze using electrical connection material 143 as shown. Electrical connection material 143 can be a solder, a thermal-setting conductive adhesive, an electrically conductive adhesive, an electrically conductive polymer, an electrically conductive epoxy, an electrically conductive elastomer, an electrically conductive polyimide or the like. Referring once again to FIG. 23D, illustrated is a metallization layer 150 disposed on the perimeter wall of the insulator 120. The metallization layer 150 is, generally, an adhesion/wetting layer that, during the brazing process, facilitates the flow of the gold braze 140. An electrical connection to the gold braze hermetically sealing the insulator 120 and the ferrule 122 provides a reliable low resistance low impedance and stable electrical ground connection. Electrical connection to the hermetic seal gold braze 140 additionally provides a very low and reliable stable resistance for the circuit board system electrical ground path.

Figure 23E:
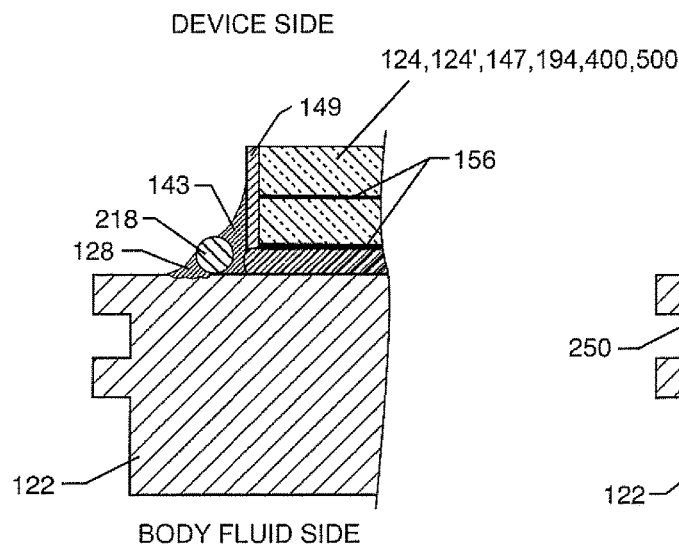
FIG. 23E illustrates that the circuit board of FIG. 23 may have an edge metallization attached to a metal addition laser welded or gold brazed to the AIMD feedthrough ferrule.

FIG. 23E shows that an oxide-free electrical ground connection to the circuit board ground plates 156 can also be achieved by an oxide-resistant metal addition 218, which is either gold brazed or welded 128 to the ferrule 122. It is preferred that this metal addition is of an oxide-resistant material, such as, but not limited to, platinum, palladium, gold, rhodium, and their alloys. The metal addition 218 illustrated in FIG. 23E, is taught by U.S. Pat. No. 9,931,514, the contents of which are incorporated herein fully by this reference.

Figure 23F:
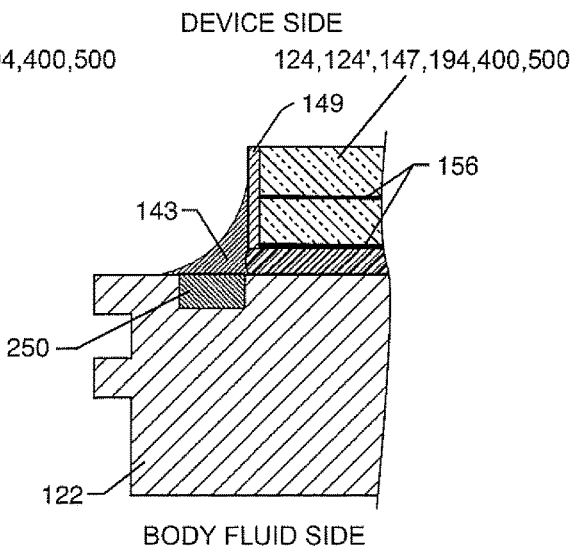
FIG. 23F illustrates that the circuit board of FIG. 23 can have a ground edge metallization that is electrically connected to a gold pocket-pad formed in a recess of the AIMD feedthrough ferrule.

FIG. 23F illustrates another method of forming an oxide-resistant electrical ground connection 143 from the circuit board ground plates 156 to the ferrule 122. In this case, there is a gold pocket-pad 250, which acts like a swimming pool moat into which the gold braze, or equivalent materials are disposed. As a result, an oxide-resistant electrical ground connection is formed to the ferrule 122 and the circuit board ground edge metallization 149 and, in turn, to the circuit board ground plates 156. Referring once again to FIG. 23F, gold pocket pads 250 are taught by U.S. Pat. No. 10,350,421, the contents of which are incorporated herein fully by this reference. The '421 patent pocket-pad invention does not teach barrier layers. This is because the gold or equivalent layers in the pocket are sufficiently thick (greater than 1 μm), that diffusion of titanium to the surface and re-oxidation does not happen. However, proud (disposed atop a metallic surface) oxide-resistant coatings 165 can generally be very thin (less than 1 μm, even Angstroms thick), such that diffusion becomes important to manage. One solution regarding thin oxide-resistant coatings is to dispose a very thick oxide-resistant coating 165 proud of the ferrule surface. It is also important to manage the thickness of a very thick oxide-resistant layer disposed on a metallic surface, as very thick oxide-resistant layers can be expensive and often tend to be messy. For example, if a thick gold preform were affixed proud of a ferrule surface and then reflowed at high temperature in a brazing furnace, the gold can uncontrollably run and flow all over the surface forming thin layers instead of a confine thick layer as intended.

FIG. 23G is similar to FIG. 23C in that there is an oxide-resistant ground pin 118gnd, which is electrically and mechanically connected to the feedthrough ferrule 122 by a laser weld 128 or a gold braze 138. In this case, instead of electrically grounding through a via hole, as illustrated in FIG. 23C, there is an electrical connection 143 from a circuit board ground edge metallization 149 directly to the oxide-resistant ground pin 118gnd. Accordingly, this provides a very low resistance (low ESR) grounding path to system ground 144. As previously defined, system ground 144 is the AIMD housing 102 and is also equivalent to the system ground 144 provided by the ferrule 122. Importantly, circuit board ground plates 156 provide a low impedance path for the filters (an MLCC chip capacitor 154, an X2Y attenuator 300, a flat-thru capacitor 400, and combinations thereof) to divert dangerous EMI currents while at the same time, shielding the insulator 120 from direct penetration of high frequency RF-radiated noise (EMI). Referring again to FIGS. 23C-23H, the circuit board ground plates 156 can also be called circuit board ground shield plates. In other words, the ground plates 156 not only provide a low impedance filter circuit diversion pathway to system ground, but also shield against radiated EMI. Referring once again to FIG. 23C, one can see that the radiated EMI is reflected off filter ground electrodes. Circuit board shield plates or ground plates act in identical manner. These ground plates 156 also absorb incident RF energy and the capacitive action of the filter diverts the RF energy to the AIMD housing 102 (not shown), where, as previously disclosed, the RF energy is harmlessly dissipated as a few milliwatts of heat energy. This diversion prevents the EMI from dangerously reaching the inside of the AIMD shielded housing 102 of the embodiment of FIG. 23A. Referring once again to FIG. 23G, grounding a circuit board edge metallization to a ground pin is taught by U.S. Pat. No. 8,195,295, the contents of which are incorporated herein fully by reference.

FIG. 23H is very similar to FIG. 23F in that an oxide-resistant gold bond pocket-pad 250 has been provided in a ferrule recessed pocket. In this case, a circuit board ground via hole 163 is spatially aligned over the gold pocket-pad 250, such that an electrical connection 143 is made to the oxide-resistant gold fill in the pocket. In this way, circuit board ground plates 156 comprise a very low resistance electrical connection to system ground 144, which is also the ferrule 122 ground. Gold pocket-pads are disclosed in U.S. Pat. No. 10,350,421, the content of which is incorporated fully herein by this reference. Gold pocket-pads may comprise other oxide-resistant materials such as platinum, palladium, gold, rhodium, and their alloys. Oxide-resistant metals, such as gold and platinum, are used as jewelry for this reason, as gold and platinum do not tarnish or oxidize over time. An oxide-resistant pocket-pad 250 may comprise an oxide-resistant material selected from the group consisting of gold, gold alloys, rhodium, rhodium alloys, platinum, platinum alloys, platinum-iridium alloys, palladium, palladium alloys, nitinol, titanium nitride, cobalt-chromium alloys and combinations thereof. This group of oxide-resistant materials may be used in any of the oxide-resistant electrical connection embodiments disclosed herein. As noted earlier, some oxide-resistant pocket-pad materials may be costly, as the swimming pool-like pocket-pad formed in the recessed pocket of the ferrule 122 may require a substantially large quantity of oxide-resistant material to be disposed and subsequently re-flowed and contained within the pocket-pad 250. Referring once again to FIG. 23H, spatially aligning a circuit board via hole over a gold pocket-pad 250 is taught by U.S. Pat. No. 10,350,421, the contents of which are incorporated herein fully by reference.

FIG. 23I illustrates the schematic diagram of the embodiment of FIG. 23 showing that both the inductance L and the resistance R are minimized (essentially zero) such that an ideal capacitor having very low series resistance ESR or R is formed, which results because $R_{OXIDE}$ has been eliminated. As illustrated by the embodiments of FIGS. 23A through 23H, since an oxide-resistant or an essentially oxide-free electrical connection can be formed in accordance with the teachings of the present application, therefore, there is no need for a resistor symbol $R_{OXIDE}$, 164 in the schematic of FIG. 23I. It is appreciated that for insertion loss simulations, for example, using PSpice, one includes a resistance in series with the ideal capacitor, the resistance being the high frequency ESR. In order to do this simulation, one must first use a high frequency materials analyzer to very accurately measure the filter capacitor's ESR at each frequency of interest, and then use that value of resistance in the PSpice models to accurately predict the insertion loss at each frequency. It is emphasized that the present application teaches oxide-resistant coatings, layers and structure that essentially eliminate the resistance due to $R_{OXIDE}$, 164. Hence, to fully understand the impact of high-frequency ESR due to ohmic loss of a feedthrough filter capacitor using other than the teachings provided herein, the high-frequency ESR value must still be considered in the PSpice model to obtain accurate insertion loss predictions.

Figure 24:
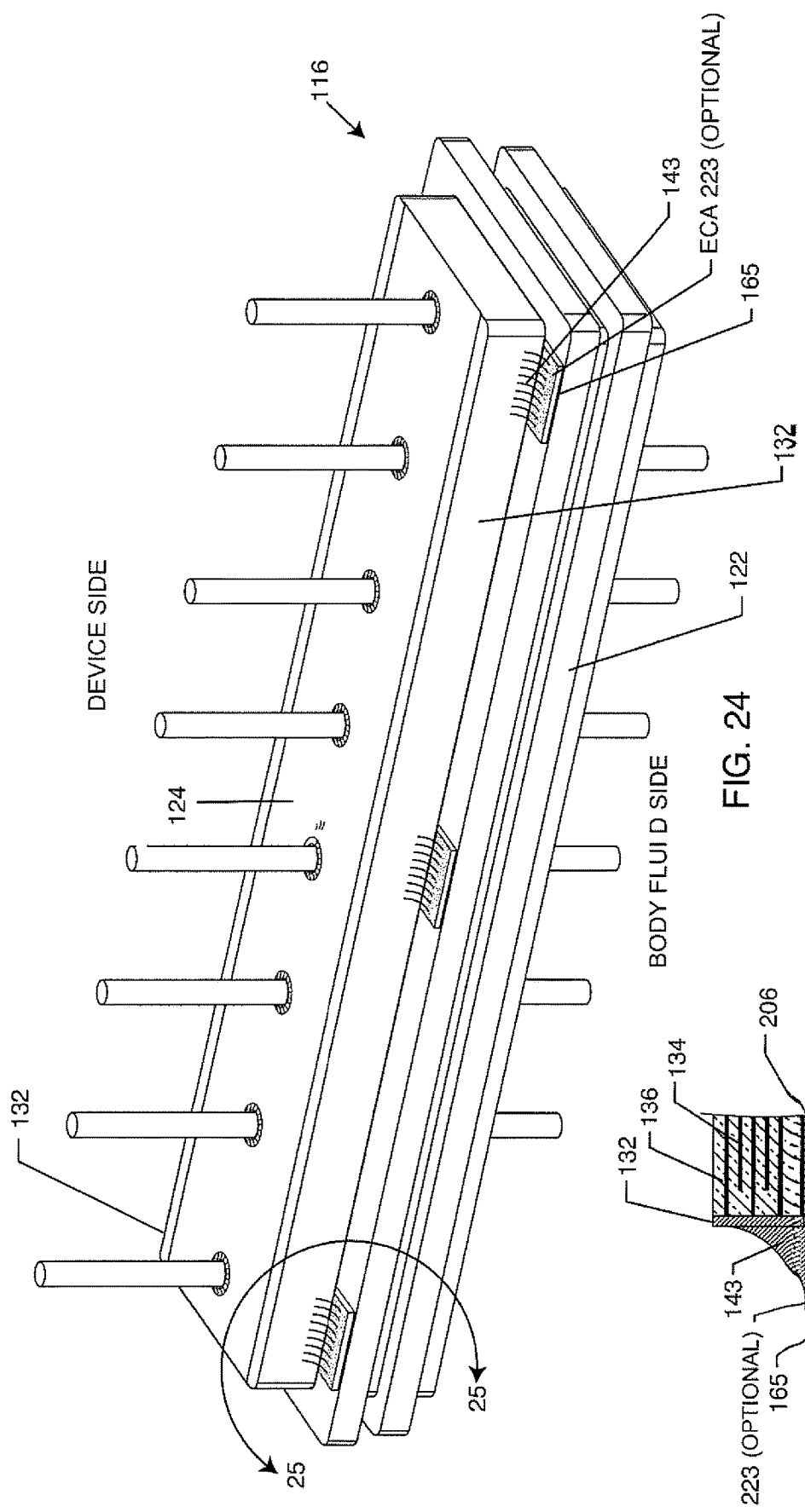
FIG. 24 illustrates an inline octapolar feedthrough capacitor of the present invention electrically connected in an oxide-resistant manner to on an oxide-resistant coating or layer on the feedthrough ferrule surface.

FIG. 24 illustrates a prior art circuit board 147 having circuit board edge ground metallizations 149 electrically connected to the circuit board ground plates (not shown), and which are directly electrically connected 143 to the oxidizable ferrule surface 122. Such direct electrical ground connection to the ferrule 122, as illustrated, is extremely poor practice. As previously described, the surface of a titanium ferrule 122 is prone to the formation of resistive or semi-conductive oxidation layers 164, which can significantly, even dangerously, reduce EMI filter performance. All of the same concepts as previously taught herein for feed-through filter capacitors 124, apply to filter circuit boards 147, including the filter circuit board of FIG. 24. As previously described, oxide removal of the titanium ferrule 122 by chemical, mechanical or plasma processes is only temporary, as oxides will almost immediately reform. These oxides form even more quickly at elevated temperatures, such as the high temperatures created by laser welding 128 the ferrule 122 into an opening of an AIMD housing 102 (not shown).

Figure 25:
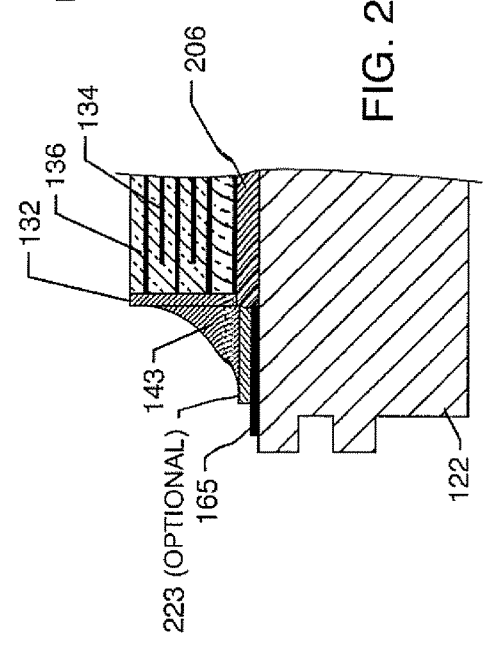
FIG. 25 is taken from section 25-25 of FIG. 24 illustrating the oxide-free electrical connection to the feedthrough ferrule.

Referring to FIGS. 24 and 25, the inventors provide a novel concept by which an optional ECA stripe 223 can be effective. To render the optional ECA stripe 223 effective, a low resistance low impedance temperature stable electrical connection to the ferrule 122 must be made. To achieve such a low resistance low impedance temperature stable electrical connection, especially at high frequencies, two very important steps are required: Step 1) at least the attachment area of ferrule 122 device side surface must be cleaned of all oxides; and Step 2) an oxide-resistant coating 165, as shown in FIGS. 25A and 26A, must be disposed on the cleaned ferrule 122 device side surface where the optional ECA stripe 223 is to be disposed. As used herein, the ferrule 122 is only exemplary, hence, the two very important steps disclosed above equally apply to any oxidizable metallic surface of the embodiments of the present invention. As described previously, cleaning a ferrule 122 device side surface can be done mechanically, chemically or by plasma methods, by either abrasive grit blasting, such as by alumina blasting, mechanical grinding, sanding processes, hydrofluoric acid cleaning, plasma etching or combinations thereof, which would remove oxide layers from the surface of the ferrule 122, or at least a portion of the ferrule device side surface. Once the exemplar ferrule 122, and in particular, the exemplar ferrule device side surface is essentially cleaned of oxides, time and temperature become important. If the cleaned exemplar ferrule is left lying around at room temperature, or worse yet, exposed to elevated temperatures, intentionally or unintentionally, the oxide layer 164 will undesirably re-form. Accordingly, the inventors have tested and determined that an oxide-resistant coating 165, such as an oxide-resistant metal layer comprising one or more of the oxide-resistant materials previously disclosed, must be placed proud of the oxidizable component surface, such as the exemplar ferrule 122, soon after the oxidizable component surface, in this case, at least the ferrule 122 device side surface, is cleaned of its surface oxides. Otherwise, once the oxidizable component, in this case the exemplar ferrule, is cleaned of its surface oxides, the cleaned ferrule (or cleaned oxidizable component) must be stored in an inert atmosphere, such as argon, nitrogen or helium; then, once removed from storage, the oxide-resistant coating 165 must be quickly applied on the ferrule's 122 clean surface. In one particularly preferred method, in a single or multiple chamber apparatus, the oxidized surface may be cleaned by, for example, plasma etching and then, while still contained within a high vacuum environment, the ferrule or AIMD housing or other oxidized component is moved automatically, mechanically, robotically, or by belt into a sputter deposition area of the apparatus, whereby the oxide-resistant coating of the present invention is applied. Alternatively, the ferrule (or any cleaned oxidizable component) instead may remain stationary, and the cleaning and oxide-resistant application units of the apparatus may be automatically, mechanically or robotically moved to the location of the ferrule (or other component) for application of the oxide-resistant material. In this way, any chance that the oxidizable surface could re-oxidize between the cleaning and oxide-resistant coating steps is essentially avoided. The oxide-resistant material applied, as previously disclosed, may comprise an oxide-resistant material selected from the group consisting of gold, gold alloys, rhodium, rhodium alloys, platinum, platinum alloys, platinum-iridium alloys, palladium, palladium alloys, nitinol, titanium nitride, cobalt-chromium alloys and combinations thereof. Some exemplary platinum-based oxide-resistant alloys for use in the oxide-resistant coating 165 of the present invention include: platinum-rhodium, platinum-iridium, platinum-palladium, or platinum-gold. Naturally occurring oxide-resistant alloys examples include: platinum iridium (platinum-iridium), iridosmium and osmiridium (iridium-osmium). Other oxide-resistant alloys include: gold-based, platinum-based, palladium-based, rhodium-based, silver-based, among others, wherein the metal-based element is the largest weight percent (>50%) of the total alloying elements of the alloy. Non-limiting oxide-resistant metal-based oxide-resistant alloys for use in the oxide-resistant coating 165 of the present application include: gold-palladium, gold-boron, and palladium-silver. It is anticipated that proprietary oxide-resistant alloys such as but not limited to the Pallabraze product family (palladium-containing) and Orobraze product family (gold-containing) offered by Johnson Matthey may additionally be used to form oxide-resistant coatings of the present invention. The oxide-resistant material may be applied by sputtering, physical vapor deposition, chemical vapor deposition, electrostatic spray assisted vapor deposition (ESAVD), electron beam physical vapor deposition (EBPVD), ion plating, ion beam assisted deposition (IBAD), magnetron sputtering, pulsed laser deposition, sputter deposition, vacuum deposition, pulsed electron deposition (PED), plating, electroless plating, electroplating, spraying, painting, plasma spraying, thermal spraying, spin coating, dip coating, metal foil lamination, and thin film deposited layers, either fully or selectively disposed. It is important to note that the term electrically conductive adhesive stripe or ECA stripe 223 is not meant to be eliminated from use, when its use facilitates electrical connection; however, when the ECA stripe is optionally used, the optional ECA stripe 223 is never to be applied directly onto an oxidizable electrically conductive surface as shown by FIGS. 24 and 25. It is also noted that the optional ECA stripe 223 may instead comprise stripes of other electrically conductive materials such as a solder, a thermal-setting electrically conductive adhesive, electrically conductive polyimides, electrically conductive polymers, electrically conductive elastomers and electrically conductive epoxies. As previously described, the exemplar ferrule 122 device side surface must be cleaned of all surface oxides immediately prior to deposition of the oxide-resistant coating 165. Preferably, the deposition processes disclosed herein to apply the oxide-resistant coating 165 are performed in a vacuum chamber or in a dry inert atmosphere, either with or without a desiccant and/or an oxygen getter strategically positioned to improve the vacuum or the "dryness" of the inert atmosphere. The desiccant and/or oxygen getter may further be strategically positioned by one of: a layer or area on a portion of the oxidizable surface of the electrical component; somewhere on a surface of a processing chamber; on the surface at the entry ports or transport mechanisms of processing equipment; on, adjacent or otherwise near a manufacturing fixture; and combinations thereof. The oxygen getter material may be selected from the group consisting of aluminum, magnesium, barium, thorium; zirconium, uranium, alloys of rare-earth elements, and titanium. It is noted that gas absorbing by titanium depends on its temperature. Above 700° C., titanium will getter oxygen, nitrogen, and carbon dioxide, while hydrogen is absorbed in the temperature range of 25-400° C. The desiccant material may be selected from the group consisting of silica gel, activated charcoal, calcium sulfate, calcium chloride, and molecular sieves (typically, zeolites). Desiccants may also be categorized by their type, either I, II, III, IV, or V. These types are a function of the shape of the desiccant's moisture sorption isotherm. The performance of any desiccant varies with temperature and both relative humidity and absolute humidity. The desiccant choice, that is, which desiccant best suits a specific processing need, is dependent on the specific parameters of the specific process used to apply the oxide-resistant coating.

Figure 31:
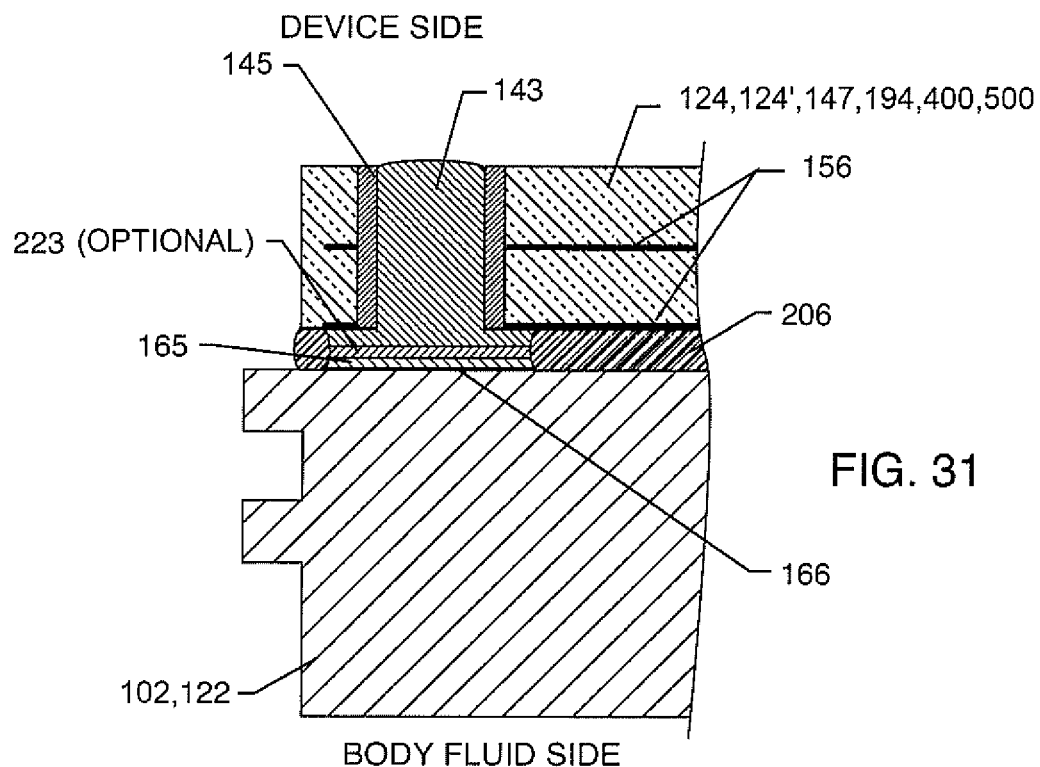
FIG. 31 illustrates an electrical ground connection of a filter circuit board through the circuit board ground via hole to an optional ECA stripe overlaying atop an oxide-resistant coating of the present invention.

In addition to applying the oxide-resistant coating to a cleaned oxidizable component surface, the above cleaning and coating methods, including the optional inclusion of getters and desiccants apply to optional barrier layers 166 disposed between an oxidizable surface, such as the exemplar ferrule 122, and an oxide-resistant coating 165 (see barrier layer 166 of FIG. 31). Regarding barrier layers, the barrier layer 166 is first disposed atop the cleaned ferrule device side surface 122, and then the oxide-resistant coating 165 is disposed atop the barrier layer. One or more barrier layers 166 may be disposed between the cleaned oxidizable surface and the oxide-resistant layer 165 using the same processes of the oxide-resistant layer disclosed above. As an example, an optional layer of nickel is first disposed on top of the cleaned essentially oxide-free surface, followed by an oxide-resistant coating 165, such as, but not limited to, platinum, palladium, gold, rhodium, and their alloys, including any of the materials disclosed above, disposed on top of the optional nickel layer. The purpose of the nickel layer is to prevent titanium from migrating through the oxide-resistant layer. In the case of a thin film gold layer, for example, which is highly resistant to forming oxides and is highly conductive, the thin film gold layer may be relatively "porous", allowing titanium to migrate through the thin film gold layer to its free (top) surface. Accordingly, when a thin film gold layer is disposed on an essentially oxide-free titanium surface, the titanium can diffuse along the grain boundaries at the gold/titanium interface to the free surface of the thin film gold layer, where the titanium is oxidized. Thus, by disposing a barrier layer of nickel or other suitable material, migration of titanium through the thin film gold layer is prevented. In an embodiment, a nickel layer is not required when a suitably thick layer of gold having a thickness greater than 1 μm is disposed.

Referring again to FIG. 24, illustrated is a conventional externally grounded feedthrough capacitor 124 similar to the feedthrough EMI filter capacitor 124 of FIG. 3 and FIG. 7 previously disclosed. In this embodiment, however, the feedthrough EMI filter capacitor is an inline 8-polar (octapolar) filter capacitor and not a discoidal filter capacitor. Electrical ground connections 143 are made to an optional ECA stripe 223 which overlays an oxide-resistant coating 165 of the present invention. The optional ECA stripe 223, which overlays the oxide-resistant coating 165, and the oxide-resistant coating itself, can be discrete pads or be continuous along both long sides of the feedthrough capacitor or all around the full perimeter of the feedthrough ferrule surface. The inventors found through analysis and testing that the oxide-resistant coatings 165 and optional overlaying ECA stripes 223 can be discontinuous, as illustrated, and still provide excellent high frequency EMI filter performance.

In summary, it is important to emphasize again that oxide-resistant coatings 165 enable very low resistance and time-stable electrical connections, which, in turn, provide very low equivalent series resistance (ESR) electrical connections, and that oxide-resistant time-stable electrical connections are very important for medical devices, particularly AIMDs, as the inventors have discovered that, without oxide-resistant time-stable electrical connections, highly reactive materials to the presence of oxygen, such as titanium, can continue oxidation over time resulting in an undesirable oxide thickening, which, thereby, can cause latent dangerous and unpredictable AIMD EMI filter performance issues. It is also important to emphasize that titanium oxides are also voltage sensitive exhibiting bizarre semi-conductive behavior, wherein the resistance of the oxide can appear to disappear and then quickly come back over a period of days. Most importantly, EMI filter failure resultant from oxide 164 thickening over time can be life-threatening to an AIMD patient. It is also important to note that numerous articles report EMI disrupting the proper operation of an AIMD. Thus, it is important to emphasize that, if an EMI filter fails to filter in a cardiac pacemaker, the EMI can then enter the housing of the pacemaker within which the therapy delivery circuitry resides. It is specifically the EMI inside the pacemaker that leads to improper therapy and even complete inhibition of therapy to the patient. As a reminder, inhibition of therapy from a cardiac pacemaker to a pacemaker dependent patient can be immediately life-threatening to that patient. While a titanium oxide layer on the highly reactive titanium metal surface imparts good corrosion behavior and high biocompatibility, which, as previously disclosed, is why titanium is used so extensively in medical implantable devices, the titanium oxide layer 164 that forms so readily on the titanium metal can and does negatively impact AIMD EMI filter performance, the negative impact being particularly observable at higher frequency applications, such as switching applications, coupling applications, bypass applications in addition to EMI filtering.

As such, the term "oxide-resistant" is defined herein as the ability of a substance to maintain its original material properties after being exposed to oxygen; a resistance to oxidation under extreme conditions such as high temperature, essentially resists reaction with oxygen or oxygen-containing environments.

FIG. 25 is taken from section 25-25 from FIG. 24 and illustrates in cross-section, the optional ECA stripe 223 that overlays the relatively thin oxide-resistant coating 165. As illustrated, once the thin sputter layer has been deposited 165, then an optional ECA stripe 223 is applied. The optional ECA stripe, as defined herein, may comprise one of: a thermal-setting electrically conductive adhesive, an electrically conductive polymer, an electrically conductive epoxy, an electrically conductive silicone, an electrically conductive polyamide, or an electrically conductive polyimide, such as those manufactured by Ablestick Corporation. An oxide-free electrical connection 143 is then formed between the optional ECA stripe 223 and the ground metallization 132 of the feedthrough capacitor. Electrical connection material 143 may comprise a solder or a second thermal-setting conductive adhesive. In an embodiment, the thermal-setting conductive material for the optional ECA stripe 223 can be the same material as the electrical connection material 143. The optional ECA stripe 223 of the present invention provides a robust connection therefore, allowing oxide-resistant coatings 165 comprising relatively expensive materials to be relatively thin. For example, it may not be possible to solder directly to a very thin oxide-resistant coating 165 as the thin coating layer can dissolve into the molten solder. For a thermal-setting conductive polyimide, it is also difficult to make a mechanically robust connection to such a thin oxide-resistant coating 165 without first depositing an optional ECA 223 stripe over it. By depositing the optional ECA stripe 223 over a very thin oxide-resistant coating 165 and then curing it without the feedthrough capacitor, one minimizes strains and stresses due to mismatches in coefficients of thermal expansion. Accordingly, adding the electrical connection 143 in a subsequent operation becomes very reliable and easy to accomplish in addition to providing a low resistance low impedance time-stable oxide-resistant electrical connection. The feedthrough capacitor 124 is generally disposed against the insulator 12*o* with an optional insulative washer 206, as shown in FIG. 25.

Referring once again to FIGS. 24 and 25, it is understood that both the oxide-resistant coating 165 and the optional ECA stripe 223 are proud of the surface of the ferrule 122. This is in marked contrast to and directly opposite of the gold pocket-pads 250, which reside in recessed pockets of the ferrule 122 as taught in U.S. Pat. No. 10,350,421. One is referred to the gold pocket-pad 250 of FIG. 23F herein. To form the gold pocket-pad, as described in U.S. Pat. No. 10,350,421, the content of which is incorporated herein fully by this reference, one must first form or machined a recess (pocket) in the ferrule itself. This swimming pool-like structure is formed, for example, by using powder metal technology such as metal injection molding or it is machined into the ferrule. The gold pocket-pad of the U.S. Pat. No. 10,350,421 invention requires that a gold (or equivalent) braze preform be disposed into the pocket-pad, and reflowed. Reflow of a gold braze preform is normally performed in a high temperature gold braze furnace. Forming of the pocket-pad can be a relatively expensive process and can also require a substantial amount of gold 250 to form a robust pocket-pad, the gold of which also thereby being relatively expensive. In the present invention, there is no need for a recessed pocket or swimming pool-type structure in the ferrule 122 at all. Instead, an oxide-resistant coating 165 is disposed proud (on the top of) the ferrule, over which the optional ECA stripe 223 is formed. Disposing an oxide-resistant coating 165 by any of the processes previously disclosed on the surface of the ferrule saves the molding and temperature processing or machining cost to form a swimming pool-like structure or gold pocket-pad as taught by U.S. Pat. No. 10,350,421. Accordingly, the oxide-resistant coatings of the present invention that are proud (in other words, on the ferrule surface) are very efficient as they require no molding, additional machining or additional gold braze preforms. The term "proud" as it relates to the oxide-resistant coating of the present invention is defined to be "proud" only in the sense that such oxide-resistant coatings, being only microns, sub-microns or Angstroms thick, are not readily visible to the human eye; nonetheless, a sophisticated electron microscope or other such advanced optical viewing instrument shows that the oxide-resistant coating is raised from the surface (proud) and not flush with the surface or recessed within the surface. In other words, a proud oxide-resistant coating of the present invention, which is not distinguishable with the human eye, is sitting proud of the titanium surface (has a thickness extending from the titanium surface).

Figure 26:
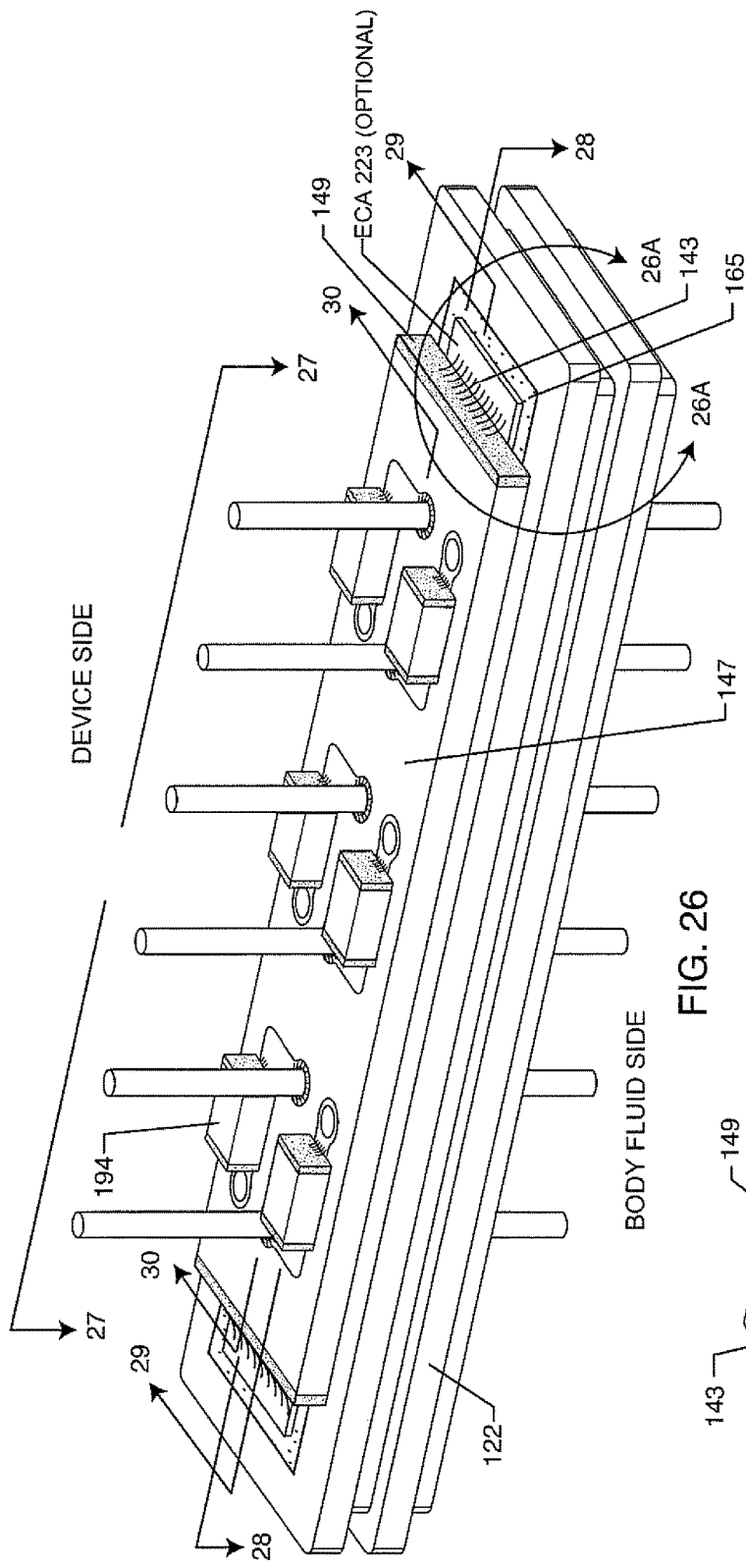
FIG. 26 illustrates an MLCC filter circuit board with ground attachments to an optional ECA stripe atop an oxide-resistant coating or layer on the feedthrough ferrule surface.
Figure 26A:
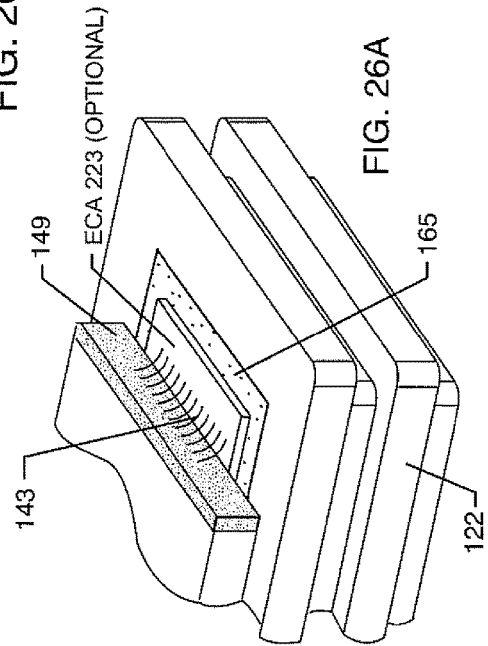
FIG. 26A is taken from section 26A-26A of FIG. 26 showing the oxide-resistant electrical connection.

FIG. 26 is an MLCC filter circuit board 147 with one or more embedded circuit board ground plates similar to FIG. 6C except that an optional ECA stripe 223 is disposed atop the oxide-resistant coating 165 of the present invention. Illustrated is an electrical connection using electrical connection material 143 connecting the optional ECA stripe and the ground edge metallization 149 of circuit board 147.

FIG. 26A is taken from section 26A-26A of FIG. 26 and shows an enlarged view of the electrical connection material 143 to the circuit board ground edge metallization 149 and the optional ECA stripe 223 disposed atop the oxide-resistant coating 165.

FIG. 27 is taken from section 27-27 of FIG. 26 and shows the top view of the circuit board 147 of FIG. 26. One can see the top view of the optional ECA stripe 223, the electrical connection material 143 and the oxide-resistant coating 165. The dashed lines of FIG. 27 indicate the hidden edge of the at least one embedded circuit board ground shield plate 156 of the MLCC filter circuit board 147.

FIG. 28 is taken from section 28-28 of FIG. 26. This cutaway shows the circuit board ground plate 156. It is appreciated that, while FIG. 28 illustrates the at least one ground plate, there may be a multiplicity or "n" number of ground plates 156, including embedded ground plates, an external ground plate, or both embedded and an external ground plate disposed between circuit board 147 and ferrule 122. Importantly, the ground plate 156 is disposed over the hermetic seal insulator 120 thereby blocking direct penetration of EMI into the interior of the AIMD housing 102. As previously disclosed, one or more ground plates 156 effectively shield and provide a low impedance path to decouple dangerous EMI signals to the AIMD system ground 144. The circuit board ground plates 156 of the present invention are also known as ground shield plates. MLCC circuit board ground plates are taught in U.S. Pat. No. 8,195,295, the contents of which are incorporated herein fully by reference.

Figure 29:
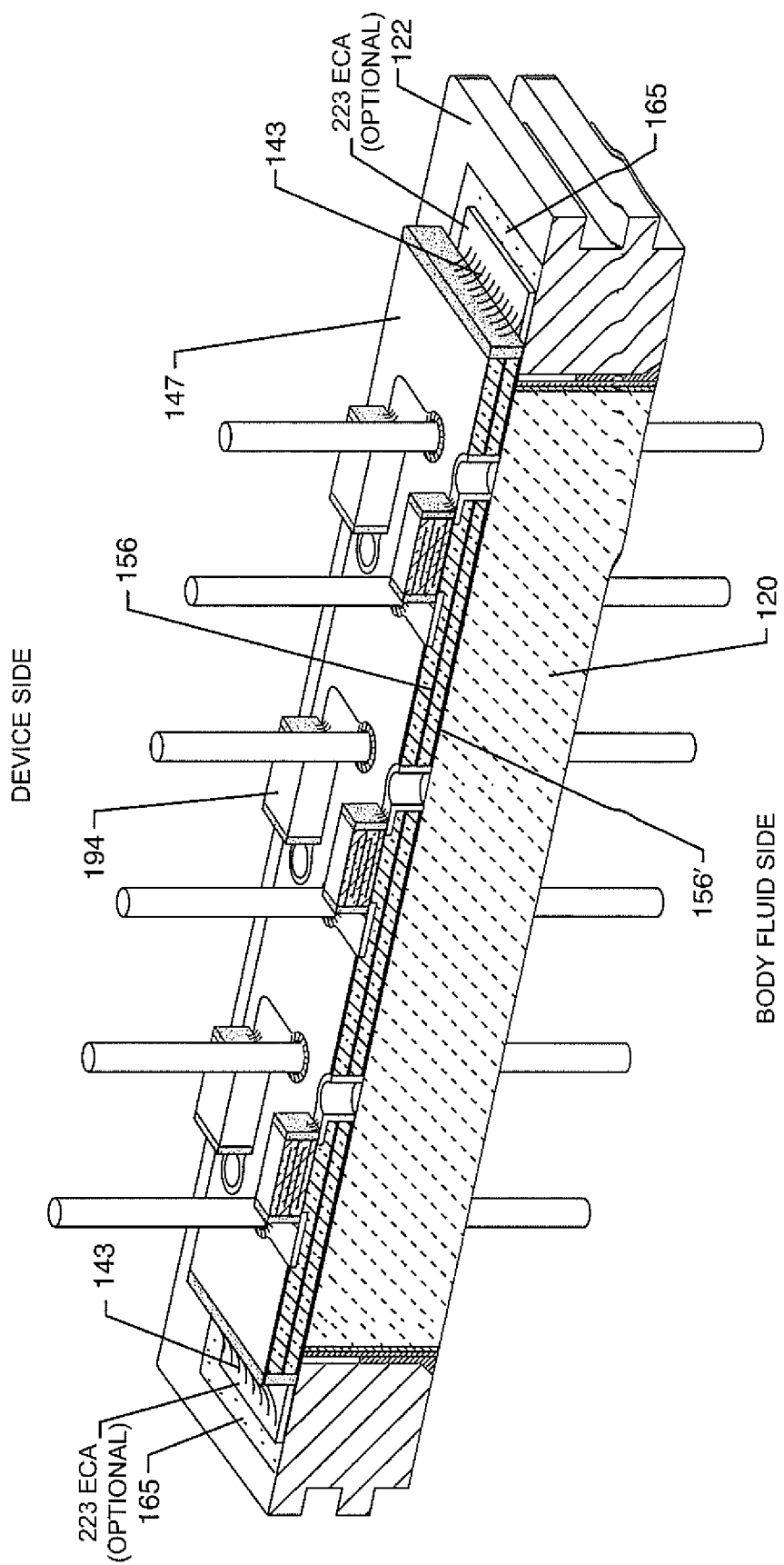
FIG. 29 is a sectional view taken from section 29-29 of FIG. 26 through the center line of the circuit board ground vias.

FIG. 29 is taken from section 29-29 of FIG. 26 and illustrates a cross section through the first row of MLCC chip capacitors. Referring once again to FIG. 29, one can see that there is an embedded ground shield plate 156 and an external ground shield plate 156', which is disposed between the bottom of the circuit board 147 and the top of the insulator 120. The external ground shield plate 156 is ideal since this space is as close to the insulator 120 as possible. This prevents waveguide action; wherein radiated EMI can couple or radiate through the edge of the MLCC filter circuit board 147.

Figure 30:
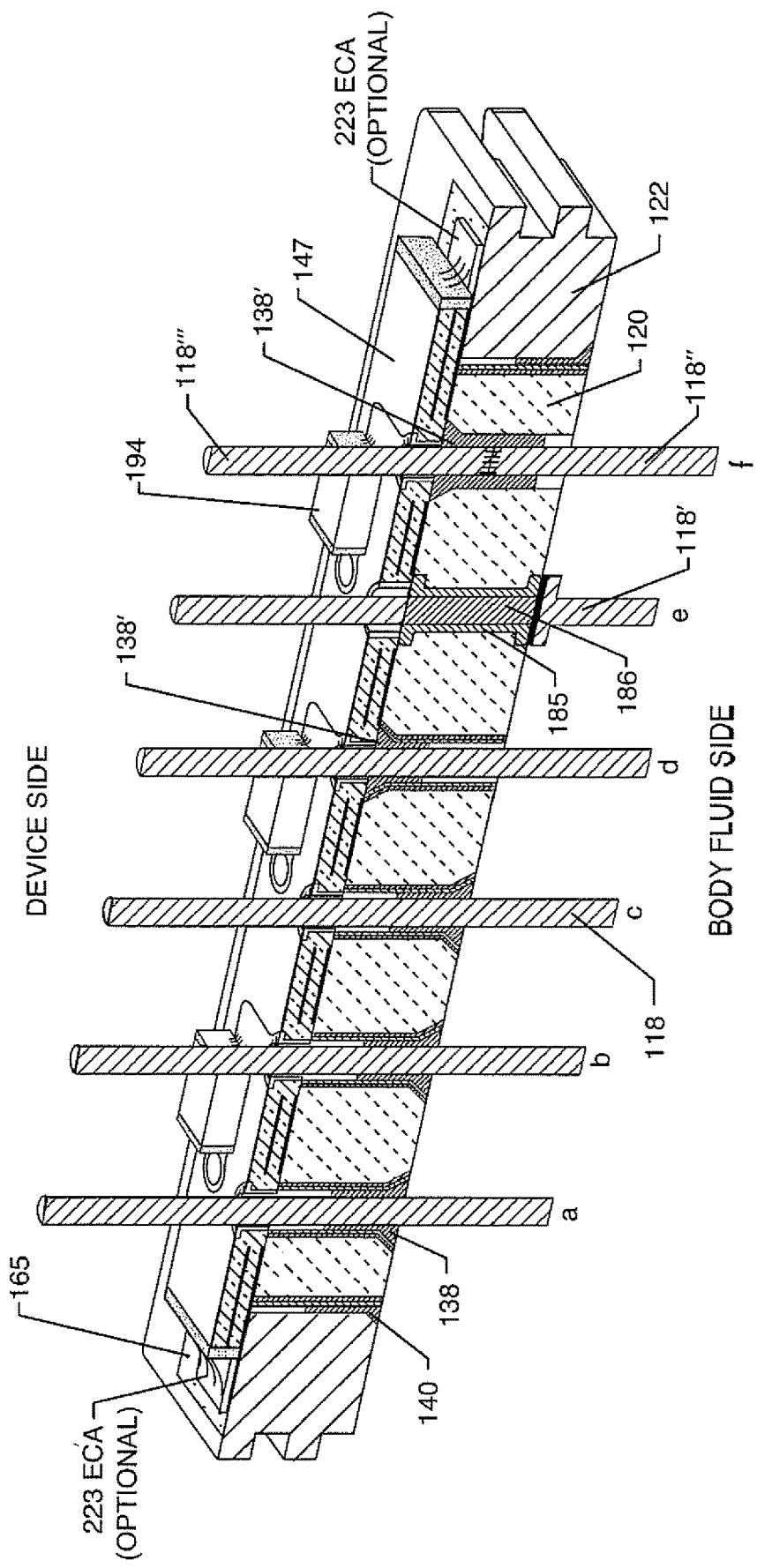
FIG. 30 is taken from section 30-30 of FIG. 26 showing a sectional view through the feedthrough active pins.

FIG. 30 is taken from section 30-30 of FIG. 26 and illustrates a cross section through the center of the active terminal pins of the MLCC filter circuit board 147. Leadwires or pins a, b and c have conventional gold brazes that hermetically seal the pins to the sealed insulator 120 hermetically sealed to the ferrule 122. As can be seen, the circuit board 147 and its associated MLCC chip capacitors 194 are oriented towards the device side of the AIMD. Gold brazes associated with pins a, b and c, are disposed on the body fluid side. Pin d is very similar to the gold brazes 138 for a, b and c, which are disposed on the body fluid side. On pin d, the gold braze 138' is disposed toward the device side. There is an advantage in disposing the gold braze 138' on the device side. That is, if pin d is a heavily oxidized pin, such as a niobium or tantalum pin, then a direct electrical connection can be made from the circuit board via associated with gold braze 138' such that an oxide-free electrical connection is made between gold braze 138', leadwire d and the MLCC chip capacitor ground termination. This is very important as it allows the use of very low-cost terminal pins.

Terminal pin e embodies the terminal pin post 118' disposed on a co-sintered via. In this case, the co-sintered vias are taught by U.S. Pat. No. 10,249,415, the content of which is herein incorporated fully by this reference. One is referred to FIG. 131 of the '415 patent for various embodiments of co-sintered vias. Referring once again to FIG. 30, there is a substantially pure platinum center core 186, which is surrounded by ceramic reinforced metal composite (CRMC). Referring once again to FIG. 30, terminal pin f is a two-part pin as taught by U.S. Pat. No. 10,272,251, the content of which is incorporated herein fully by this reference. Pin f allows a relatively inexpensive tantalum, niobium or titanium pin 118" to be disposed on the body fluid side, which is then co-brazed 138' such that a shorter platinum, palladium or platinum-iridium pin 118''' is disposed toward the device side. Two-part pins are thoroughly taught in the '251 patent. Another advantage of the two-part pin construct in pin f is that the gold braze 138' is disposed towards the device side. This has the same advantage as that previously described for pin d that would allow an oxide-resistant connection directly to the gold braze 138'. Referring once again to pin e of FIG. 30, it is appreciated that materials 185 and 186 can be combined in substantially pure platinum 186 as taught in U.S. Pat. No. 8,653,384 and its entire patent family. These patents disclose substantially pure platinum co-sintered vias with alumina insulators 120.

FIG. 31 is similar to FIG. 23H, except that the gold pocket-pad 250 has been replaced by an optional ECA layer 223 atop the oxide-resistant coating 165 of the present invention. In this case, circuit board 147 has a spatially aligned via hole that connects to the circuit board internal ground electrode plates 156. This via hole 143 replaces an edge connection of the circuit board. It is appreciated that any number "n" of ground via holes can be used in this manner with corresponding optional ECA stripes 223 each atop an oxide-resistant coating 165. Referring once again to FIG. 31, one can see that there is an optional barrier layer 166 that is represented by a thin black line between the oxide-resistant coating 165 and the ferrule 122. As previously described, this optional barrier layer can comprise any of the materials previously disclosed in order to prevent titanium oxides or titanium from migrating to the surface of the oxide-resistant coating, wherein the migrated titanium can now oxidize.

Referring back to FIG. 31, it is appreciated that the electrical connection material 143 can be a solid nail head structure. This is a machined or stamped pin or an eyelet. In the case that this was a solid material, there is an electrical connection between this solid construct 143 and the via hole metallization 145 (not shown). Referring once again to FIG. 31, it is appreciated that spatially aligning a grounded via hole over the optional ECA stripe 223 and the oxide-resistant coating 165 of the present invention, is equally applicable to internally grounded feedthrough capacitors 124'. Referring once again to FIG. 31, in the case where the electrical connection material 143 is a solid construct, there is also a solder or an ECA joint between the electrical connection material 143 and the optional ECA layer 223; or, in case where the optional ECA layer is not present, between the electrically conductive solid construct 143 and the oxide-resistant coating 165. This joint may be a thin layer of solder or ECA, which is not shown in FIG. 31. Referring once again to FIG. 31, in a preferred embodiment, the electrical connection material 143 can be an ECA or a solder or the like.

Figure 32:
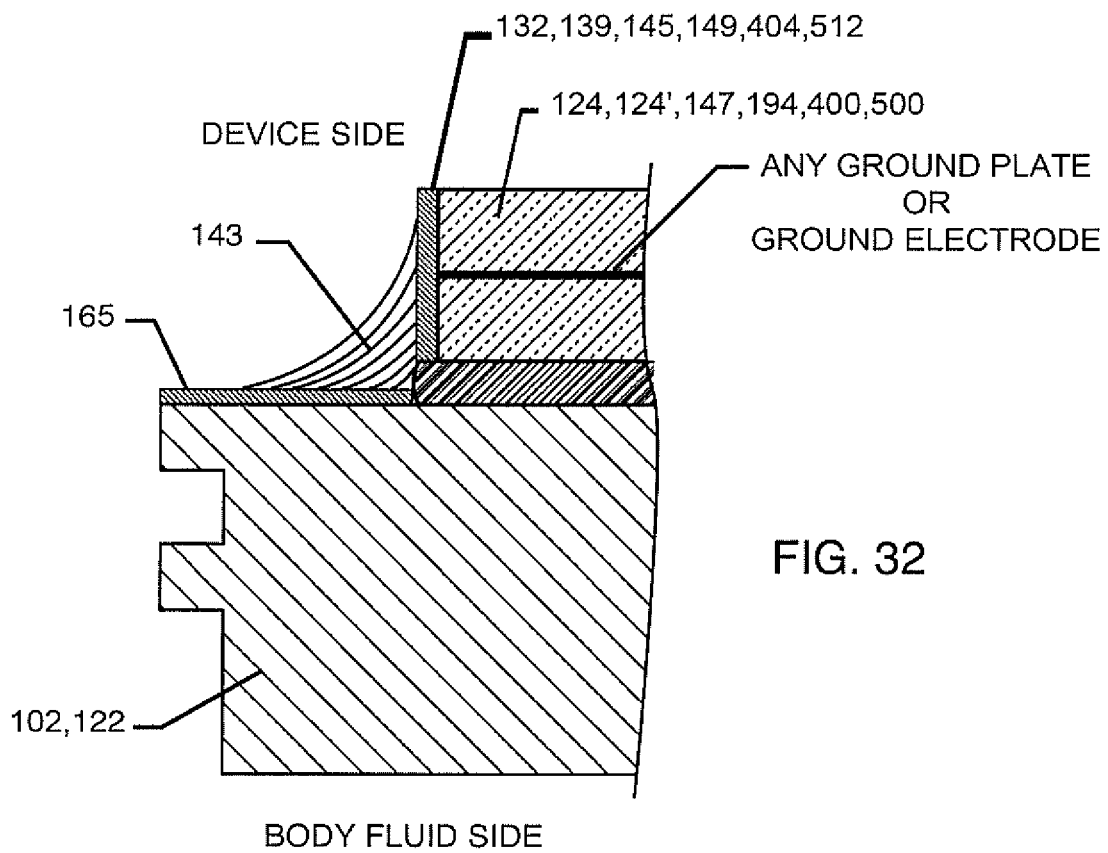
FIG. 32 illustrates that the system electrical ground connection of any type of passive EMI filter or filter circuit board can be made directly to the oxide-resistant coating of the present invention.

FIG. 32 illustrates an embodiment of the present invention, wherein the oxide-resistant coating 165 is sufficiently robust so that it can provide an oxide-free electrical connection without the need for an overlaying optional ECA stripe 223. In this case, the oxide-resistant coating 165 is visible to the naked eye. Illustrated is an exemplary low resistance low impedance electrical system ground connection 144 for filtering EMI of an AIMD. It is noted that the exemplar EMI filter circuit board ground termination of FIG. 32 is illustrative only. The termination of the exemplar EMI filter circuit board ground may instead be the ground terminations of one of a feedthrough capacitor 124, an internally grounded feedthrough capacitor 124', an MLCC chip capacitor 194, a flat-thru capacitor 400, or an X2Y attenuator 500, each similarly directly connectable to the oxide-resistant coating 165 illustrated. It is very important that all of these types of EMI filters comprise a system ground connection 144 that is essentially free of oxides. The ground plate of FIG. 32 may also be any ground plate, any ground electrode, or any of the ground plates or ground electrodes of any of the filters described herein. Accordingly, the termination material that electrically connects the oxide-resistant coating 165 and the filter (or other types of electrical components) can comprise an electrical connection either to a feedthrough or similar filter capacitor outside diameter perimeter metallization 132, a grounding pedestal or location for an internally grounded feedthrough or similar filter capacitor 132, the ground terminations for a flat-thru capacitor, the ground terminations for an X2Y attenuator, an ground edge metallization 149 for any type of filter or similar type circuit board 147, or a metallization or termination on the inside diameter of any circuit board or capacitive via hole 145.

Referring once again to FIG. 32, it is appreciated that direct attachment of the electrical ground material 143 to a robust oxide-resistant coating 165 is equally applicable to the ground via hole of feedthrough capacitors 124 or internally grounded feedthrough capacitors 124', circuit board 147 edge, ground or via hole metallizations, MLCC chip capacitor 194 ground metallization, or the ground metallization of flat-thru capacitors 400 or X2Y attenuators 500. Accordingly, the ground plate in FIG. 32 can be any ground plate or ground electrode of any of the capacitors or filter circuit boards of the present invention.

Referring again to FIG. 32, shown is an electrical connection material 143 electrically connecting an edge ground metallization 132, 139, 145, 149, 404, 512 to an oxide-resistant coating 165. The edge ground metallization electrically connects to at least one ground electrode plate of an electrical component, for example an EMI filter, and specific to FIG. 32, a non-limiting EMI filter circuit board. As such, an EMI filter may comprise one of an EMI filter capacitor 124, an EMI filter circuit board 147 (not labelled in FIG. 32), or both an EMI filter capacitor and an EMI filter circuit board. As previously disclosed, the EMI filter capacitor 124 may comprise one of a feedthrough filter 24, 24', a hybrid feedthrough capacitor 24", an MLCC chip capacitor 154, an X2Y attenuator 300, a flat-through capacitor 400, or combinations thereof. The EMI filter circuit board 147 may comprise one of an MLCC chip capacitor 154, an X2Y attenuator 300, a flat-through capacitor 400, or combinations thereof, electrically attached to an electrical ground path. In addition to the filter capacitors, the electrical ground path of the EMI filter circuit board 147 may comprise one or more electrical ground path components. The one or more electrical ground path components are selected from the group consisting of a trace, a filar, a filament, a wire, a lead, a leadwire, a lead wire, a terminal pin, a pin, a ribbon, a filled conductive via, a metallized conductive via, a filled conductive via having a metal insert, a metallized conductive via having a metal insert, a metal inserted into a via, a compliant electrical connector, a cable and combinations thereof. The one or more electrical ground path components may further be a single element or a multi-element component. Examples of multi-element components are: a multifilar element, a multifilament element, a two-part pin, a via having at least two metallization layers, a via having to different fill materials, a trace comprising at least two different materials or layers. In other words, a multi-element electrical ground path component comprises more than one material, part, piece, layer, or combinations thereof. Additionally, traces, filars, filaments, wires, leads, leadwires, lead wires, pins, ribbons, cables and the like may be woven, twisted or coiled. The at least one ground electrode plate may comprise either an internal ground electrode plate or an external ground electrode plate. It is contemplated that the EMI filter circuit board 147 may comprise at least one ground RF shield plate or a plurality of ground RF shield plates. This shield plate(s) also acts as an electrode desirably forming parasitic capacitance (additional filtering) between the ground shield plate(s) and, for example, an active circuit trace (in this case, the circuit board material itself) acts as a dielectric. As taught in U.S. Pat. No. 8,195,295 the active traces can be disposed on one side of the ground plate(s), the content of which is fully incorporated herein by this reference. The '295 patent also teaches that the active traces may be disposed between shield plates to further increase parasitic capacitance. In this case, this parasitic capacitance provides additional filtering. Additionally, the active circuit traces themselves have inductance. However, this inductance is in series between the conductive pathways from implantable lead conductors to the inside of the active implantable medical device. This means that the inductance is not in the filter system ground connection but is disposed along the path that EMI must follow. This desirably turns the EMI filter into a T filter which further increases its filter performance, also known as insertion loss. It is also contemplated that the MLCC, X2Y attenuator or flat-through EMI filter capacitors and/or the EMI filter circuit board may comprise one or more external ground RF shield electrode plates. The external ground electrode plates may be disposed on one of the top surface, the bottom surface or both the top and the bottom surfaces of the EMI filter capacitor and/or the EMI filter circuit board. The electrical connection material may comprise a solder, a thermal-setting conductive adhesive, a conductive epoxy, a conductive polyimide, a low temperature braze or any suitable electrical connection material.

Prior to the application of the oxide-resistant coating or layer 165 of the present invention, an additional embodiment of the present invention, is to lay down a barrier layer (or layers) 166 (FIG. 31), which can comprise a very thin sputter layer of nickel, palladium or even platinum. This prevents titanium oxides from diffusing or migrating through the oxide-resistant coating or layer to the surface, for example, if the oxide-resistant coating 165 is gold. Other barrier layer options instead of or in combination with nickel, palladium, and platinum include: rhodium, ruthenium, molybdenum, and chromium; alloys, such as nickel-vanadium, nichrome, nickel-iron, palladium-cobalt, cobalt-tantalum; nickel alloys, palladium alloys, platinum alloys; and electrically conductive nitrides, such as titanium nitride, zirconium nitride, hafnium nitride, vanadium nitride, tantalum nitride, molybdenum nitride, and tungsten nitride may be used. The term "sputter layer" is herein defined as a thin film coating or layer that covers a surface or surfaces of a component, an assembly, a substrate, a structure or an object. A sputter layer (oxide-resistant sputter layer 165 or barrier sputter layer 166) may comprise a single material or may alternately comprise multiple materials. It is understood that a sputter layer may comprise one or more layers. Sputter layers 165, 166 may be applied by one of the following methods: physical vapor deposition, chemical vapor deposition, electrostatic spray assisted vapor deposition (ES-AVD), electron beam physical vapor deposition (EBPVD), ion plating, ion beam assisted deposition (IBAD), magnetron sputtering, pulsed laser deposition, sputter deposition, vacuum deposition, pulsed electron deposition (PED), plating, electroless plating, electroplating, spraying, painting, plasma spraying, thermal spraying, spin coating, dip coating metal foil lamination, and thin film deposited layers. Thin sputter layers 165 for oxide-resistant attachments benefit from thin film sputter layer "stackup" systems that inhibit metal and/or oxide migration through the oxide-resistant layer, as such oxide migration through the oxide-resistant layers can eventually result in brittle connections for metal migrations and/or increased electrical connection resistance for oxide migrations. Both are undesirable, as either one independently or in combination comprise the reliability and integrity of the electrical and mechanical connections.

Barrier layers and/or barrier sputter layers provide the following benefits to AIMD component mechanical and electrical connections: (1) prevents interdiffuision of metals up or down through the sputter layer stackup system which can compromise mechanical connection integrity; and, (2) prevents migration of oxides up or down through the sputter layer stackup system, which can compromise electrical integrity. As an example, when an essentially pure gold metal is used as the oxide-resistant sputter layer, a preferred sputter layer stackup system comprises one or more barrier layers atop of which the gold sputter layer 165 is applied. An optional ECA stripe 223 can also then be applied thereon to provide a reliable mechanical and low resistance low ESR electrical connection. Regardless of the barrier material selected, a barrier layer 166 (FIG. 31) having a thickness of 100 Angstroms to 4000 Angstroms (0.01 micron to 0.4 microns; 10 nm to 400 nm), depending on the metal selected, is sufficient to provide robust mechanical and reliable electrical connection. In some cases, the barrier layer may comprise two or more layers, each layer having a preferred thickness to achieve an overall barrier layer stackup thickness of about 100 Angstroms to about 4000 Angstroms (0.01 micron to 0.4 microns; 10 nm to 400 nm).

A barrier layer 166 (FIG. 31) is an optional consideration for oxide-resistant sputter layers 165 applied to a titanium or any oxidizable surface. Deciding to include a barrier layer is dependent on the stability of the oxidizable surface in contact with the oxide-resistant sputter layer, which is why titanium, having such a tremendous affinity for oxygen is such a valuable exemplar for oxide free electrical attachment. In fact, titanium is actually used as an oxygen getter in various applications. Therefore, a gold oxide-resistant layer on a titanium surface is an excellent example for understanding diffusion. It is known that at elevated temperatures, titanium (Ti) can interdiffuse with the gold (Au) to either form a Ti—Au intermetallic, or, the titanium can actually diffuse to the free surface of the gold to form titanium oxides, which, in turn, can cause undesired ohmic resistance. In general, interdiffusion of thin films occur by way of lattice defects in the atomic structure of a material, for example, vacancies, dislocations and grain boundaries.

The oxide-resistant coating 165 of FIG. 32 comprises an oxide-resistant surface area, the oxide-resistant area residing at least on a titanium surface of an AIMD component. Both an oxide-resistant layer and an oxide-resistant area may be disposed on a titanium surface in accordance with the processes previously disclosed, namely, by physical vapor deposition (PVD), chemical vapor deposition (CVD), electrostatic spray assisted vapor deposition (ESAVD), electron beam physical vapor deposition (EBPVD), ion plating, selective electroplating, ion beam assisted deposition (IBAD), magnetron sputtering, pulsed laser deposition, sputter deposition, vacuum deposition, pulsed electron deposition (PED), plating, electroless plating, electroplating, spraying, painting, plasma spraying, thermal spraying, spin coating, dip coating, metal foil lamination, metal cladding and thin film deposited layers, either fully or selectively disposed. An oxide-resistant area may comprise one or more layers. Likewise, as previously disclosed, the above processes may be used to deposit metals such as gold, gold alloys, rhodium, rhodium alloys, platinum, platinum alloys, platinum-iridium alloys, palladium, palladium alloys, nitinol, cobalt-chromium alloys and combinations thereof.

In an embodiment comprising an oxide-resistant coating area atop a titanium surface, it is important to emphasize that a thorough (essentially total) removal of any titanium oxides prior to disposing the oxide-resistant material. The thorough essentially total removal of titanium oxides ensures a complete and continuous surface covering. Methods of oxide removal include mechanical, chemical, electrochemical and plasma processes. Mechanical processes include, but are not limited to, sanding (for example, with alumina abrasive paper or an alumina abrasive mat), grinding, grit blasting (for example with alumina in accordance with MIL-G-21380 Type 1 or glass beads in accordance with MIL-G-9954 sizes 10-13), brushing with a stainless-steel brush, tumbling, and combinations thereof. Chemical processes include, but are not limited to, immersing in a hot concentrated alkaline solution (for example, a highly alkaline cleaner containing sodium gluconate and corrosion inhibitors at 93° C. to 148° C., a concentrated aqueous alkaline hydroxide solution and a calcium salt such as calcium oxide), acid etching (for example, as disclosed in U.S. Pat. No. 5,763,377, the content of which are fully incorporated herein by this reference, strong nitric acids, strong sulfuric acids, a hydrofluoric-containing acid such as $CrO_3$ 100 g/l and 40% HF 20 ml/l; 10% HF-30% $HNO_3$-60% $H_2O$; a mixture of nitric acid at about 40% by volume and hydrofluoric acid at about 2-3% by volume), or electropolishing (for example, using a chloride-based solution, a sulfuric acid-methanol-based solution, or any of the perchlorate-free electrolytes disclosed by Piotrowski et al, in the paper entitled: "Electropolishing of Titanium and Titanium Alloys in Perchlorate-Free Electrolytes", the content of which is fully incorporated herein by this reference). Ideally, cleaned titanium parts are stored in a vacuum or inert gas until actually disposing the oxide-resistant area(s) to prevent oxide re-formation under the oxide-resistant area(s). Additionally, oxide-resistant coating area(s) can be disposed in a vacuum or in an inert gas environment to minimize oxide re-formation under the oxide-resistant area(s).

Oxide-resistant coatings can alternatively be disposed on a titanium surface using braze materials to bond an oxide-resistant film, foil or pad to the titanium surface. The braze materials for bonding to a titanium surface (in weight percent) may be selected from the group consisting of copper/silver (28/72)—melting point (MP) 780° C., indium/copper/silver (10/27/63)-MP 685-730° C., gold/nickel (82/18)—MP 950° C., nickel/gold/copper (3/35/62)—MP 1000-1030° C., gold/nickel/titanium compositions including those disclosed in U.S. Pat. No. 4,938,922, the content of which is fully incorporated herein by this reference, Johnson Matthey silver-copper eutectic and pure metal brazes, Pallabraze alloys and Orobraze alloys. Furthermore, pending the application and an OEM's manufacturing processes, it may even be desirable to avoid titanium's beta-transus temperature, which is the critical temperature of the α↔β phase transformation of titanium or its alloys, as the nature of titanium and titanium alloys determines important temperature/time limits of brazing thermal cycles. The temperature/time limits of titanium and its alloys are caused by undesirable changes in the microstructure and properties of the titanium and titanium alloy metal and potentially the oxide-resistant metal as well. The temperature/time limits may also be defined by a potential formation of brittle intermetallics at the interface between the titanium/titanium alloy metal and the oxide-resistant metal. Hence, low temperature oxide-resistant attachment methods are required. As such, oxide-resistant areas can alternatively be disposed on a titanium surface by using a low-melting-point brazing metal. Exemplary compositions of low-melting-point braze materials include aluminum-based, aluminum-silver, aluminum-silicon, silver-based, titanium-based, palladium-based, and zirconium-based systems. An exemplary embodiment of an oxide-resistant area on a titanium surface comprises a brazing temperature less than 1000° C. Another exemplary embodiment of an oxide-resistant area on a titanium surface comprises a low-melting-point braze material. Non-limiting examples of low-melting-point braze materials that are oxide-resistant material-based (in weight percent) include: 81Au-18In having a brazing temperature of 530° C. and 88Au-12Ge having a brazing temperature of 356° C. Other gold alloy brazes that may be used to bond an oxide-resistant film, foil or pad to a titanium surface are provided in Table 3 below.

TABLE 3

| | Composition (weight percent) | | | | | Melting Rnage | | | |
| | | | | | | Liquidus | | Solidus | |
| No. | Au | Cu | Ni | Ag | Pd | Other | °C. | °F. | °C. | °F. |
| --- | --- | --- | --- | --- | --- | --- | --- | --- | --- | --- |
| 1 | 92 | | | | 8 | | 1240 | 2264 | 1200 | 2192 |
| 2 | 50 | | 25 | | 25 | | 1121 | 2050 | 1102 | 2016 |
| 3 | 35 | 62 | 3 | | | | 1030 | 1886 | 1000 | 1832 |
| 4 | 82 | | 18 | | | | 950 | 1742 | 950 | 1742 |
| 5 | 81.5 | 16.5 | 2 | | | | 925 | 1697 | 910 | 1670 |
| 6 | 60 | 20 | | 20 | | | 845 | 1553 | 835 | 1535 |
| 7 | 30 | | 36 | | 34 | | 1169 | 2136 | 1135 | 2075 |
| 8 | 41 | | 22 | | 27 | 10 Cr | 1110 | 2030 | 1054 | 1930 |
| 9 | 70 | | 22 | | 8 | | 1037 | 1899 | 1005 | 1841 |
| 10 | 20 | 78 | | | | 2 In | 1025 | 1877 | 975 | 1787 |
| 11 | 35 | 65 | | | | | 1010 | 1850 | 990 | 1814 |
| 12 | 37.5 | 62.5 | | | | | 1005 | 2841 | 985 | 1805 |
| 13 | 40 | 60 | | | | | 1000 | 1832 | 980 | 1796 |
| 14 | 72 | | 22 | | | 6 Cr | 1000 | 1832 | 975 | 1787 |
| 15 | 80 | 20 | | | | | 910 | 1670 | 908 | 1666 |
| 16 | 60 | 37 | | | | 3 In | 900 | 1652 | 860 | 1580 |
| 17 | 75 | 20 | | 5 | | | 895 | 1643 | 885 | 1625 |
| 18 | 88 | | | | | 12 Ge | 356 | 673 | 356 | 673 |
| 19 | 50 | 50 | | | | | 970 | 1778 | 956 | 1751 |
| 20 | 5 | | | | 20 | 75 Pt | 1695 | 3083 | 1645 | 2993 |
| 21 | 65 | | | | 35 | | 1440 | 2624 | 1428 | 2601 |
| 22 | 75 | | | | 25 | | 1410 | 2570 | 1380 | 2516 |
| 23 | 75 | | | | | 25 Pt | 1410 | 2570 | 1210 | 2210 |
| 24 | 87 | | | | 13 | | 1305 | 2381 | 1260 | 2300 |
| 25 | 65 | | 35 | | | | 1075 | 1967 | 965 | 1769 |
| 26 | 30 | 70 | | | | | 1035 | 1895 | 1005 | 1859 |
| 27 | 32 | 65 | 3 | | | | 1025 | 1877 | 990 | 1814 |
| 28 | 94 | 6 | | | | | 990 | 1814 | 965 | 1769 |

TABLE 3-continued

| Composition (weight percent) | | | | | | Melting Rnage | | | |
|---|---|---|---|---|---|---|---|---|---|
| | | | | | | Liquidus | | Solidus | |
| No. | Au | Cu | Ni | Ag | Pd | Other | °C. | °F. | °C. | °F. |
| 29 | 51.7 | 45.5 | | 2.8 | | | 963 | 1765 | 924 | 1695 |
| 30 | 58.3 | 39.6 | | 2.1 | | | 921 | 1690 | 906 | 1660 |

Another exemplary embodiment of an oxide-resistant area on a titanium surface comprises a low-melting-point braze material, the low-m citing-point braze material being conventional titanium-based braze materials, for example, see Table 4 below; and conventional silver-copper based brazing materials, such as, but not limited to, Ag—Cu-15, Ag-28Cu—Ti2, and Ag-28Cu-0.2Li. It is noted that to avoid heating above the α↔β phase transformation of titanium and/or its alloys, the brazing temperature of α-titanium alloys should be below 900° C.; the brazing temperature of the α+β titanium alloys should be below 935° C.; the brazing temperature of most of the near-O titanium alloys should be below 870° C.; and the brazing temperature of the β-titanium alloys should be below 800° C., preferably below 760° C.

TABLE 4

| Composition (weight percent) | | | | Liquidus | | Solidus | |
|---|---|---|---|---|---|---|---|
| Ti | Zr | Cu | Ni | °C. | °F. | °C. | °F. |
| 45 | 45 | 5 | 5 | 810 | 1490 | 780 | 1436 |
| 42.5 | 42.5 | 10 | 5 | 800 | 1472 | 790 | 1454 |
| 42.5 | 42.5 | 5 | 10 | 820 | 1508 | 800 | 1472 |
| 40 | 40 | 15 | 5 | 815 | 1499 | 795 | 1463 |
| 40 | 40 | 10 | 10 | 820 | 1508 | 805 | 1481 |
| 40 | 40 | 5 | 15 | 825 | 1517 | 795 | 1463 |
| 37.5 | 37.5 | 15 | 10 | 815 | 1499 | 805 | 1481 |
| 37.5 | 37.5 | 10 | 15 | 840 | 1544 | 815 | 1499 |
| 36 | 36 | 0 | 28 | 880 | 1616 | 820 | 1508 |
| 35 | 35 | 15 | 15 | 820 | 1508 | 770 | 1418 |
| 35 | 35 | 5 | 25 | 870 | 1598 | 840 | 1544 |
| 32.5 | 32.5 | 20 | 15 | 890 | 1634 | 830 | 1526 |
| 32.5 | 32.5 | 15 | 20 | 860 | 1580 | 835 | 1535 |
| 32.5 | 32.5 | 10 | 25 | 860 | 1580 | 825 | 1517 |
| 32.5 | 32.5 | 5 | 30 | 900 | 1652 | 880 | 1616 |
| 30 | 30 | 20 | 20 | 870 | 1598 | 840 | 1544 |
| 30 | 30 | 15 | 25 | 855 | 1571 | 830 | 1526 |
| 27.5 | 27.5 | 40 | 5 | 840 | 1544 | 815 | 1499 |
| 27.5 | 27.5 | 30 | 15 | 1030 | 1886 | 990 | 1814 |
| 27.5 | 27.5 | 10 | 35 | 1035 | 1895 | 970 | 1778 |
| 25 | 25 | 50 | 0 | 815 | 1499 | 780 | 1436 |
| 25 | 25 | 25 | 25 | 980 | 1796 | 860 | 1580 |
| 60 | 0 | 25 | 15 | 930 | 1706 | — | — |

The limitation of brazing temperatures by the beta-transus temperature is especially important for thin-wall structures, as undesirable structural changes can be made to the entire titanium thin-walled structure, rendering the titanium structure unusable. It is noted that the higher the brazing temperature, the more intensive the reaction occurs between the braze metal and the titanium/titanium alloy metal. Consequently, a thicker intermetallic layer may be formed at the interface of the oxide-resistant material and the titanium surface. A thicker intermetallic layer can be beneficial, for example, when the oxide-resistant material is a thin gold film, foil, or pad. Although a thin gold film, foil, or pad is highly resistant to forming oxides and is highly conductive, when the gold film, foil or pad becomes too thin, the gold, due to its large lattice structure, can be relatively "porous". If the gold film, foil or pad is porous because it is too thin, the titanium can migrate through the thin gold to the free surface of the gold. When the gold disposed on a titanium surface is too thin, the titanium can diffuse along the grain boundaries at the gold/titanium interface to the free surface of the thin gold, where the titanium can then be oxidized. Accordingly, a thicker braze material can prevent migration of titanium through a thin gold film, foil or pad. It is noted that the first metal layer disposed prior to disposing the oxide-resistant metal layer as previously disclosed may be an intermediary or barrier layer that mitigates migration of titanium through oxide-resistant areas that are either too thin or porous. The thickness of an intermediary or barrier layer should be >10 microns for oxide-resistant gold layers that are <0.5 microns thick.

Oxide-resistant coatings can alternatively be disposed on a titanium surface by using a laminated brazing foil disposed on the surface of the titanium. An oxide-resistant metal foil may be placed atop the laminated brazing foil. Induction heating can be used to melt the brazing foil thereby bonding the oxide-resistant metal foil to the surface of the titanium. An exemplary embodiment of an oxide-resistant area on a titanium surface comprises a laminated brazing foil and pure gold (99.99%) metal oxide-resistant foil. Other oxide-resistant foils that can be used in addition to gold include platinum, palladium, rhodium and alloys or combinations thereof. A laminated brazing foil may be selected from the group consisting of gold-based braze materials, titanium-based braze materials, for example, see tables 2 and 3 above; silver-copper based brazing materials, such as, but not limited to, Ag—Cu-15, Ag-28Cu-Ti2, and Ag-28Cu-0.2Li; and amorphous brazing foils, for example, but not limited to, Ti-37.5Zr-15Cu-10Ni, Ti-35Zr-15Cu-15Ni, Ti-25Zr-50Cu with melting points approximately 100° C. lower than the conventional titanium-based braze materials, which is greater than 1000° C.

Oxide-resistant areas can alternatively be made on a titanium surface as part of a titanium surface treatment. For example, an oxide-resistant metal can be achieved by precipitating oxide-resistant particles on a titanium surface and then sintering said oxide-resistant particles to the titanium surface. An exemplary embodiment of an oxide-resistant area on a titanium surface is a sintered-layer comprises oxide-resistant particles selected from the group consisting of gold, platinum, palladium, rhodium, and mixtures or alloys thereof.

Oxide-resistant areas can alternatively be disposed on a titanium surface by active metal brazing. The titanium oxide that makes titanium metal corrosion resistant is easily dealt with by using an active braze alloy permitting effective wetting of the braze material by the oxide-resistant material while reacting the active element of the braze material with the oxides of the titanium, thereby forming a metallurgical bond between the oxide-resistant material and the titanium surface. Active brazing alloys can be mixed metal preforms or have a primary braze material forged or clad to a small amount of the oxide-resistant braze metal. An exemplary, embodiment of an oxide-resistant area on a titanium surface comprises an active braze material having an active element that reacts with any oxides, carbides, or nitrides on the titanium surface, thereby allowing the oxide-resistant metal to wet and bond to the titanium surface. Alternative active braze elements to titanium or in combination with titanium include hafnium, vanadium, zirconium and chromium. The nature of the interface layer formed because of the reaction of the active element is determined by the concentration of said active element and the time/temperature parameters of the brazing cycle.

Oxide-resistant coating areas comprising electroconductive oxides and/or nitrides can alternatively be disposed on a titanium surface. An embodiment comprises a titanium nitride oxide-resistant area. Titanium nitride is chemically and thermally stable and has several crystallographic phases depending on temperature and nitrogen atomic percentage, however, its primary nitride phase TiN crystallizes in the rock salt structure (Fm3m) with a lattice parameter of 4.24 angstrom for the stoichiometric TiN (N/Ti=1). The rock salt structure of TiN is indicative of an increase in the number of valence electrons from titanium to titanium nitride TiN, the nitrogen being responsible for the valence electron increase. The electrical conductivity of TiN is of the order of magnitude of pure metals due to the intersection of the valence band of the Ti 3d electrons with the Fermi level (EF). The electrical resistivity of TiN thin films strongly depends on processing parameters and film properties, particularly the film properties of film defects, impurities, microstructure, composition and fundamental film structure. The presence of point defects together with the grain boundaries also modifies the electron interactions of the Ti and N atoms and the electronic structure of the pure stoichiometric TiN. Additionally, the properties of TiN are extremely sensitive to the nitrogen fraction. Thus, process control is important. In summary, stoichiometric crystalline TiN is a good electrical conductor and is chemically and thermally stable, with the electrical conductivity of titanium nitride films largely being attributed to TiN's unique band an electronic structure. As such, because of its stability and electrical conductivity, TiN may alternatively be used as an intermediary or barrier layer for an oxide-resistant area in addition to being an oxide-resistant layer on a titanium surface. It is contemplated that other stable electroconductive transition metal oxides and/or nitrides can alternately be used instead of titanium nitride as either an oxide-resistant area or a barrier layer for an oxide-resistant area. Examples of other electroconductive transition metal nitrides in addition to TiN include ZrN, HfN, VN, NbN, TaN, MoN, and WN. One example of an electroconductive transition metal oxide is $RuO_2$.

Figure 32A:
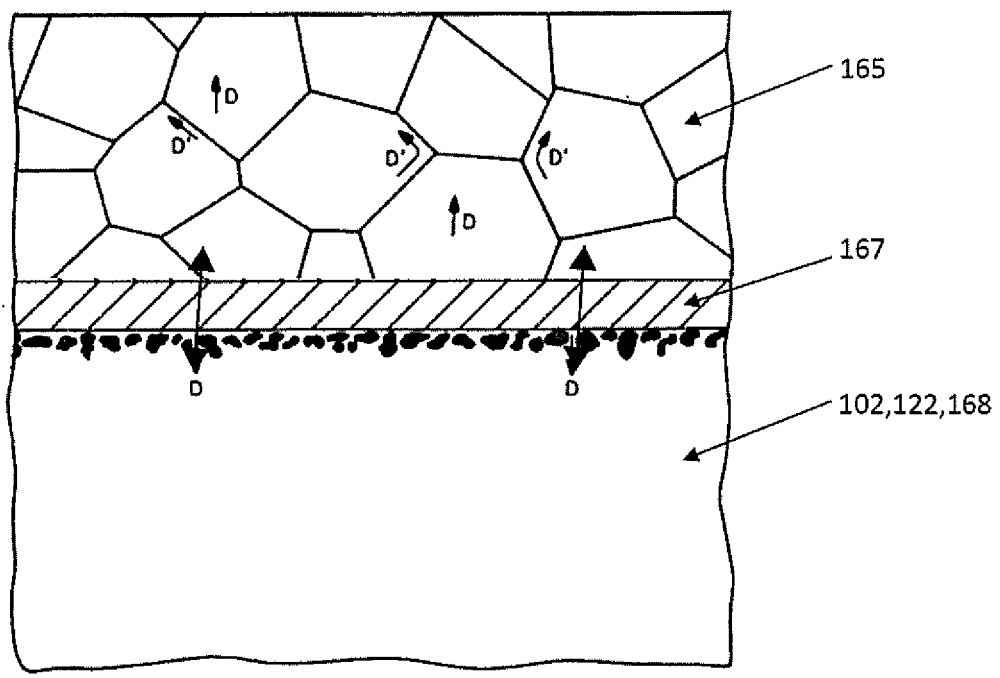
FIG. 32A is a schematic representation of diffusion-related mechanisms of oxidizable base metal substrate materials through an oxide-resistant coating layer, which can cause unstable and unreliable AIMD electrical connections.

FIG. 32A is a schematic representation of three possible diffusion mechanisms that can degrade the performance of an electrical connection to an oxide-resistant coating atop an oxidizable metal surface, especially when the oxide-resistant coating is a thin oxide-resistant layer. Illustrated is an oxide-resistant coating 165 atop an oxidizable metal surface 102,122,168. Element 167 represents an exaggerated representation of the interface between the oxide-resistant coating 165 and the oxidizable metal surface 102,122,168. Three diffusion behavior mechanisms are schematically shown: (1) lattice diffusion, which involves vacancy atom exchange; (2) defect path diffusion, which involves grain boundaries, dislocations and twin boundaries; and (3) interdiffusion at an interface, which involves ordered intermetallic phases at the interface.

Lattice diffusion is illustrated as large black irregular shapes along the mating line of the oxide-resistant layer 165 and the oxidizable metal material 102, 122, 168. It is by lattice diffusion that the atoms in the oxide-resistant layer 165 and the oxidizable metal material 192,122,168 intermingle so that at the mating line each material becomes increasingly similar in composition to the other while totally in the solid state. Lattice diffusion is driven by temperature, for example, the temperature rises caused by welding processes, and as the temperature rises lattice diffusion initiates. Lattice diffusion is represented as D at the black irregularly shaped region along the mating surface of FIG. 32A. The double headed arrow at D indicates lattice diffusion being a two-way diffusion mechanism.

Defect path diffusion is considered a rapid diffusion mechanism in that defect path diffusion has a lesser dependence on temperature, thus usually becomes dominant at lower temperatures such as ECA stripe curing temperatures or even at smaller temperature rises only slightly above room temperature depending on the specific materials of the oxide-resistant coating 165 and the oxidizable surface 102, 122,168. Defects like grain boundaries, dislocations and twin boundaries, which are common and practically unavoidable in metals, serve as rapid transport pipes through the oxide-resistant coating 165. Defect path diffusion is particularly relevant in thin gold films where the techniques of application such as electrodeposition, sputtering and vapor deposition all provide very fine grained structures, specifically because fine grained structures are riddled with high defect density (hence the term "porous gold" used earlier in the present application). The defect path diffusion coefficient D' shown along the grain boundaries of the oxide-resistant coating 165 in FIG. 32A can typically be four to six orders of magnitude larger than the lattice diffusion coefficient D at substantially lower temperatures than that induced by welding. Defect path diffusion is of primary concern in relation to the formation on gold layers of surface films of base metal oxides, such as the titanium oxides previously disclosed, which can degrade such properties as electrical resistance, bondability, and, most importantly, AIMD EMI filter performance as taught herein.

Interdiffusion at the interface results in the possible formation of ordered intermetallic phases at the interface of the oxide-resistant coating 165 and the oxidizable surface 166. In the exemplar of gold and titanium, this can take the form of layers growing at the original gold-titanium interface, depicted in FIG. 32A as an exaggerated (not to any scale) interface 167. The interface 167 may comprise material phases, intermetallics, diffusion gradients, and combinations thereof, which comprise the chemical elements of the oxide-resistant coating 165 and the oxidizable metal surface 102, 122,168 on which the oxide-resistant layer is disposed. The interdiffusion layer growth rate is generally relatively slow at low temperatures, however, may be accelerated at higher temperatures such as ECA cure temperatures and then exacerbated by subsequent welding temperature rises during AIMD assembly. Depending on the thickness of the gold oxide-resistant coating 165, for example, thicknesses greater than 1 μm, there may be little, even no influence on the gold surface electrical properties. For thin gold oxide-resistant coating 165 thicknesses, for example, less than 1 μm, substantial influence on the gold electrical properties can be observed. Additionally, ordered intermetallic often brittle layers are generally created, which can also influence the mechanical integrity of the electrical connection. It is even possible that for the gold oxide-resistant coating to be susceptible to fracture and flake off as a result of any introduction of even mild stresses being applied (small shocks or vibrations). For the Ti—Au system, titanium atoms diffuse into the gold typically in the grain boundaries, thereby either forming intermetallics, such as $TiAu_4$, $TiAu_2$, TiAu, and $Ti_3Au$, or diffusing up to the gold free surface to react with oxygen thereby forming both anatase and rutile titanium dioxide $TiO_2$. Of significance is that Ti diffusion to the Au free surface can occur at processing temperatures as low as 200° C. to 400° C., such when ECA stripes are cured or titanium seam welding is done. Because surface oxidation of titanium occurs at the gold free surface, the titanium oxidation reaction itself creates a chemical potential sink, which continually drives diffusion of the titanium through the gold, thereby supporting and enhancing a continuous titanium oxidation process. Since oxygen enhances diffusion of the Ti—Au system, the very rapid diffusion of the titanium through the gold layer and the formation and thickening of the titanium oxide at the free surface explains the undesirable increase in ohmic resistance over time.

Figure 32B:
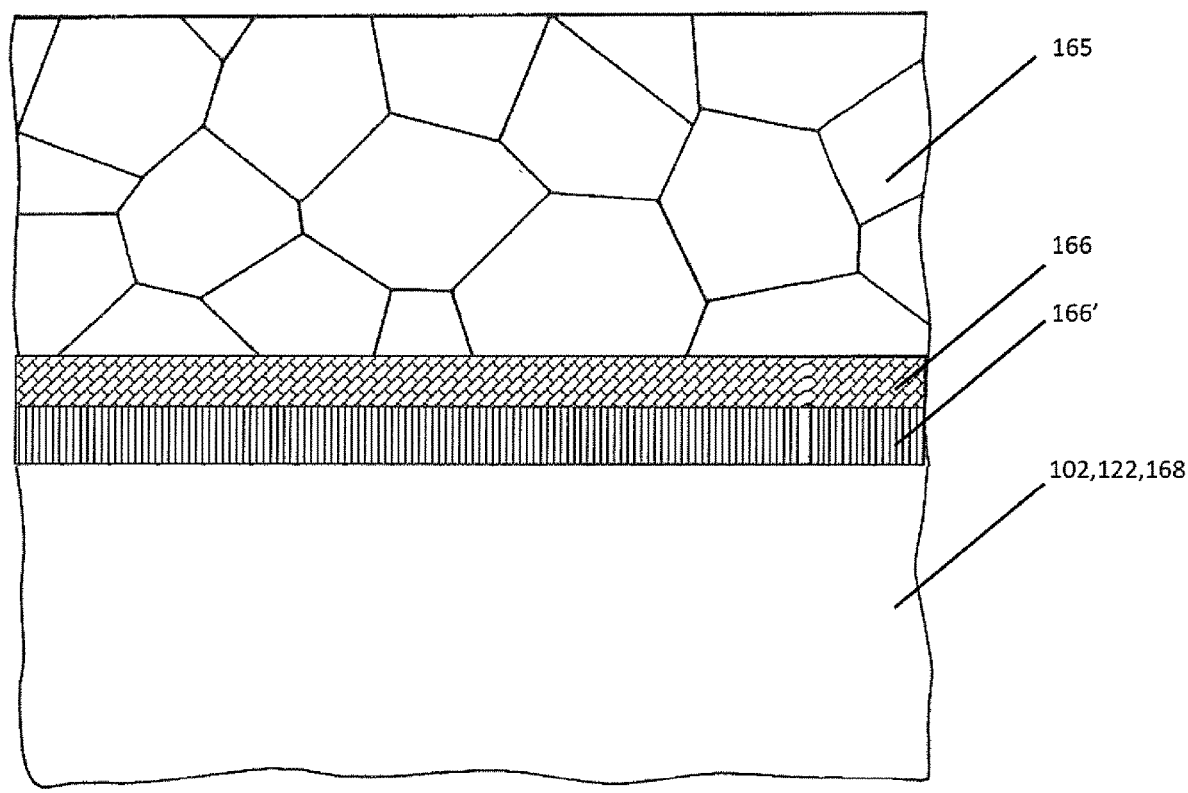
FIG. 32B is a schematic representation of an optional barrier layer(s) that inhibits diffusion of oxidizable base metal substrate materials through an oxide-resistant coating layer.

FIG. 32B is a schematic representation of an optional barrier layer(s) 166,166' that inhibits all of the diffusion mechanisms of FIG. 32A, that is, inhibits lattice, defect path and interdiffusion of the oxidizable materials 102,122,168 through and to the surface of the oxide-resistant coating 165. Referring once again to the exemplar Ti—Au system, providing a barrier layer 166 between the titanium 102,122,168 and the gold can prevent titanium migration to the free surface of the gold layer 165, two way lattice diffusion or interdiffusion and intermetallic formation at the interface. The barrier layer 166 must, however, be stable at typical AIMD processing conditions so that the barrier layer 166 can effectively suppress such titanium diffusion. As an example, barrier layer 166, comprising platinum (Pt), palladium (Pd), rhodium (Rh) or alloys thereof disposed between the titanium surface and the gold can sufficiently suppress each titanium diffusion mechanism. The barrier layer system of FIG. 32B is shown having two barrier layers 166,166', however, it is understood that one barrier layer be used or more than two layers up to "n" number of barrier layers may be used. Researchers have shown that, after annealing Ti—Pd—Au test samples in air, no diffusion of titanium is evident in this one-layer barrier system, wherein the one-layer barrier system comprises a Pd barrier layer 166. The suppression of titanium diffusion is likely due to a rapid grain boundary diffusion of gold in the palladium grain boundaries, which are thereby effectively blocked by gold, hence, this particular Pd—Au interaction therein completely suppresses any substantial migration and diffusion of the titanium. Thus, the optional barrier layer 166 provides an effective alternative for sustaining coating layer 165 oxide-resistance, as such barrier layers 166 can effectively suppress titanium diffusion to and subsequent oxidation at a free (top) metal surface 165.

Another exemplar barrier layer embodiment comprises a nickel barrier layer atop an oxide-resistant gold layer to which a solder is used as the electrical connection material. In this embodiment, the ferrule 122 is thoroughly cleaned, and then a nickel barrier layer 166 is disposed on the surface of the cleaned titanium ferrule 122. Atop the nicker barrier layer 166, a gold oxide-resistant coating 165 is disposed. This gold layer is substantially thick (>1 μm) so that a subsequent attachment of an electrical connection material 143 does not damage the connection. For example, if electrical connection material 143 comprises solder having a high lead (Pb) content, then a thin gold oxide-resistant coating 165 can readily dissolve into the molten solder. Platinum, palladium and alloys thereof can be used as barrier layers for gold, so that molten solder does dissolve in the gold, an oxide-resistant attachment to the titanium is preserved. Alternatively, platinum, palladium and alloys thereof provide an excellent alternative to gold layers altogether, as these materials prevent both metal diffusion and migration, thus, titanium would not be able to reach the free metal surface, and then oxidize. Additionally, platinum, palladium and alloys thereof are also solderable. Thus, while preserving oxide-free electrical connection integrity, platinum, palladium and alloys thereof additionally prevent solder leaching of a eutectic or a soldered component, therein also preserving the mechanical integrity of the attachment. Moreover, neither palladium nor platinum themselves form oxides or migrate easily.

Oxide-resistant coatings 165 may also be used to enable solderability of titaniums. In this case, an oxide-resistant solderable material in accordance with the present invention is disposed on a cleaned titanium surface. Examples of oxide-resistant solderable materials that can be disposed on titanium include gold, palladium, platinum, rhodium, and combinations and alloys thereof.

Figure 33:
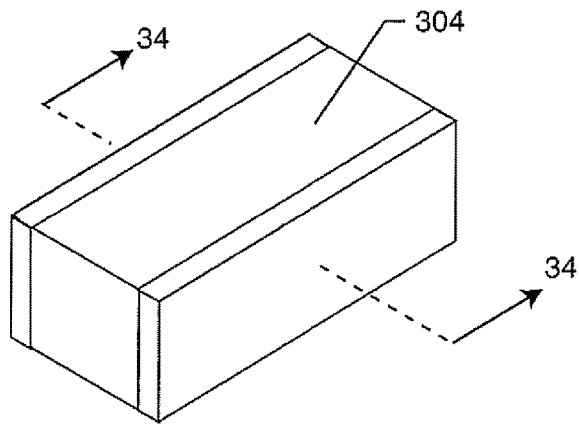
FIG. 33 is a pictorial view of a prior art reverse geometry MLCC chip capacitor.

FIG. 33 illustrates a prior art reverse geometry MLCC chip capacitor 304.

Figure 34:
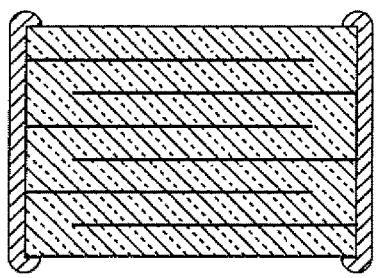
FIG. 34 is a sectional view taken from section 34-34 from FIG. 33.

FIG. 34 is taken from section 34-34 from FIG. 33 showing the internal electrode plates of the reverse geometry MLCC chip capacitor 304. The advantage of the reverse geometry MLCC chip capacitor is greatly reduced inductance and superior high frequency filtering performance.

Figure 35:
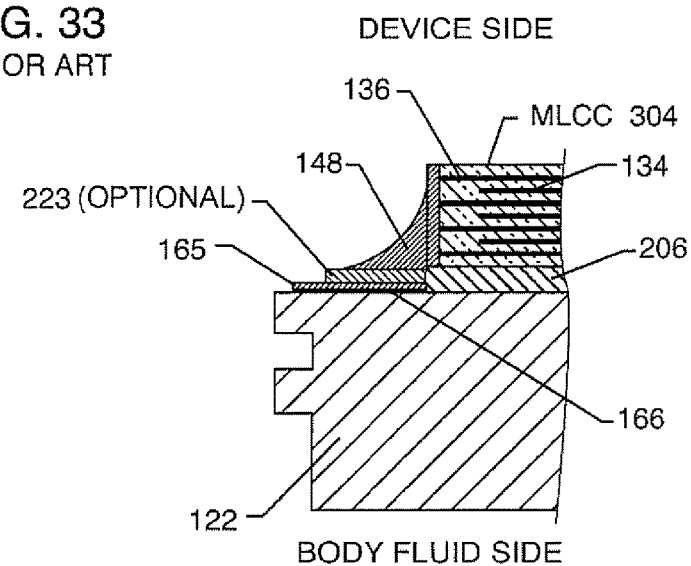
FIG. 35 is a sectional view illustrating the reverse geometry MLCC chip capacitor attached in an oxide-resistant manner of the present invention to an optional ECA stripe disposed atop an oxide-resistant coating or layer.

FIG. 35 shows the reverse geometry MLCC chip capacitor 304 mounted to ferrule 122 using the optional ECA stripe 223 and/or the required oxide-resistant coating 165 of the present invention.

Figure 36:
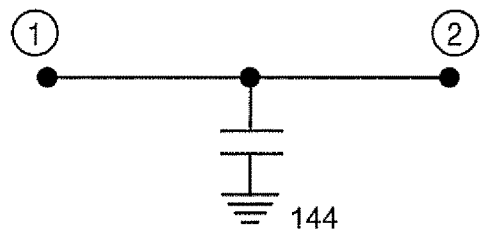
FIG. 36 illustrates an ideal electrical schematic diagram of the filter capacitor reverse geometry MLCC chip capacitor shown in FIG. 33.

FIG. 36 is the schematic diagram of the reverse geometry MLCC chip capacitor 304. Notably, no resistance or inductance is present in this schematic as this configuration offers superior high frequency filter performance at a very low impedance, Z.

FIG. 37 is a prior art quadpolar flat-thru capacitor 400'. It has four active terminations 402, 406 and two ground terminations 404, 404'.

FIG. 38 is taken from section 38-38 from FIG. 37 and illustrates the active electrodes 412a through 412d. Also shown in the lower part of FIG. 38, are the set of ground electrodes 414. These are connected to terminations on the left side 404 and on the right side 404'.

Figure 39:
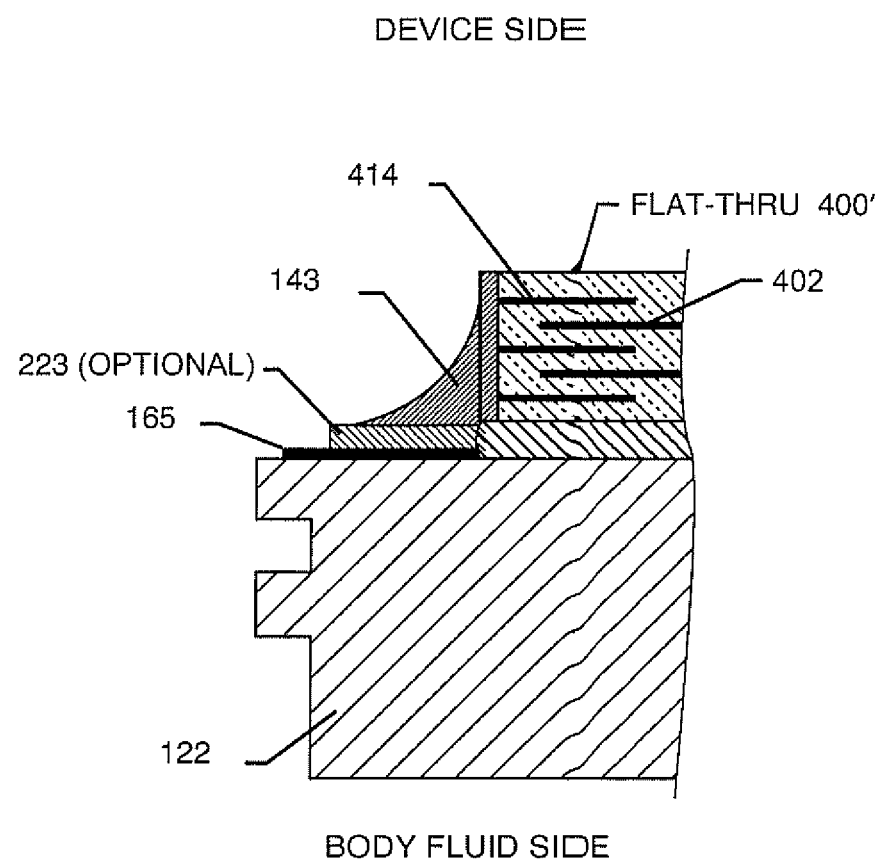
FIG. 39 is a sectional view of the flat-thru capacitor of FIG. 37 with a system ground attachment to an optional ECA stripe and, in turn, to the oxide-resistant coating or layer.

FIG. 39 shows one ground termination of the quadpolar flat-thru capacitor 400' of FIG. 37 attached to ferrule 122. Attachment material 143 connects to optional ECA stripe 123 and/or in turn, to the oxide-resistant coating layer 165. The electrical attachment material is connected to the flat-thru capacitor edge metallization 404 as indicated. Flat-thru capacitor ground electrode plates 414 are also indicated.

Figure 39A:
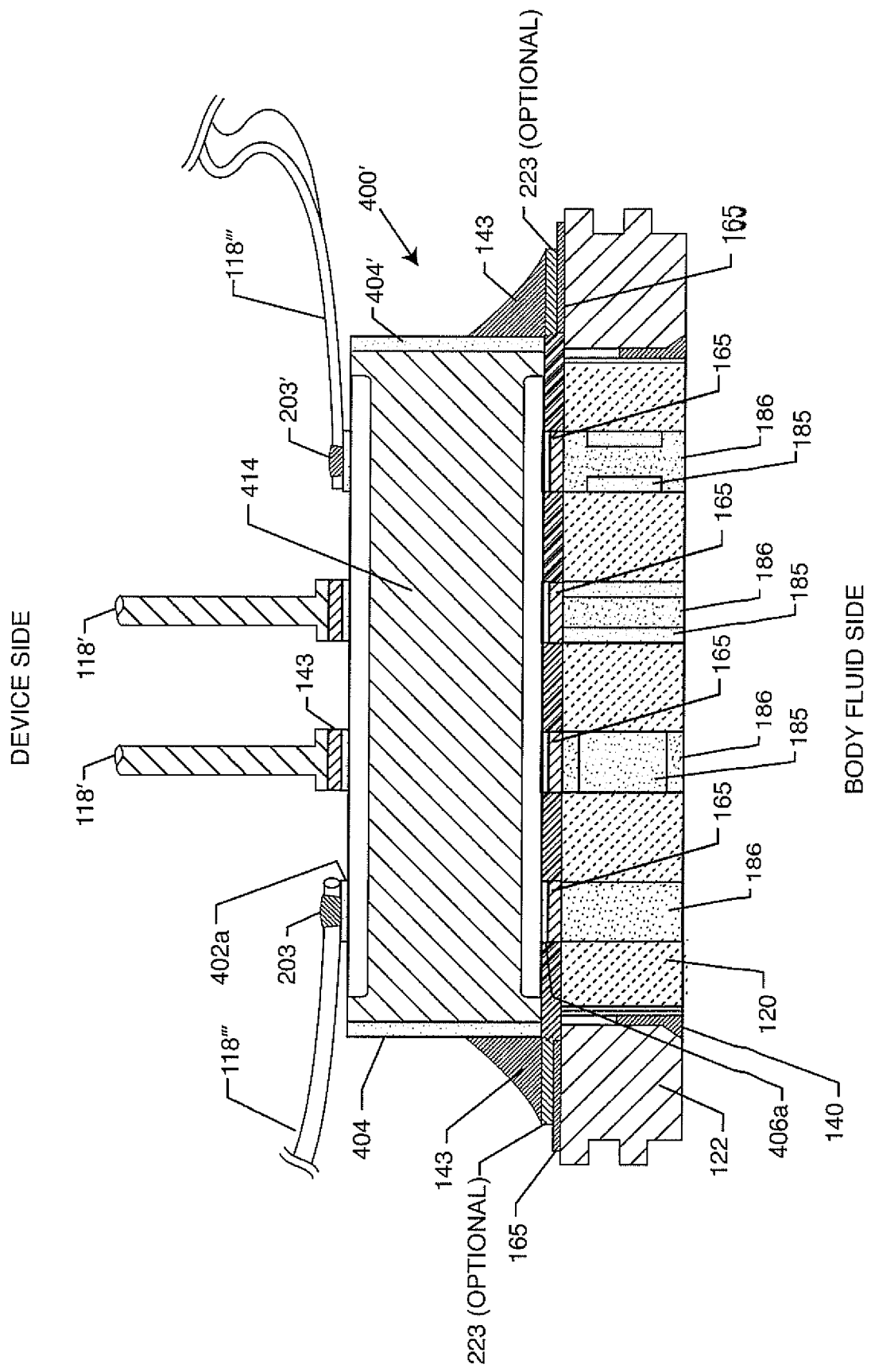
FIG. 39A illustrates the flat-thru capacitor of FIG. 37 mounted in a tombstone position to optional ECA stripes disposed atop an oxide-resistant coating or layer on the surface of a feedthrough ferrule.

FIG. 39A shows the flat-thru capacitor 400' of FIG. 37 mounted in a tombstone position to an insulator and ferrule for an AIMD hermetic terminal assembly. Tombstone-mounted flat-thrus are taught by U.S. Pat. No. 10,874,866, the contents of which are herein incorporated fully by this reference. One can see in this unique construct that the flat-thru capacitor ground terminations 404 are electrically connected 143 to the optional ECA layer 223 and/or the oxide-resistant coating 165 of the present invention. Referring once again to FIG. 39A, one can see various types of co-sintered vias that include a CRMC material 185 and a pure platinum material 186.

Figure 39B:
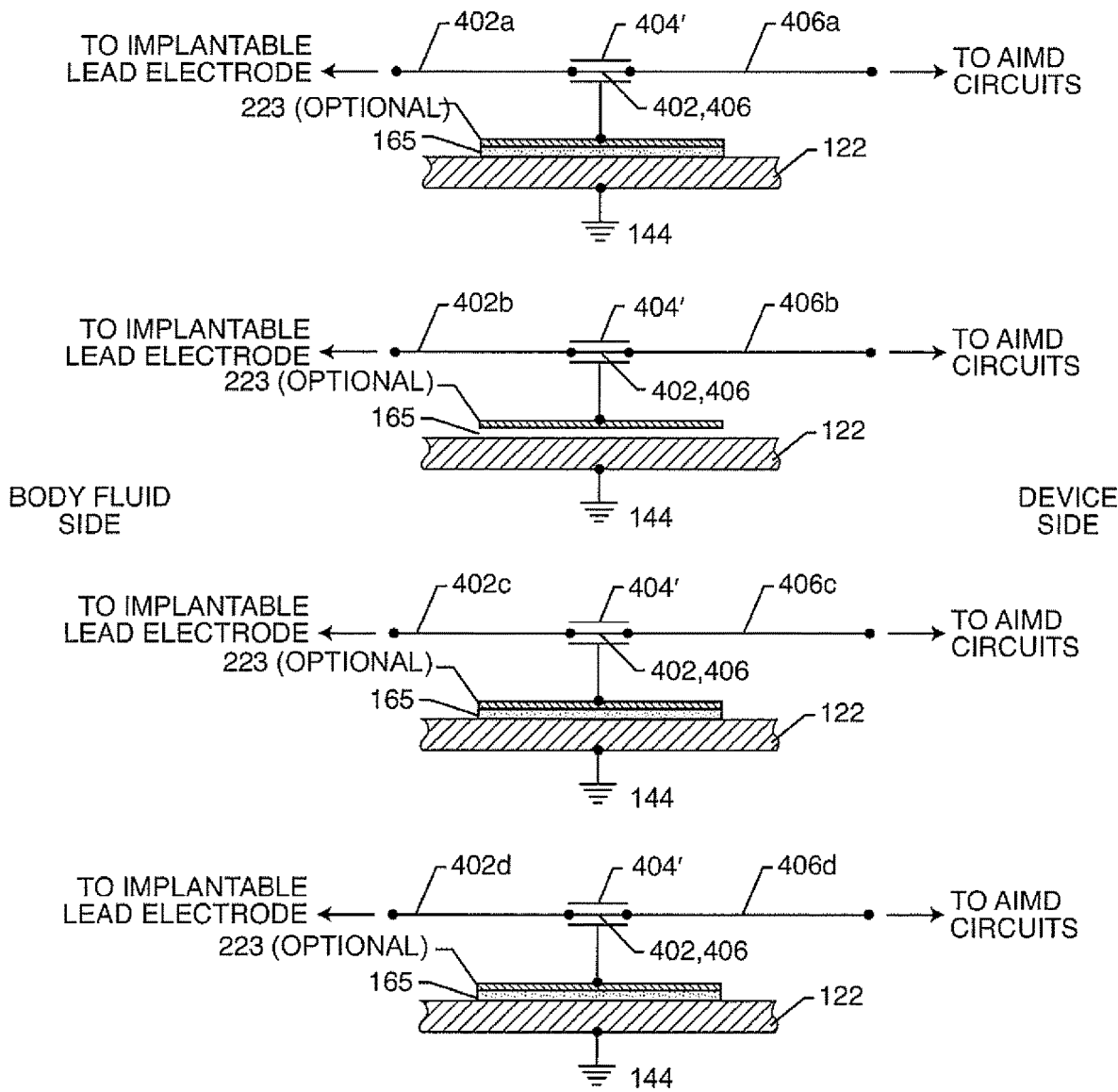
FIG. 39B illustrates the schematic of the flat-thru filter capacitor of FIGS. 37 and 39A.

FIG. 39B illustrates the schematic diagram of the flat-thru capacitor of FIGS. 37 and 39. Referring once again to FIG. 39A, one can see that the flat-thru capacitor ground is connected to the optional ECA stripe 223 and/or, in turn, to the oxide-resistant coating 165 and then to ferrule 122.

Figure 40:
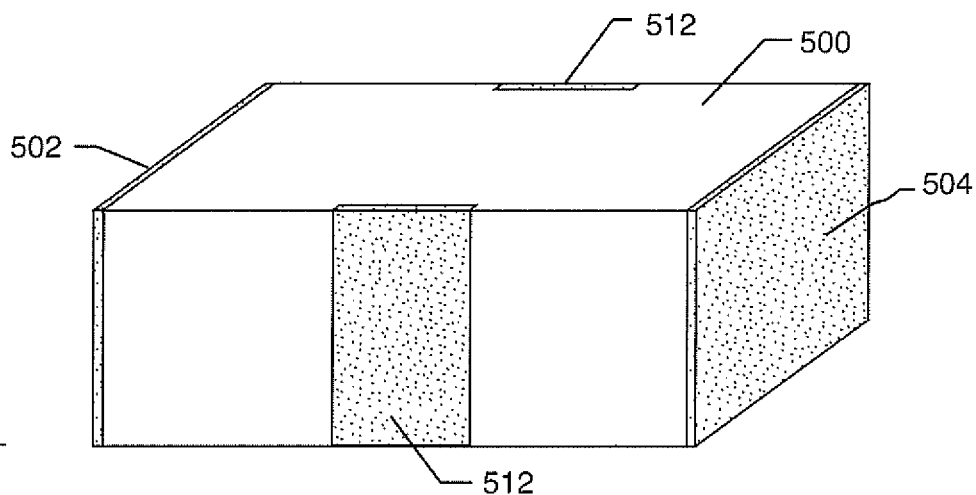
FIG. 40 is a pictorial view of a prior at X2Y attenuator.

FIG. 40 illustrates a prior art X2Y attenuator 500. As indicated, it has active metallizations 502 and 504 and ground metallizations 512.

Figure 40A:
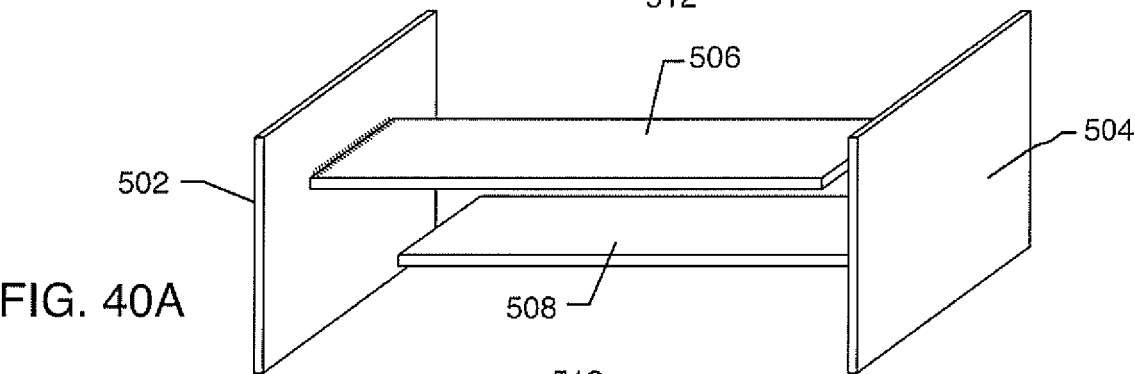
FIG. 40A is an exploded section showing the active electrode plates of the X2Y attenuator of FIG. 40.

FIG. 40A illustrates the two active electrode plates 506 and 508 of the X2Y attenuator. Terminations 502 and 504 connect to the active plates 506 and 508.

Figure 40B:
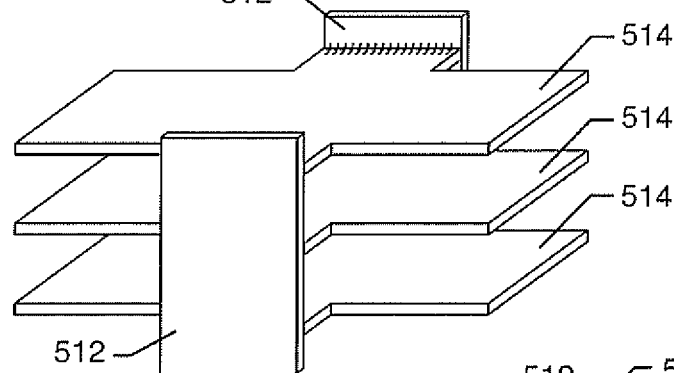
FIG. 40B is an exploded view showing the ground electrode plates of the X2Y attenuator of FIG. 40.

FIG. 40B illustrates the X2Y attenuator ground electrode plate set 514. These ground electrode plates are connected to ground terminations 512, as shown.

Figure 40C:
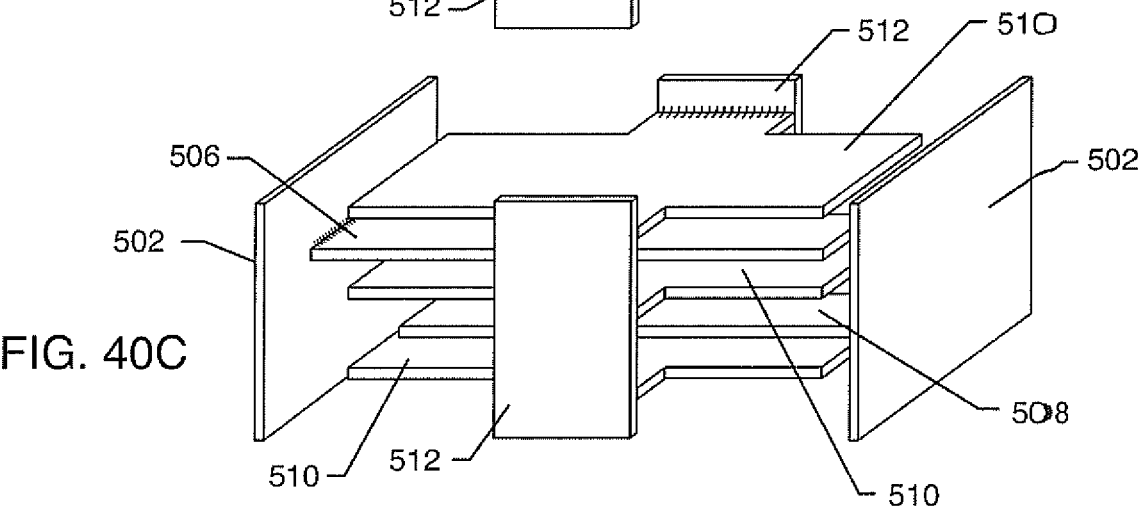
FIG. 40C is an exploded view showing how the ground and active electrode plates of the X2Y attenuator of FIG. 40 are interleaved.

FIG. 40C illustrates the entire X2Y attenuator with the ground electrode plates 510 interleaved with the active electrode plates 506 and 508.

Figure 40D:
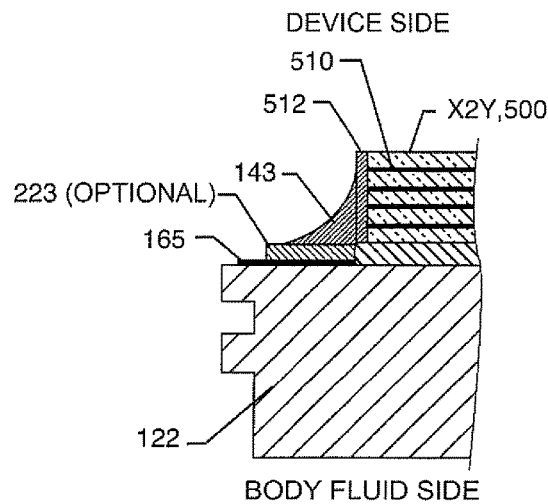
FIG. 40D illustrates the X2Y attenuator of FIG. 40 with a system electrical ground connection to the ferrule in an oxide-resistant manner of the present invention.

FIG. 40D is a sectional view of the X2Y attenuator 500 of FIG. 40 attached to ferrule 122. As can be seen, the metallization 512 of the system ground 144 is electrically connected 143 to the optional ECA stripe 223 and/or, in turn, to the oxide-resistant coating 165 of the present invention. Referring once again to FIG. 40D, one can see that the ground termination 512 connects to the X2Y attenuator ground plates 510.

Figure 40E:
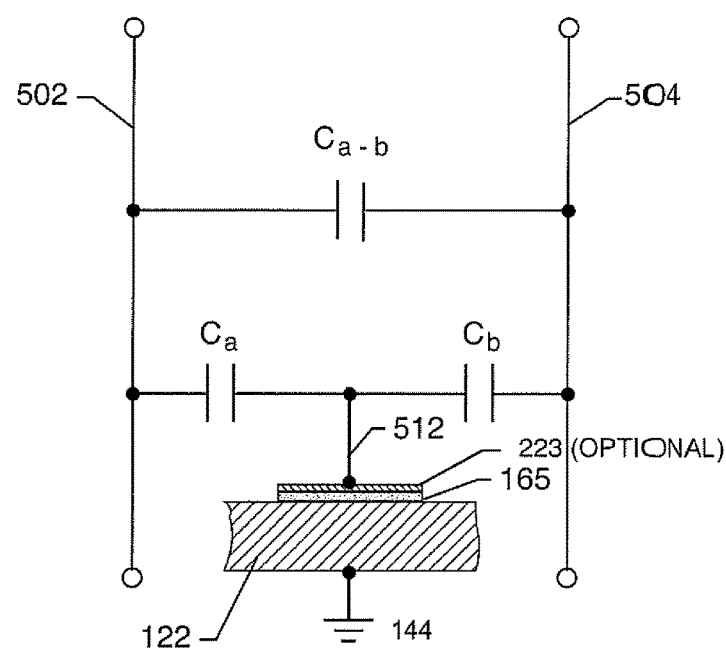
FIG. 40E illustrates the schematic diagram of the X2Y attenuator of FIG. 40D.

FIG. 40E illustrates the schematic diagram of the X2Y attenuator 500 of FIGS. 40 and 40D. Importantly, the system electrical ground connection 144,512 is to the optional ECA stripe 223 and the oxide-resistant coating layer 165 and to ferrule 122. In general, all of the filter components of the present invention are disposed on the device side of the hermetic seal insulator ferrule to protect said components from body fluid.

Figure 41:
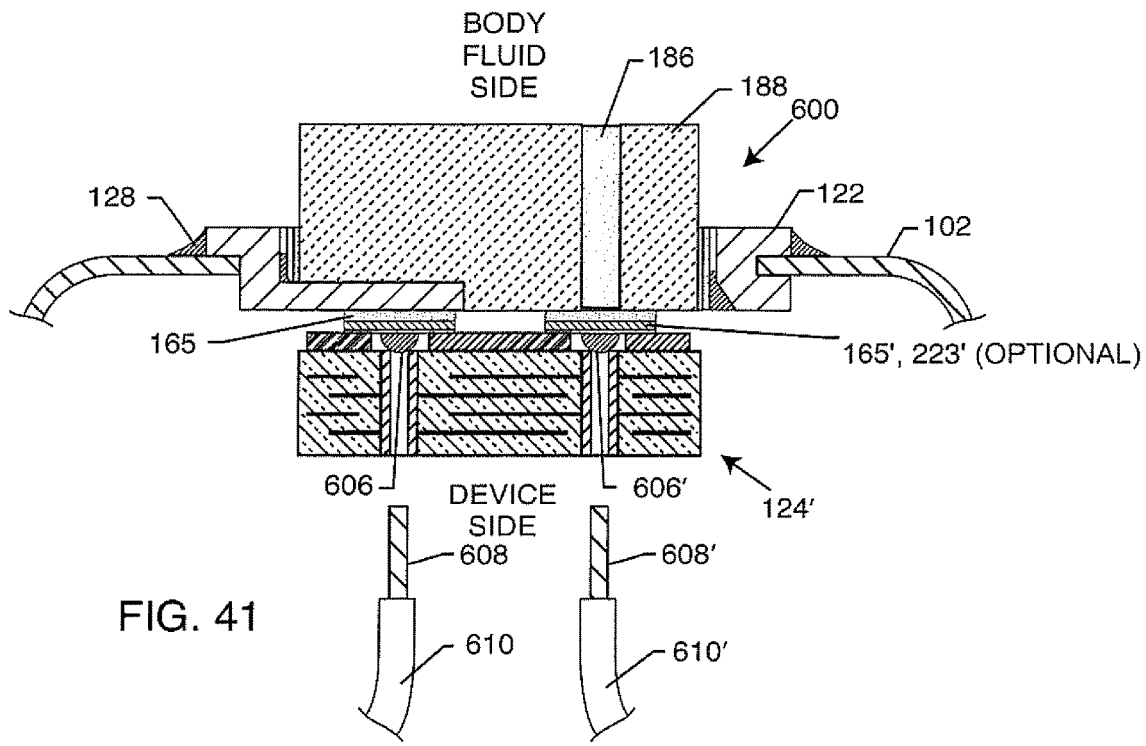
FIG. 41 illustrates an internally grounded feedthrough capacitor attached to an oxide-resistant coating on a ferrule peninsula.

FIG. 41 illustrates a ceramic body or insulator 188 that has been gold brazed to ferrule 122. On the left-hand side of FIG. 41, there is a peninsula structure, which is very similar to the ground peninsula structure taught in FIGS. 13A, 13B and 13C. Instead of the leadwires of FIGS. 13A, 13B and 13C, the peninsula provides a ground for an internally grounded feedthrough capacitor 124'. The internally grounded feedthrough capacitor ground electrode plates are connected to the left-hand feedthrough capacitor via hole through electrical connection 606 to the optional ECA stripe 223 and the oxide-resistant coating 165 of the present invention. This provides the system ground 144 for the internally grounded feedthrough capacitor. Internally grounded feedthrough capacitors are taught by U.S. Pat. No. 5,905,627, the content of which are incorporated herein fully by this reference. Referring again to FIG. 41, one can see that the active via om the right-hand side is a co-sintered conductive via consisting of conductive material 186, comprising substantially pure platinum. The conductive via can also have an oxide-resistant coating 165' and an optional ECA stripe 223' of the present invention for convenient mounting of the internally grounded feedthrough capacitor through electrical connection material 606 and 606'.

Figure 42:
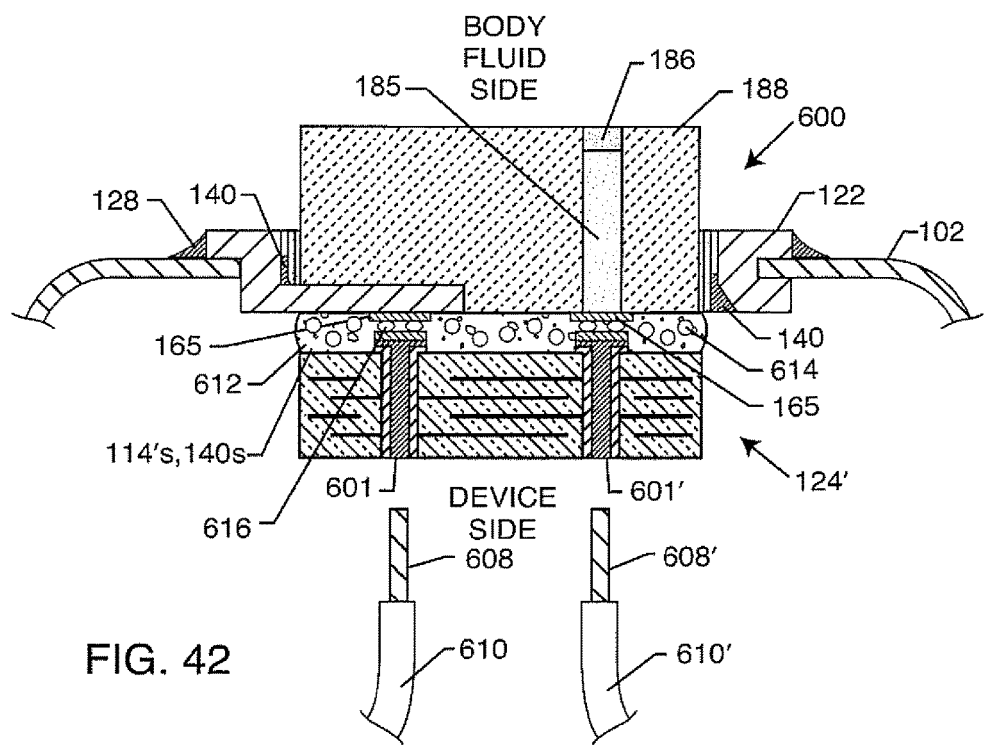
FIG. 42 is similar to FIG. 41, wherein the electrical connection to the oxide-resistant coating and optional ECA stripe is accomplished by an anisotropic conductive film.

FIG. 42 is very similar to FIG. 41, except that the internally grounded feedthrough capacitor is electrically attached to the oxide-resistant coating layer 165 of the present invention using an anisotropic conductive film (ACF) 612. Referring back to FIG. 42, one can see a nail headed structure is inserted or soldered or filled into the internally grounded feedthrough capacitor 124' via holes. As previously noted, oxide-resistant coating layer 165 is shown proud of a ferrule 122 bottom surface and also the insulator 120 surface. These proud areas compress the conductive particles 616 of the ACF film 612. Therefore, electric conductivity only occurs in these areas. In general, uncompressed ACF sphere 614 do not electrically connect or only electrically connect horizontally for a very short space. ACF films are ideal in the present application, as unlike molten solder, they do not tend to dissolve the adjacent terminations. This makes the use of a relatively thick, but proud oxide-resistant material 165 (without the optional ECA stripe 223) an ideal and low-cost alternative.

Figure 43:
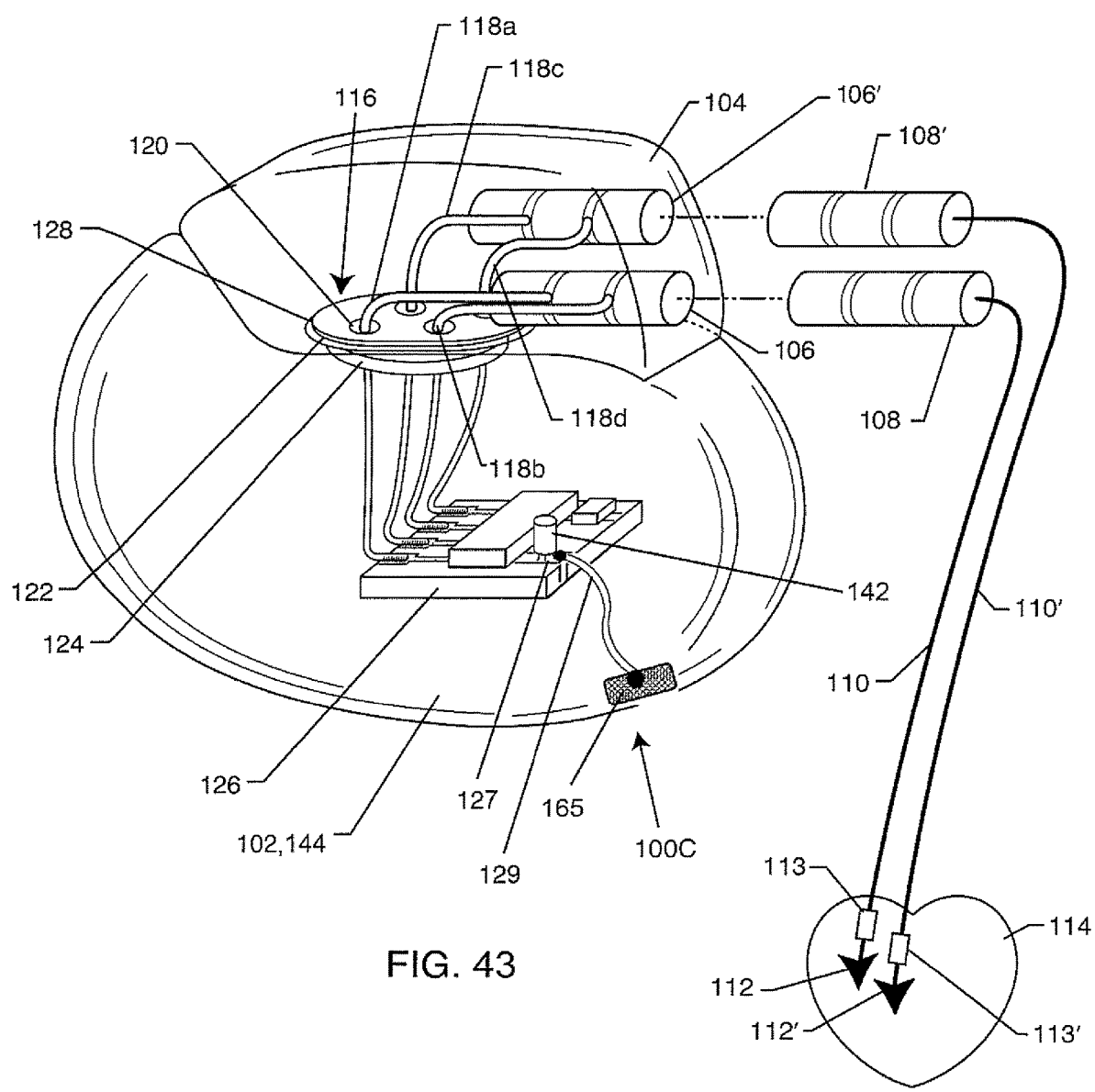
FIG. 43 is similar to FIG. 2 except that the AIMD circuit board system electrical ground connection is made to an oxide-resistant coating of the present invention disposed on an area of the AIMD housing.

FIG. 43 shows a section of a prior art AIMD such as a cardiac pacemaker, as previously illustrated in FIG. 2. One can see an AIMD electronic circuit board 126. There is at least one AIMD electronic circuit board 126 ground circuit trace 127, as indicated. In this case, there is a grounding wire or a grounding strap 129 that connects the circuit board ground trace to the AIMD housing 102. In accordance with the present invention, a surface area 165 has been cleaned and prepared with the oxide-resistant coating 165 of the present invention on the inside of the AIMD housing 102 thereby allowing the ground leadwire 129 to be electrically connected to system ground 102, 144, as indicated. The electrical connection of the ground leadwire or ground strap 129 to the ground circuit trace 127 of the oxide-resistant layer 165 can be of any of the methods previously described in the present invention, including solders, electrically conductive adhesives and the like.

Figure 44A:
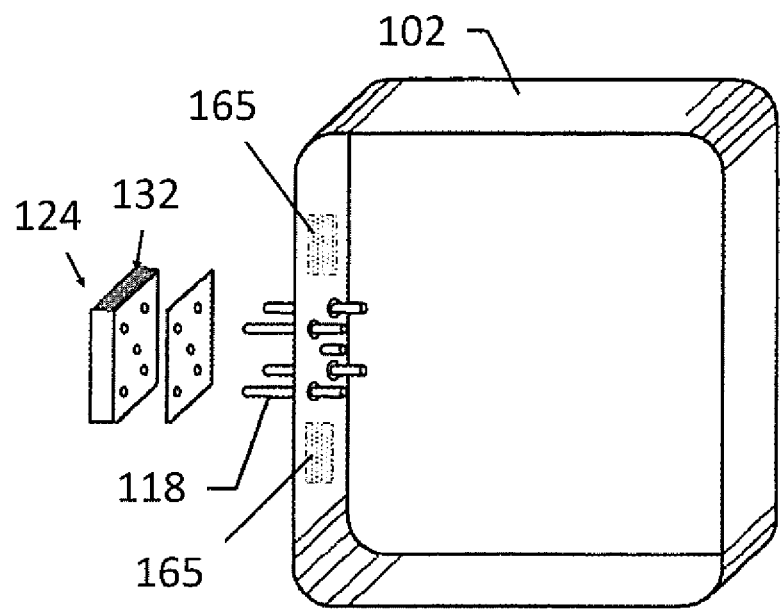
FIG. 44A illustrates a prior art AIMD housing with oxide-resistant coatings of the present invention disposed on the AIMD body fluid side. Shown is a feedthrough capacitor ready to be disposed on the AIMD body fluid side and mounted to the terminal pins with a system electrical ground connection to the oxide-resistant coatings

FIG. 44A shows a prior art AIMD housing 102. In this particular case, leadwires 118 penetrate through the housing 102 in non-conductive relationship. There are either glass seals or gold braze insulators (not clearly shown). In this case, there is no ferrule as the leadwires directly penetrate through the can and are individually insulated. Shown, are two oxide-resistant coating layers 165 of the present invention illustrated with dashed lines about the perimeter. This indicates that they are on the outside of the AIMD housing 102 and cannot be clearly visualized in this view. There is a prior art rectangular feedthrough capacitor 124 with ground metallizations 132, as indicated. It is ready for mounting over the terminal pins 118 and for a system ground connection 144 to be made between the filter ground termination 132 and the oxide-resistant surface areas 165 of the AIMD housing 102. Not shown, is an opposite ground termination on the bottom of the feedthrough capacitor 132, which would be also electrically connected to the lower oxide-resistant coating 165. At first glance, it would not be obvious that the feedthrough capacitor 124 could be mounted on the outside of the AIMD housing 102 and be directly exposed to body fluid. However, one is referred to U.S. Pat. No. 6,985,347 which teaches the special design of feedthrough capacitors that are compatible with body fluid. This requires the use of noble electrodes, such as platinum electrodes, gold terminations 132 and the like. The electrical connection between the capacitor ground terminations 132 and the oxide-resistant layers 164 would also have to be of a suitable biocompatible material, such as a gold or platinum filled thermal-setting conductive polyimide.

Referring once again to FIG. 44A, one will see that the housing 102 is opened up. It will be appreciated that some sort of a hermetically sealed biocompatible lid would need to be laser welded or attached, such that the AIMD or internal electronic circuits are protected from body fluids. The AIMD housing 102 is generally metallic, fox example, titanium, such that AIMD electronic circuits are shielded from radiated electromagnetic interference.

Figure 44B:
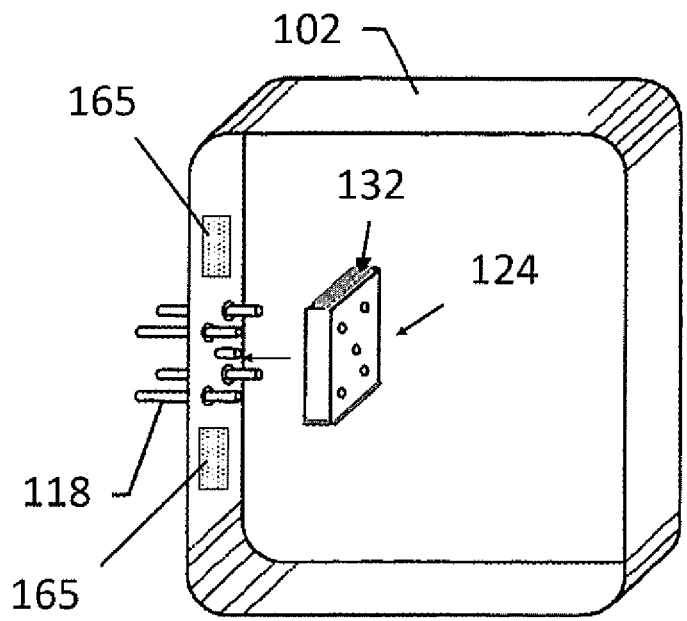
FIG. 44B is very similar to FIG. 44A, but in this case, the oxide-resistant coatings are disposed on the inside or the device side of the AIMD housing. In this case, the filter capacitor ground terminations are electrically connected to the oxide-resistant system ground pads on the device side.

FIG. 44B is very similar to FIG. 44A, except in this case, the oxide-resistant surface areas 165 are clearly visualized on the inside of the AIMD housing 102. In this case, the feedthrough capacitor 124 need not be biocompatible since it is on the inside of the AIMD housing and thereby protected against body fluids. In this case, there would be an electrical system ground connection 143,144 between the feedthrough capacitor ground terminations 132 and the oxide-resistant coating layers 165. This can be a typical solder or an electrically conductive adhesive (ECA) that does not require biocompatibility since this connection is on the inside of the AIMD housing 102. Again, referring back to FIG. 44B, in this construct, there is no ferrule required. However, it is still required to provide oxide-resistant ground connection coating areas for the feedthrough capacitor 124.

Figure 45:
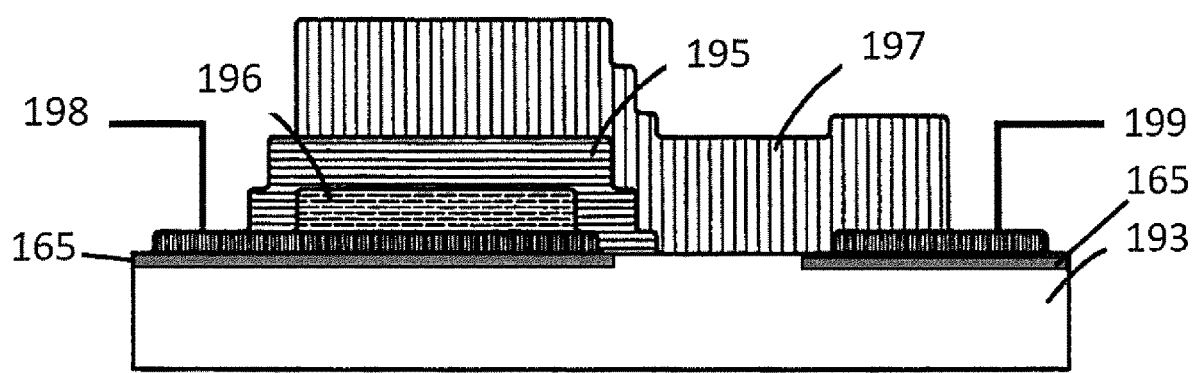
FIG. 45 is a schematic of a thin film battery illustrating the anode and cathode current collectors electrically connected to an oxide-resistant coating on the surface of a substrate.

FIG. 45 is a schematic of a thin film battery illustrating the anode and cathode current collectors 197,198 respectively electrically connected to an oxide-resistant coating 165 on the surface of a substrate 193. While the embodiment shown in FIG. 45 is a this film battery, it is understood that the thins film battery shown is only exemplary, and the oxide-resistant coatings 165 of the present invention also applies to batteries in general, capacitors, resistors, and other thin film and electrical structures needing low resistant low impedance temperature stable electrical connections.

Figure 46:
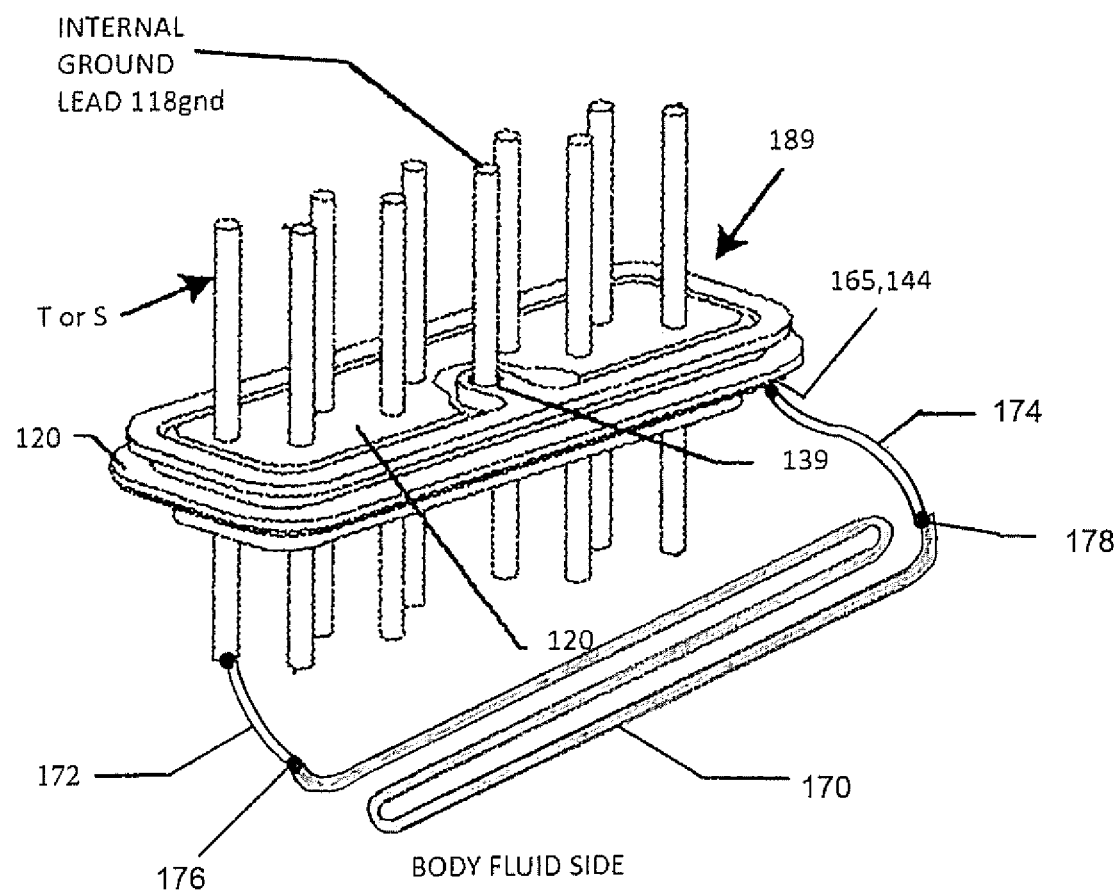
FIG. 46 is very similar to FIG. 13B, except in this case, a telemetry antenna is disposed in a header block (not shown) on the body fluid side and is grounded to an oxide-resistant coating on the body fluid side ferrule surface.

FIG. 46 is taken from FIG. 13B and does not show the internally grounded feedthrough capacitor 124' but will be appreciated that this is easily installed in this construct. Referring once again to FIG. 46, one can see that there is a prior art RF telemetry antenna 170. These antennas have a variety of shapes and the geometry, as shown in 170, which is not limiting. What is important is that one end of the RF telemetry antenna 170 is actively connected 172 to the RF telemetry pin T.

Referring back to FIGS. 13A through 13C, it will be appreciated that the RF telemetry pin is not associated with a filtered capacitor. This is best understood by examining the internal active electrodes of FIG. 13A. There is no active filtered capacitor electrode associated with the telemetry pin. The reason for this is any filtered capacitance on the telemetry pin would degrade the RF telemetry pin thereby rendering it inoperable or ineffective. Importantly, the other end of the RF telemetry antenna 170 has a ground connection 174 to a body fluid side of the ferrule that has been cleaned and prepared with an oxide-resistant surface coating 165 of the present invention. This also forms a system ground 144 for the RF telemetry antenna 170, as shown.

Referring once again to FIG. 46, one can see that the telemetry pin is marked T (for telemetry) or S (a sensor). Instead of a telemetry pin, an unfiltered pin could be provided for various sensors, such as pulse ox sensors, hemodynamic sensors, glucose sensors or the like. In this case, the sensor's active path would pass through the sensor pin S, and in a similar manner, it could be connected to system ground 65, 144, as indicated for the telemetry antenna 170. As many unfiltered terminal pins can be added to accommodate both telemetry pins and sensors.

FIG. 47 provides further detail regarding embodiments and materials that can be used in any of the embodiments of the present application. Included within this table are patents assigned to the present Applicant regarding EMI filter capacitor, EMI filter circuit boards, and hermetic co-sintered feed throughs, all of which benefit from the low ESR low inductance oxide-resistant attachment of the present application. The contents of all of the patents listed in this table are herein incorporated fully by this reference.

What is claimed:

1. An active implantable medical device (AIMD), comprising:
   a) a titanium or titanium alloy system ground surface comprising at least one of a conductive shield housing for the AIMD, and a conductive ferrule mechanically and electrically connected to an opening in the AIMD shield housing, the titanium or titanium alloy system ground surface having a titanium oxide layer, wherein:
      i) the titanium or titanium alloy system ground surface has an area where the titanium oxide layer has been removed;
      ii) an oxide-resistant electrically conductive coating directly contacted to the area of the titanium or titanium alloy system ground surface where the titanium oxide layer has been removed; and
      iii) an electrically conductive adhesive (ECA) stripe directly contacted to the oxide-resistant electrically conductive coating opposite the area of the titanium or titanium alloy system ground surface where the titanium oxide layer has been removed so that the oxide-resistant electrically conductive coating prevents the ECA stripe from directly contacting the titanium or titanium alloy system ground surface; and
   b) at least one of:
      i) a passive electromagnetic interference (EMI) filter capacitor comprising at least one ground electrode plate interleaved in a capacitive relationship in a dielectric with at least one active electrode plate;
      ii) a passive EMI filter circuit board comprising at least one ground shield plate; and
      iii) an active electronic circuit for the AIMD, the electronic circuit comprising at least one ground trace; and
   c) an electrically conductive material connecting at least one of the at least one ground electrode plate of the passive EMI filter capacitor, the at least one ground shield plate of the passive EMI filter circuit board, and the at least one ground trace of the active electronic circuit to the ECA stripe directly contacted to the oxide-resistant electrically conductive coating directly contacted to the area of the titanium or titanium alloy system ground surface where the titanium oxide layer has been removed.

2. The AIMD of claim 1, wherein the oxide-resistant electrically conductive coating is characterized as having been contacted to the titanium or titanium alloy system ground surface where the titanium oxide layer has been removed by at least one of physical vapor deposition, chemical vapor deposition, electrostatic spray assisted vapor deposition (ESAVD), electron beam physical vapor deposition (EBPVD), ion plating, ion beam assisted deposition (IBAD), magnetron sputtering, pulsed laser deposition, sputter deposition, vacuum deposition, pulsed electron deposition (PED), plating, electroless plating, electroplating, spraying, painting, plasma spraying, thermal spraying, spin coating, dip coating, metal foil lamination, and as a thin film deposited layer.

3. The AIMD of claim 1, wherein the electrically conductive material is selected from a solder, an electrically conductive adhesive, an electrically conductive thermal-setting adhesive, an electrically conductive epoxy, an electrically conductive polyimide, an electrically conductive elastomer, and mixtures thereof.

4. The AIMD of claim 1, wherein the passive EMI filter capacitor is selected from a feedthrough capacitor, an internally grounded feedthrough capacitor, an MLCC chip capacitor, an X2Y attenuator, and a flat-thru capacitor.

5. The AIMD of claim 1,
   a) wherein the at least one of:
      i) the passive EMI filter capacitor is provided with a first metallization contacting the at least one ground electrode plate;
      ii) the passive EMI filter circuit board is provided with a second metallization contacting the at least one ground shield plate; and
      iii) the active electronic circuit is provided with a third metallization contacting the at least one ground trace, and
   b) wherein the electrically conductive material connects the ECA stripe directly contacted to the oxide-resistant electrically conductive coating directly contacted to the titanium or titanium alloy system ground surface where the titanium oxide layer has been removed to the at least one of the first metallization, the second metallization and the third metallization.

6. The AIMD of claim 1, wherein the oxide-resistant electrically conductive coating is selected from gold, a gold alloy, rhodium, a rhodium alloy, platinum, a platinum alloy, a platinum-iridium alloy, palladium, a palladium alloy, nitinol, a cobalt-chromium alloy, and combinations thereof.

7. The AIMD of claim 1, wherein the active electronic circuit for the AIMD comprises an AIMD circuit board provided with the at least one ground trace.

8. The AIMD of claim 1, wherein the oxide-resistant electrically conductive coating is gold having a thickness that is greater than zero but less than 1 µm.

9. The (AIMD) of claim 1, wherein the titanium or titanium alloy system ground surface having the titanium oxide layer is characterized as having been treated in a vacuum environment or a dry inert atmosphere to remove the titanium oxide layer by at least one of sanding with alumina abrasive paper, sanding with an alumina abrasive mat, grinding, grit blasting with alumina, grit blasting with glass beads, brushing with a stainless-steel brush, tumbling, immersion in an alkaline cleaner containing sodium gluconate, immersion in an aqueous alkaline hydroxide solution containing a calcium salt, acid etching with nitric acid, acid etching with sulfuric acid, acid etching with a hydrofluoric-containing acid, acid etching in a mixture of nitric acid and hydrofluoric acid, electropolishing in a chloride-based solution, electropolishing in a sulfuric acid-methanol-based solution, electropolishing is a perchlorate-free electrolyte, plasma etching, and combinations thereof.

10. The (AIMD) of claim 9, wherein the dry inert atmosphere is selected from argon, nitrogen, helium, and mixtures thereof.

11. The AIMD of claim 1, wherein the ECA stripe is selected from a thermal-setting electrically conductive adhesive, an electrically conductive polymer, an electrically conductive epoxy, an electrically conductive silicone, an electrically conductive polyamide, and an electrically conductive polyimide.

12. An active implantable medical device (AIMD), comprising:
a) a titanium or titanium alloy system ground surface comprising at least one of a conductive shield housing for the AIMD, and a conductive ferrule mechanically and electrically connected to an opening in the AIMD shield housing, the titanium or titanium alloy system ground surface having a titanium oxide layer, wherein:
  i) the titanium or titanium alloy system ground surface has an area where the titanium oxide layer has been removed;
  ii) a barrier layer directly contacted to the area of the titanium or titanium alloy system ground surface where the titanium oxide layer has been removed;
  iii) an oxide-resistant electrically conductive coating directly contacted to the barrier layer; and
  iv) an electrically conductive adhesive (ECA) stripe directly contacted to the oxide-resistant electrically conductive coating opposite the barrier layer so that the oxide-resistant electrically conductive coating prevents the ECA stripe from directly contacting the barrier layer directly contacted to the titanium or titanium alloy system ground surface where the titanium oxide layer has been removed; and
b) at least one of:
  i) a passive electromagnetic interference (EMI) filter capacitor comprising at least one ground electrode plate interleaved in a capacitive relationship in a dielectric with at least one active electrode plate;
  ii) a passive EMI filter circuit board comprising at least one ground shield plate; and
  iii) an active electronic circuit for the AIMD, the electronic circuit comprising at least one ground trace; and
c) an electrically conductive material connecting at least one of the at least one ground electrode plate of the passive EMI filter capacitor, the at least one ground shield plate of the passive EMI filter circuit board, and the at least one ground trace of the active electronic circuit to the ECA stripe directly contacted to the oxide-resistant electrically conductive coating directly contacted to the barrier layer directly contacted to the area of the titanium or titanium alloy system ground surface where the titanium oxide layer has been removed,
d) wherein the ECA stripe is selected from a thermal-setting electrically conductive adhesive, an electrically conductive polymer, an electrically conductive epoxy, an electrically conductive silicone, an electrically conductive polyamide, and an electrically conductive polyimide.

13. The AIMD of claim 12, wherein the barrier layer is characterized as having been contacted to the titanium or titanium alloy system ground surface where the titanium oxide layer has been removed by at least one of physical vapor deposition, chemical vapor deposition, electrostatic spray assisted vapor deposition (ESAVD), electron beam physical vapor deposition (EBPVD), ion plating, ion beam assisted deposition (IBAD), magnetron sputtering, pulsed laser deposition, sputter deposition, vacuum deposition, pulsed electron deposition (PED), plating, electroless plating, electroplating, spraying, painting, plasma spraying, thermal spraying, spin coating, dip coating, metal foil lamination, and as a thin film deposited layer.

14. The AIMD connection of claim 12, wherein the barrier layer is nickel, and the oxide-resistant electrically conductive coating is gold having a thickness that is greater than zero but less than 1 µm.

15. The AIMD of claim 12, wherein the barrier layer is selected from nickel, palladium, platinum, rhodium, ruthenium, molybdenum, chromium, nickel-vanadium, nichrome, nickel-iron, palladium-cobalt, cobalt-tantalum, nickel alloys, palladium alloys, platinum alloys, titanium nitride, zirconium nitride, hafnium nitride, vanadium nitride, tantalum nitride, molybdenum nitride, tungsten nitride, and combinations thereof.

16. The AIMD of claim 12, wherein the passive EMI filter capacitor is selected from a feedthrough capacitor, an internally grounded feedthrough capacitor, an MLCC chip capacitor, an X2Y attenuator, and a flat-thru capacitor.

17. The AIMD of claim 12,
a) wherein the at least one of:
  i) the passive EMI filter capacitor is provided with a first metallization contacting the at least one ground electrode plate;
  ii) the passive EMI filter circuit board is provided with a second metallization contacting the at least one ground shield plate; and
  iii) the active electronic circuit is provided with a third metallization contacting the at least one ground trace, and
b) wherein the electrically conductive material directly electrically connects the at least one of the first metallization, the second metallization and the third metallization to the ECA stripe directly contacted to the oxide-resistant electrically conductive coating directly contacted to the barrier layer in turn directly contacted to the area of the titanium or titanium alloy system ground surface where the titanium oxide layer has been removed.

18. The AIMD of claim 12, wherein the active electronic circuit for the AIMD comprises an AIMD circuit board provided with the at least one ground trace.

19. The (AIMD) of claim 12, wherein the titanium or titanium alloy system ground surface having the titanium oxide layer is characterized as having been treated in a vacuum environment or a dry inert atmosphere to remove the titanium oxide layer by at least one of sanding with alumina abrasive paper, sanding with an alumina abrasive mat, grinding, grit blasting with alumina, grit blasting with glass beads, brushing with a stainless-steel brush, tumbling, immersion in an alkaline cleaner containing sodium gluconate, immersion in an aqueous alkaline hydroxide solution containing a calcium salt, acid etching with nitric acid, acid etching with sulfuric acid, acid etching with a hydrofluoric-containing acid, acid etching in a mixture of nitric acid and hydrofluoric acid, electropolishing in a chloride-based solution, electropolishing in a sulfuric acid-methanol-based solution, electropolishing is a perchlorate-free electrolyte, plasma etching, and combinations thereof.

20. The (AIMD) of claim 19, wherein the dry inert atmosphere is selected from argon, nitrogen, helium, and mixtures thereof.

21. An active implantable medical device (AIMD), comprising:
   a) a system ground metal surface comprising at least one of a conductive shield housing for the AIMD, and a conductive ferrule mechanically and electrically connected to an opening in the AIMD shield housing, the system ground metal surface having an oxide layer, wherein:
      i) the system ground metal surface has an area where the oxide layer has been removed;
      ii) an oxide-resistant electrically conductive coating directly contacted to the area of the system ground metal surface where the oxide has been removed; and
      iii) an electrically conductive adhesive (ECA) stripe directly contacted to the oxide-resistant electrically conductive coating opposite the area of the system ground metal surface where the oxide layer has been removed so that the oxide-resistant electrically conductive coating prevents the ECA stripe from directly contacting the system ground metal surface; and
   b) at least one of:
      i) A passive electromagnetic interference (EMI) filter capacitor comprising at least one ground electrode plate interleaved in a capacitive relationship in a dielectric with at least one active electrode plate;
      ii) a passive EMI filter circuit board comprising at least one ground shield plate; and
      iii) an active electronic circuit for the AIMD, the electronic circuit comprising at least one ground trace; and
   c) an electrically conductive material connecting at least one of the at least one ground electrode plate of the passive EMI filter capacitor, the at least one ground shield plate of the passive EMI filter circuit board, and the at least one ground trace of the active electronic circuit to the ECA stripe directly contacted to the oxide-resistant electrically conductive coating directly contacted to the area of the system ground metal surface where the oxide layer has been removed,
   d) wherein the ECA stripe is selected from a thermal-setting electrically conductive adhesive, an electrically conductive polymer, an electrically conductive epoxy, an electrically conductive silicone, an electrically conductive polyamide, and an electrically conductive polyimide.

22. The (AIMD) of claim 21, wherein the electrically conductive material connecting the at least one of the at least one ground electrode plate of the passive EMI filter capacitor, the at least one ground shield plate of the passive EMI filter circuit board, and the at least one ground trace of the active electronic circuit to the ECA stripe directly contacted to the oxide-resistant electrically conductive coating is selected from a solder, an electrically conductive adhesive, an electrically conductive thermal-setting adhesive, an electrically conductive epoxy, an electrically conductive polyimide, an electrically conductive elastomer, and mixtures thereof.

* * * * *